(12) United States Patent
Lenormand et al.

(10) Patent No.: US 9,175,048 B2
(45) Date of Patent: Nov. 3, 2015

(54) USE OF PEPTIDES AS TRANSPORTERS INTENDED FOR THE INTERNALIZATION OF MOLECULES OF INTEREST INTO TARGET CELLS

(75) Inventors: Jean-Luc Erwan Claude Francis Lenormand, La Tronche (FR); Romy Rothe-Walther, Toulouse (FR)

(73) Assignee: UNIVERSITE JOSEPH FOURIER, Grenoble Cedex (FR)

( * ) Notice: Subject to any disclaimer, the term of this patent is extended or adjusted under 35 U.S.C. 154(b) by 30 days.

(21) Appl. No.: 13/643,598

(22) PCT Filed: Apr. 7, 2011

(86) PCT No.: PCT/FR2011/050794
§ 371 (c)(1),
(2), (4) Date: Jan. 14, 2013

(87) PCT Pub. No.: WO2011/135222
PCT Pub. Date: Nov. 3, 2011

(65) Prior Publication Data
US 2013/0116201 A1    May 9, 2013

(30) Foreign Application Priority Data
Apr. 26, 2010 (FR) ..................... 10/53179

(51) Int. Cl.
| C07K 14/05 | (2006.01) |
| C07K 14/47 | (2006.01) |
| A61K 38/17 | (2006.01) |
| A61K 47/48 | (2006.01) |
| C07K 14/005 | (2006.01) |

(52) U.S. Cl.
CPC ............ *C07K 14/05* (2013.01); *A61K 38/1709* (2013.01); *A61K 47/48246* (2013.01); *C07K 14/005* (2013.01); *C07K 14/47* (2013.01); *C07K 14/4702* (2013.01); *C07K 2319/10* (2013.01); *C12N 2710/16222* (2013.01)

(58) Field of Classification Search
None
See application file for complete search history.

(56) References Cited

U.S. PATENT DOCUMENTS
5,595,756 A * 1/1997 Bally et al. ............... 424/450

FOREIGN PATENT DOCUMENTS
WO          02/10201 A2   2/2002

OTHER PUBLICATIONS

Rothe et al. J Biol Chem. Jun. 25, 2010;285(26):20224-33. doi: 10.1074/jbc.M110.101550. Epub Apr. 9, 2010.*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Sporn et al, "Chemoprevention of Cancer," Carcinogenesis, vol. 21 (2000), 525-530.*
Auerbach et al (Cancer and Metastasis Reviews, 2000, 19: 167-172).*
Gura T (Science, 1997, 278(5340): 1041-1042, encloses 1-5).*
Jain RK (Scientific American, Jul. 1994,58-65).*
French Search Report, dated Dec. 16, 2010, from corresponding French application.
International Search Report, dated Feb. 7, 2012, from corresponding PCT application.
Romy Rothe et al., "Characterization of the Cell-penetrating Properties of the Epstein-Barr Virus ZEBRA trans-Activator", Journal of Biological Chemistry, Apr. 9, 2010, pp. 20224-20233, vol. 285, No. 26, XP-007916069.
Hiroshi Harada et al., "Antitumor Protein Therapy; Application of the Protein Transduction Domain to the Development of a Protein Drug for Cancer Treatment", Breast Cancer, Jan. 2006, pp. 16-26, vol. 13, No. 1, XP-002544010.
Romy Rothe et al., "Expression and Purification of Zebra Fusion Proteins and Applications for the Delivery of Macromolecules into Mammalian Cells", Current Protocols in Protein Science, Nov. 2008, Chapter 18, XP-007916063.
Eric L. Snyder et al., "Enhanced Targeting and Killing of Tumor Cells Expressing the CXC Chemokine Receptor 4 by Transducible Anti-cancer Peptides", Cancer Reseach, Dec. 1, 2005, pp. 10646-10650, vol. 65, No. 23, XP-002613447.
So-Jung Kwon et al., "Transduction of the MPG-tagged fusion protein into mammalian cells and oocytes depends on amiloride-sensitive endocytic pathway", BMC Biotechnology, 2009, vol. 9.
Camilla Foged et al., "Cell-Penetrating peptides for drug delivery across membrane barriers", Expert Opinion on Drug Delivery, Informational Healthcare, Jan. 1, 2008, pp. 105-117, vol. 5, No. 1, XP-008090485.
Christopher L. Murriel et al., "Influence of protein transduction domains on intracellular delivery of macromolecules", Expert Opinion on Drug Delivery, Informational Healthcare, Nov. 1, 2006, pp. 739-746, vol. 3, No. 6, XP-008107388.
May C. Morris et al., "A peptide carrier for the delivery of biologically active proteins into mammalian cells", Nature Biotechnology, Dec. 1, 2001, pp. 1173-1176, vol. 19, XP-002559236.
J.L. Lenormand et al., Abstract of Speedy: a novel cell cycle regulator of the G2/M transition, The EMBO Journal, Apr. 1, 1999, vol. 18, No. 7.
Lon Phan et al., "Identification of a Translation Initiation Factor 3 (eIF3) Core Complex, Conserved in Yeast and Mammals, That Interacts with eIF5", Molecular and Cellular Biology, Aug. 1998, pp. 4935-4946, vol. 18, No. 8.
Mamiko Matsutani et al., "Reconstitution reveals the functional core of mammalian eIF3", The EMBO Journal, Jul. 25, 2007, pp. 3373-3383, vol. 26, No. 14.
Aaron K. Lefebvre et al., "Translation Initiation Factor eIF4G-1 Binds to eIF3 through the eIF3e Subunit", Journal of Biological Chemistry, Jan. 1, 2006, pp. 22917-22932, vol. 281, No. 32.

(Continued)

*Primary Examiner* — Brian J Gangle
*Assistant Examiner* — Andrea McCollum
(74) *Attorney, Agent, or Firm* — Young & Thompson

(57) ABSTRACT

The method pertains to a peptide including the amino acid sequence SEQ ID NO: 1, or a peptide including an amino acid sequence having 93%, in particular 95%, particularly 98% sequence identity homology with the sequence SEQ ID NO: 1, in order to obtain a transporter intended for the internalization of a molecule of diagnostic or therapeutic interest into the target cells.

12 Claims, 9 Drawing Sheets

(56) References Cited

OTHER PUBLICATIONS

Karen S. Browning et al., "Unified nomenclature for the subunits of eukaryotic initiation factor 3", Trends in biochemical Sciences, May 1, 2011, p. 284, vol. 26, No. 5.

Zizheng Dong et al., "Initiation factor eIF3 and regulation of mRNA translation, cell growth, and cancer", Critical Reviews in Oncology Hemotology, 2006, pp. 169-180, vol. 59, No. 3.

S. Fais et al., "The role of FAS to exrin association in FAS-mediated apoptosis", Apoptosis, An International Journal on Programmed Cell Death, Oct. 1, 2005, pp. 941-947, vol. 10, No. 5.

Sanjay Chauhan et al., "Androgen regulation of the human Ferm domain encoding gene EHM2 in a cell model of steroid-induced differentiation", Biochemical and Biophysical Research Communications, 2003, pp. 421-432, vol. 310, No. 2.

Ssong-Taek Lim et al., "FERM control of FAK function", Cell Cycle, Aug. 1, 2008, pp. 2306-2314, vol. 7, No. 15.

* cited by examiner (SEQ ID NO: 57)

USE OF PEPTIDES AS TRANSPORTERS INTENDED FOR THE INTERNALIZATION OF MOLECULES OF INTEREST INTO TARGET CELLS

FIELD OF THE INVENTION

The present invention relates to the use of peptides as transporters intended for the internalization of molecules of interest into target cells.

BACKGROUND OF THE INVENTION

Biodrugs, i.e. the drugs originating from biotechnologies, play an increasingly important part in the treatment of human pathologies. These biodrugs are represented by the therapeutic proteins (enzymes, growth hormones, monoclonal antibodies, growth factors, protein vaccines), nucleic acids (siRNA, DNA, oligonucleotides), peptides (PNA) and derivatives. In certain cases, they require transporters in order to be internalized into the target cells. In recent years the internalization of the therapeutic molecules has been the subject of numerous research and development projects aimed at increasing the efficiency of the internalization of transporters, their targeting of the cells and of the organs and also reducing their potential side effects.

Thus, families of transporters have been identified, firstly based on the intracellular transfer properties of the TAT protein of the HIV virus (Fawell, S., Seery, J., Daikh, Y., Moore, C., Chen, L. L., Pepinsky, B., and Barsoum, J. (1994) *Proc Natl Acad Sci USA* 91(2), 664-668; Vives, E., Brodin, P., and Lebleu, B. (1997) *J Biol Chem* 272(25), 16010-16017), but also penetratin originating from the third helix of the *Drosophilia Antennapedia* protein (Derossi, D., Joliot, A. H., Chassaing, G., and Prochiantz, A. (1994) *J Biol Chem* 269(14), 10444-10450), the VP22 protein of the herpes simplex virus (Elliott, G., and O'Hare, P. (1997) *Cell* 88(2), 223-233; Nishi, K., and Saigo, K. (2007) *J Biol Chem* 282(37), 27503-27517) and synthetic peptide compounds of repetitions of basic amino acids such as arginine or lysine (Matsui H, Tomizawa K, Lu Y F, Matsushita M. Curr Protein Pept Sci. (2003) April; 4(2):151-7). These natural or synthetic peptides called PTD (for Protein Transduction Domain) or CPPs (for Cell-Penetratin Peptides) have the ability to transport and transfer molecules such as peptides or nucleic acids by a cell mechanism called endocytosis. Nevertheless, the internalization by endocytosis of the therapeutic molecules can have consequences for the activity and the intracellular evolution of these molecules. In fact, it is necessary for the endocytosis vesicles to be ruptured in order to allow the therapeutic molecule to be delivered into the cell. This rupture of the membrane of the endocytosis vesicles is often carried out at an acid pH potentially leading to a modification of the structure and the activity of the therapeutic molecule associated with the transporter. On the other hand, only a small proportion of the therapeutic molecules associated with the transporters will therefore be able to escape from the endosomes in order to return to the cytoplasm reducing the effect of the molecules.

Another mechanism of internalization of the molecules into the cells consists of the formation of cellular pores. In fact, a small number of PTDs or CPPs constituted by hydrophobic amino acids (MPG, Pep-1, Pep-2, Pep-3, SSHR [Sequence Signal Hydrophobic Region derived from human FGF4 and integrin β3]) are capable of penetrating through the plasma membrane forming cellular pores. These pores, depending on their size, can thus allow the direct diffusion of the therapeutic molecule into the cytoplasm without passing through the endocytosis vesicles (Langel, Ü. (2006) *Handbook of Cell-Penetrating Peptides*, 2 Ed.; Hawiger J. Curr Opin Chem. Biol. 1999 February; 3(1):89-94; Yan Liu X, Robinson D, Veach R A, Liu D, Timmons S, Collins R D, Hawiger J., J Biol. Chem. 2000 Jun. 2; 275(22):16774-8). The formation of the pores, if too numerous or too large, can in certain cases prove harmful to the cell, leading to cytosol leakage to the extracellular matrix resulting in cell death.

Rothe and Lenormand (*Curr.t protoc. in Protein Sci.*, 54: 18,11, 1-18.11.29, 2008) describe a method for producing fusion proteins comprising a segment of the ZEBRA protein (extending from the amino acid in position 170 to the amino acid in position 222) and the EGFP protein or β-galactosidase. Said fusion proteins are capable of being internalized into HeLa cells at a concentration of 0.01 µM to 0.3 µM.

The ZEBRA protein, represented by the sequence SEQ ID NO: 42, is a transcriptional activator originating from the Epstein-Barr virus. It is a protein of 245 amino acids comprising an N-terminal transactivation domain (TAD), a DNA-binding domain (DB) and a leucine zipper type dimerization domain (DIM) (FIG. 1). The C-terminal domain of said protein interacts with the leucine zipper domain leading to the formation of a hydrophobic pocket which stabilizes the ZEBRA protein/DNA complex.

Until now, the internalization routes taken by the transport peptides, known to a person skilled in the art, such as endocytosis and macropinocytosis, require significant energy expenditure in order to produce this intracellular penetration mechanism. Furthermore, this internalization by endocytosis often results in the degradation of the transported polypeptide. Only a small fraction of the transport peptides are released into the cytosol after rupture of the endosomal membrane, allowing the transported polypeptides to exert their action at cell level. As a result, on an industrial production scale, in order to ensure the efficiency of the transduction of polypeptides of interest, it is necessary to produce a large quantity of transporter and polypeptides of interest, which sometimes requires a stringent production or purification procedure, and cannot be achieved for all types of polypeptides of interest.

As a result, there is a great need to make available a transporter intended for the internalization of molecules of interest into the target cells which, on the one hand, makes it possible to transport molecules of interest into the target cells at a low concentration with high efficiency, whilst retaining the partial or total degradation of the molecules of interest inside the target cells and, on the other hand, exhibits weak cytotoxicity vis-à-vis the target cells.

SUMMARY OF THE INVENTION

One of the purposes of the present invention is to provide new peptides as transporters intended for the internalization of molecules of interest into target cells.

Another purpose of the present invention is to provide novel combinations comprising a molecule of interest and a transporter of said molecule.

Another purpose of the present invention is to provide new fusion peptides comprising a molecule of interest and a transporter of said molecule.

Also, one of the purposes of the present invention is to provide novel pharmaceutical compositions comprising a molecule of interest and a transporter of said molecule.

As a result, the present invention relates to the use:

(i)—of a peptide comprising the amino acid sequence SEQ ID NO: 1, or of a peptide comprising an amino acid sequence having 93%, in particular 95%, particularly 98% sequence identity homology with the sequence SEQ ID NO: 1, or
(ii) of a nucleic acid encoding
a peptide comprising the amino acid sequence SEQ ID NO: 1, or
a peptide comprising an amino acid sequence having 93%, in particular 95%, particularly 98% sequence identity homology with the sequence SEQ ID NO: 1,
in order to obtain a transporter intended for the internalization of a molecule of diagnostic or therapeutic interest into the target cells, said peptide being used at a concentration less than 5 nM, advantageously less than 1 nM, more advantageously less than 0.3 nM, even more advantageously less than 0.2 nM, in particular less than 0.1 nM, particularly less than 0.05 nM, more particularly less than 0.03 nM, in particular a concentration from 0.01 to 5 nM, advantageously from 0.01 to 1 nM, more advantageously from 0.01 to 0.3 nM, even more advantageously from 0.01 to 0.2 nM, in particular from 0.01 to 0.1 nM, particularly from 0.01 to 0.05 nM, more particularly from 0.01 to 0.03 nM.

By "molecule of interest", is meant the polypeptides, nucleoside analogues, nucleic acids or any other chemical or biological molecule producing a useful effect for diagnosing or treating a disease.

More particularly, the present invention relates to the use:
(i)—of a peptide comprising the amino acid sequence SEQ ID NO: 1, or
of a peptide comprising an amino acid sequence having 93%, in particular 95%, particularly 98% sequence identity homology with the sequence SEQ ID NO: 1, or
(ii) of a nucleic acid encoding
a peptide comprising the amino acid sequence SEQ ID NO: 1, or
a peptide comprising an amino acid sequence having 93%, in particular 95%, particularly 98% sequence identity homology with the sequence SEQ ID NO: 1, in order to obtain a transporter intended for the internalization of a polypeptide of diagnostic or therapeutic interest into the target cells, said peptide being used at a concentration less than 5 nM, advantageously less than 1 nM, more advantageously less than 0.3 nM, even more advantageously less than 0.2 nM, in particular less than 0.1 nM, particularly less than 0.05 nM, more particularly less than 0.03 nM, said polypeptide of interest being chosen from:

1) the eIF3-f protein, such as the mouse eIF3-f protein represented by the sequence SEQ ID NO: 19, or the human eIF3-f protein represented by the sequence SEQ ID NO: 20, or a polypeptide having 80%, in particular 90%, particularly 95% sequence identity with an eIF3-f protein sequence, or 2) the FERM protein, such as the human FERM protein, represented by the sequence SEQ ID NO: 27, or a protein having 80%, in particular 90%, particularly 95% sequence identity with the sequence represented by the sequence SEQ ID NO: 27.

DETAILED DESCRIPTION OF THE INVENTION

The present invention is based on the demonstration of a novel protein internalization mechanism, different from endocytosis, which consists of the direct penetration of said peptide into the plasma membrane by the formation of pores. These pores are of smaller in diameter than those formed by other CPPs such as Pep-1 and its derivatives, MPG and its derivatives, CADY and its derivatives and as a result are not harmful to the cells.

Given this hitherto unknown mechanism, certain peptide fragments originating from the ZEBRA protein are capable of transporting molecules of interest, in a very large number of cell lines, with a very high efficiency, at low concentrations, as the internalization is predominantly independent of the conventional routes (endocytosis and macropinocytosis) taken by the other transport peptides such as PTD (for example: TAT, VP22, Penetratin) and CPP (for example: MPG, Pep1, Pep2).

Given that the internalization carried out by the ZEBRA protein does not require the prior internalization of endosomes, it becomes possible to carry out an internalization of polypeptides of interest at low concentrations and avoid the degradation of the polypeptides of interest during the rupture of the endosomal membranes.

The expression "transporter" denotes a molecule capable of transferring another different molecule through the cell membrane in order to allow it to penetrate into the cell.

The expression "transporter" can be replaced, in the present invention, by expressions such as "cargo" or "carrier".

The expression "the internalization of a polypeptide of interest into the target cells" denotes the transfer of a polypeptide of interest from outside a target cell to inside the latter.

The peptide represented by the sequence SEQ ID NO: 1 consists of a peptide fragment originating from the ZEBRA protein (extending from the amino acid in position 170 to the amino acid in position 220). Said peptide comprises, inter alia, the DNA-binding domain (extending from the amino acid in position 178 to the amino acid in position 194), which is a basic region, and the dimerization domain (extending from the amino acid in position 195 to the amino acid in position 219). The basic region contains inter alia, 5 lysine amino acids (K) and 4 arginine amino acids (R). The dimerization domain contains 6 leucine amino acids (L), 3 alanine amino acids (A), 3 arginine amino acids (R) and 2 lysine amino acids (K). The basic region tends to be positively charged whereas the dimerization domain tends to be constituted by hydrophobic amino acids.

The nucleic acid sequences encoding the peptide represented by the sequence SEQ ID NO: 1 or a homologous peptide as described above can be deduced from the amino acid sequences of the peptides according to the principle of genetic code degeneracy known to a person skilled in the art.

The percentage of sequence identity of peptides is determined by direct comparison of two sequences of polypeptide molecules, by determining the number of identical amino acid residues in the two sequences, then dividing it by the number of amino acid residues in the longer sequence of the two, and multiplying the result by 100.

By the efficiency of the internalization of polypeptides of interest is meant the percentage of polypeptides of interest internalized into target cells. This efficiency of internalization is based on the detection of a large number of polypeptides of interest detected in the transduced cells by means of fluorescence microscopy or by flow cytometry analysis (FACS) or by Western blot analysis after cell lysis.

The efficiency of the internalization of polypeptides of interest can be measured by flow cytometry or fluorescence microscopy according to the protocol described by Rothe and Lenormand (2008).

The use of a transporter of molecules of interest according to the invention, represented by the sequence SEQ ID NO: 1 (aa170-220), at a concentration less than 5 nM, makes it possible to increase the efficiency of the internalization of polypeptides of interest by a factor of 20 compared with the use of the complete ZEBRA protein, and by a factor of 2 compared with the use of the ZEBRA fragment described by Rothe and Lenormand (2008).

In a particular embodiment, the invention relates to the use:
(i)—of a peptide represented by the amino acid sequence SEQ ID NO: 1, or
  of a homologous peptide having 93%, in particular 95%, particularly 98% sequence identity with the sequence SEQ ID NO: 1, or
(ii) of a nucleic acid encoding
  a peptide represented by the amino acid sequence SEQ ID NO: 1, or
  a homologous peptide sequence having 93%, in particular 95%, particularly 98% sequence identity with the sequence SEQ ID NO: 1,
in order to obtain a transporter intended for the internalization of a polypeptide of diagnostic or therapeutic interest into the target cells, said peptide being used at a concentration from 0.01 to 5 nM, advantageously from 0.01 to 1 nM, more advantageously from 0.01 to 0.3 nM, even more advantageously from 0.01 to 0.2 nM, in particular from 0.01 to 0.1 nM, particularly from 0.01 to 0.05 nM, more particularly from 0.01 to 0.03 nM, said polypeptide of interest being chosen from:
1) the eIF3-f protein, such as the mouse eIF3-f protein represented by the sequence SEQ ID NO: 19, or the human eIF3-f protein represented by the sequence SEQ ID NO: 20, or a polypeptide having 80%, in particular 90%, particularly 95% sequence identity with the sequence of an eIf-f protein, or
2) the FERM protein, such as the human FERM protein, represented by the sequence SEQ ID NO: 27, or a protein having 80%, in particular 90%, particularly 95% sequence identity with the sequence represented by the sequence SEQ ID NO: 27.

In another particular embodiment, the invention relates to the use:
(i)—of a peptide represented by the amino acid sequence SEQ ID NO: 55, or
  of a homologous peptide having 93%, in particular 95%, particularly 98% sequence identity with the sequence SEQ ID NO: 55, or
(ii) of a nucleic acid encoding
  a peptide represented by the amino acid sequence SEQ ID NO: 55, or
  a homologous peptide sequence having 93%, in particular 95%, particularly 98% sequence identity with the sequence SEQ ID NO: 55,
in order to obtain a transporter intended for the internalization of a polypeptide of diagnostic or therapeutic interest into the target cells, said peptide being used at a concentration from 0.01 to 5 nM, advantageously from 0.01 to 1 nM, more advantageously from 0.01 to 0.3 nM, even more advantageously from 0.01 to 0.2 nM, in particular from 0.01 to 0.1 nM, particularly from 0.01 to 0.05 nM, more particularly from 0.01 to 0.03 nM, said polypeptide of interest being chosen from:
1) the eIF3-f protein, such as the mouse eIF3-f protein represented by the sequence SEQ ID NO: 19, or the human eIf3f protein represented by the sequence SEQ ID NO: 20, or a polypeptide having 80%, in particular 90%, particularly 95% sequence identity with the sequence of an eIF3-f protein, or
2) the FERM protein, such as the human FERM protein, represented by the sequence SEQ ID NO: 27, or a protein having 80%, in particular 90%, particularly 95% sequence identity with the sequence represented by the sequence SEQ ID NO: 27.

The sequence SEQ ID NO: 55 corresponds to the segment of the ZEBRA protein extending from the amino acid in position 140 to the amino acid in position 245.

In another particular embodiment, the invention relates to the use:
(i)—of a peptide represented by the amino acid sequence SEQ ID NO: 56, or
  of a homologous peptide having 93%, in particular 95%, particularly 98% sequence identity with the sequence SEQ ID NO: 56, or
(ii) of a nucleic acid encoding
  a peptide represented by the amino acid sequence SEQ ID NO: 56, or
  a homologous peptide sequence having 93%, in particular 95%, particularly 98% sequence identity with the sequence SEQ ID NO: 56,
in order to obtain a transporter intended for the internalization of a polypeptide of diagnostic or therapeutic interest into the target cells, said peptide being used at a concentration from 0.01 to 5 nM, advantageously from 0.01 to 1 nM, more advantageously from 0.01 to 0.3 nM, even more advantageously from 0.01 to 0.2 nM, in particular from 0.01 to 0.1 nM, particularly from 0.01 to 0.05 nM, more particularly from 0.01 to 0.03 nM, said polypeptide of interest being chosen from:
1) the eIF3-f protein, such as the mouse eIF3-f protein represented by the sequence SEQ ID NO: 19, or the human eIf3f protein represented by the sequence SEQ ID NO: 20, or a polypeptide having 80%, in particular 90%, particularly 95% sequence identity with the sequence of an eIF3-f protein, or
2) the FERM protein, such as the human FERM protein, represented by the sequence SEQ ID NO: 27, or a protein having 80%, in particular 90%, particularly 95% sequence identity with the sequence represented by the sequence SEQ ID NO: 27.

The sequence SEQ ID NO: 56 corresponds to the segment of the ZEBRA protein extending from the amino acid in position 170 to the amino acid in position 245.

A polypeptide of interest can be linked to a transporter according to the invention by a covalent or non-covalent bond, such as an ionic bond, a hydrogen bond, or a hydrophobic bond.

In particular, the polypeptide of interest can be also linked to a transporter by a conventional biological linker, such as GSGG, or a conventional cross-linking agent, such as SMCC (succinimidyl 4-(N-maleimidomethyl)cyclohexane-1-carboxylate), SPDP (N-succinimidyl 3-(2-pyridyldithio)propionate).

According to the invention, a polypeptide of interest can be linked to the N-terminal or C-terminal end of a transporter, providing that the biological properties of said polypeptide of interest are not modified.

In an advantageous embodiment of the invention, said polypeptide of interest can be chosen from:
(1) the eIF3-f protein, such as the mouse eIF3-f protein represented by the sequence SEQ ID NO: 19, or the human eIF3-f protein represented by the sequence SEQ ID NO: 20, or a polypeptide having 80%, in particular 90%, particularly 95% sequence identity with the sequence of an eIF3-f protein, or
(2) the FERM protein, such as the human FERM protein, represented by the sequence SEQ ID NO: 27, or a protein having 80%, in particular 90%, particularly 95% sequence identity with the sequence represented by the sequence SEQ ID NO: 27.

The polypeptides of interest capable of being internalized by the transporter according to the invention can also be:

(1) the SPEEDY protein, such as the *Xenopus* SPEEDY protein represented by the sequence SEQ ID NO: 2, or (2) the cdk (cycline-dependent kinase)-binding domain of a SPEEDY protein, such as the cdk-binding domain of the human SPEEDY protein, represented by the sequence SEQ ID NO: 3, the cdk-binding domain of the mouse SPEEDY protein, represented by the sequence SEQ ID NO: 4, the cdk-binding domain of a *Xenopus* SPEEDY protein, represented by the sequence SEQ ID NO: 5, the cdk-binding domain of a *Xenopus* SPEEDY protein, represented by the sequence SEQ ID NO: 6, the cdk-binding domain of a *drosophila* SPEEDY protein, represented by the sequence SEQ ID NO: 7, or (3) a peptide having 80%, in particular 90%, particularly 95% sequence identity with the sequence of the cdk-binding domain of a SPEEDY protein, and retaining the consensus sequence of a SPEEDY protein, represented by the sequence SEQ ID NO: 8.

(4) the Cyclin E1 protein, such as rat Cyclin E1 protein, represented by the sequence SEQ ID NO: 9, or (5) the CLS (Centrosomal Localization signal)-binding domain of a Cyclin E1 protein, such as the CLS-binding domain of the rat Cyclin E1 protein, represented by the sequence SEQ ID NO: 10, the CLS-binding domain of a mouse Cyclin E1 protein, represented by the sequence SEQ ID NO: 11 or SEQ ID NO: 12, the CLS-binding domain of a human Cyclin E1 protein, represented by the sequence SEQ ID NO: 13 or SEQ ID NO:14, or (6) a peptide having 80%, in particular 90%, particularly 95% sequence identity with the sequence of the CLS-binding domain of a Cyclin E1 protein.

(7) the tristetraprolin protein (TTp), such as the mouse TTp protein represented by the sequence SEQ ID NO: 15, or the human TTp protein represented by the sequence SEQ ID NO: 16, or (8) a polypeptide having 80%, in particular 90%, particularly 95% sequence identity with the sequence of a TTp protein.

(9) the Atrogin or MAFbx protein, such as the human Atrogin protein represented by the sequence SEQ ID NO: 17, or the mouse F-box 32 protein, represented by the sequence SEQ ID NO: 18, or

(10) a polypeptide having 80%, in particular 90%, particularly 95% sequence identity with the sequence of an Atrogin or MAFbx protein.

(11) the MDA-7 or IL-24 protein, such as the human MDA-7 protein represented by the sequence SEQ ID NO: 21, or the mouse MDA-7 protein represented by the sequence SEQ ID NO: 22, or a variant of the human MDA-7 protein (IL-24), represented by the sequence SEQ ID NO: 23, or

(12) a polypeptide having 80%, in particular 90%, particularly 95% sequence identity with the sequence of a MDA-7 protein.

(13) the vascular endothelial-cadherin protein, such as the human vascular endothelial-cadherin protein represented by the sequence SEQ ID NO: 24, or

(14) the peptide originating from vascular endothelial-cadherin, represented by the sequence SEQ ID NO: 25, in which the Y685 tyrosine is phosphorylated by src kinase,

(15) the TP53 protein, such as the human TP53 protein, represented by the sequence SEQ ID NO: 26,

(16) the PADRE-OVA protein, represented by the sequence SEQ ID NO: 28.

The PADRE (Pan-DR-epitope) protein is a CD4(+) T helper epitope, which allows an immune response of the associated antigen (here OVA) specific CD8(+) T-cell in vaccinated mice.

An abovementioned polypeptide of interest can be conjugated to the transporter according to the invention by a direct peptide bond, or by a biological linker.

An abovementioned polypeptide of interest can also be conjugated to the transporter according to the invention by a cross-linking agent providing that the biological properties of the transporter and those of the polypeptide of interest are not modified.

In an advantageous embodiment of the invention, the polypeptide of interest is linked to the transporter according to the invention by a direct peptide bond.

The transporter according to the invention can be also linked to other types of molecules of interest, such as DNA, RNA, oligonucleotides, siRNA, miRNA, antisense RNA, or peptide nucleic acids (PNA).

The nucleic acids conjugated to the transporter intended for the internalization can be used as a diagnostic probe, or as a therapeutic agent. For example, an siRNA, an miRNA or an antisense RNA can hybridize to a target gene the expression of which in a patient is to be modified.

Moreover, a molecule of interest capable of being internalized by the transporter according to the invention can be a nucleoside analogue, for example, Didanosine, Vidarabine, Cytarabine, Entricitabine, Lamivudine, Zalcitabine, Abacavir, Stavudine, Zidovudine.

The cells capable of being the target cells of an internalization process implemented by a transporter according to the invention are chosen from eukaryotic cells, in particular human cells. These human cells can be tumour cells, such as melanoma cells, breast cancer cells, glioblastoma cells, colon cancer cells, lymphoma cells. These human cells can also be normal cells including fibroblasts, epithelial cells, lymphocytes, dendritic cells, differentiated cells (muscle cells such as myotubes for example). In order to target certain cell lines, peptide sequences such as homing peptides, NLSs (nuclear localization signal), can be grafted to the transporter according to the invention.

In an advantageous embodiment, the invention relates to the use of the peptide represented by the sequence SEQ ID NO: 1, in order to obtain a transporter intended for the internalization of a polypeptide of diagnostic or therapeutic interest, as described above, into the target cells, said peptide being used at a concentration less than 5 nM, said polypeptide of interest being chosen from:

1) the eIF3-f protein, such as the mouse eIF3-f protein represented by the sequence SEQ ID NO: 19, or the human eIf3f protein represented by the sequence SEQ ID NO: 20, or a polypeptide having 80%, in particular 90%, particularly 95% sequence identity with the sequence of an eIF3-f protein, or 2) the FERM protein, such as the human FERM protein, represented by the sequence SEQ ID NO: 27, or a protein having 80%, in particular 90%, particularly 95% sequence identity with the sequence represented by the sequence SEQ ID NO: 27.

More particularly, the invention relates to the use of the peptide represented by the sequence SEQ ID NO: 1, or the sequence SEQ ID NO: 55, or the sequence SEQ ID NO: 56, in order to obtain a transporter intended for the internalization of a polypeptide of interest into the target cells, said transporter being used at a concentration from 0.01 to 5 nM, advantageously from 0.01 to 1 nM, more advantageously from 0.01 to 0.3 nM, even more advantageously from 0.01 to 0.2 nM, in particular from 0.01 to 0.1 nM, particularly from 0.01 to 0.05 nM, more particularly from 0.01 to 0.03 nM, and said polypeptide of interest being chosen from:

1) the eIF3-f protein, such as the mouse eIF3-f protein represented by the sequence SEQ ID NO: 19, or the human eIF3-f protein represented by the sequence SEQ ID NO: 20, or a polypeptide having 80%, in particular 90%, particularly 95% sequence identity with the sequence of an eIF3-f protein, or 2) the FERM protein, such as the human FERM protein, represented by the sequence SEQ ID NO: 27, or a protein having 80%, in particular 90%, particularly 95% sequence identity with the sequence represented by the sequence SEQ ID NO: 27.

The present invention also relates to a combination comprising:

a polypeptide of diagnostic or therapeutic interest, and a transporter, used at a concentration less than 5 nM, advantageously less than 1 nM, more advantageously less than 0.3 nM, even more advantageously less than 0.2 nM, in particular less than 0.1 nM, particularly less than 0.05 nM, more particularly less than 0.03 nM, in particular a concentration from 0.01 to 5 nM, advantageously from 0.01 to 1 nM, more advantageously from 0.01 to 0.3 nM, even more advantageously from 0.01 to 0.2 nM, in particular from 0.01 to 0.1 nM, particularly from 0.01 to 0.05 nM, more particularly from 0.01 to 0.03 nM, intended for the internalization of said polypeptide of interest to target cells, said transporter being a peptide comprising the amino acid sequence SEQ ID NO: 1, or a peptide comprising an amino acid sequence having 93%, in particular 95%, particularly 98% sequence identity homology with the sequence SEQ ID NO: 1, said polypeptide of interest being chosen from:

1) the eIF3-f protein, such as the mouse eIF3-f protein represented by the sequence SEQ ID NO: 19, or the human eIF3-f protein represented by the sequence SEQ ID NO: 20, or a polypeptide having 80%, in particular 90%, particularly 95% sequence identity with the sequence of an eIF3-f protein, or 2) the FERM protein, such as the human FERM protein, represented by the sequence SEQ ID NO: 27, or a protein having 80%, in particular 90%, particularly 95% sequence identity with the sequence represented by the sequence SEQ ID NO: 27.

In another particular embodiment of the invention, said transporter is a peptide comprising the amino acid sequence SEQ ID NO: 55, or a peptide comprising an amino acid sequence having 93%, in particular 95%, particularly 98% sequence identity homology with the sequence SEQ ID NO: 55.

In another particular embodiment of the invention, said transporter is a peptide comprising the amino acid sequence SEQ ID NO: 56, or a peptide comprising an amino acid sequence having 93%, in particular 95%, particularly 98% sequence identity homology with the sequence SEQ ID NO: 56.

By the expression "combination", is meant that at least one molecule of interest is linked to a transporter as described above, by any means allowing a physical interaction between the transporter and the polypeptide of interest. This means of interaction can be a covalent or non-covalent bond, such as an ionic bond, a hydrogen bond, or a hydrophobic bond.

The molecule of interest capable of being combined with the transporter according to the invention can also be polypeptides, nucleoside analogues, nucleic acids, as described above.

A polypeptide capable of being combined with the transporter according to the invention can also be an enzyme, an antibody, an antigen, a toxin, an immunomodulator, or a functional fragment of said polypeptides, for example 1) the SPEEDY protein, such as the *Xenopus* SPEEDY protein represented by the sequence SEQ ID NO: 2, or 2) the cdk (cycline-dependent kinase)-binding domain of a SPEEDY protein, such as the cdk-binding domain of the human SPEEDY protein, represented by the sequence SEQ ID NO: 3, the cdk-binding domain of the mouse SPEEDY protein, represented by the sequence SEQ ID NO: 4, the cdk-binding domain of a *Xenopus* SPEEDY protein, represented by the sequence SEQ ID NO: 5, the cdk-binding domain of a *Xenopus* SPEEDY protein, represented by the sequence SEQ ID NO: 6, the cdk-binding domain of a *drosophila* SPEEDY protein, represented by the sequence SEQ ID NO: 7, or 3) a peptide having 80%, in particular 90%, particularly 95% sequence identity with the sequence of the cdk-binding domain of a SPEEDY protein, and retaining the consensus sequence of a SPEEDY protein, represented by the sequence SEQ ID NO: 8, 4) the Cyclin E1 protein, such as the rat Cyclin E1 protein, represented by the sequence SEQ ID NO: 9, or 5) the CLS (Centrosomal Localization signal)-binding domain of a Cyclin E1 protein, such as the CLS-binding domain of the rat Cyclin E1 protein, represented by the sequence SEQ ID NO: 10, the CLS-binding domain of a mouse Cyclin E1 protein, represented by the sequence SEQ ID NO: 11 or SEQ ID NO: 12, the CLS-binding domain of a human Cyclin E1 protein, represented by the sequence SEQ ID NO: 13 or SEQ ID NO:14, or 6) a peptide having 80%, in particular 90%, particularly 95% sequence identity with the sequence of the CLS-binding domain of a Cyclin E1 protein, 7) the tristetraprolin protein (TTp), such as the mouse TTp protein represented by the sequence SEQ ID NO: 15, or the human TTp protein represented by the sequence SEQ ID NO: 16, or 8) a polypeptide having 80%, in particular 90%, particularly 95% sequence identity with the sequence of a TTp protein, 9) the Atrogin or MAFbx protein, such as the human Atrogin protein represented by the sequence SEQ ID NO: 17, or the mouse F-box 32 protein, represented by the sequence SEQ ID NO: 18, or 10) a polypeptide having 80%, in particular 90%, particularly 95% sequence identity with the sequence of an Atrogin or MAFbx protein, 11) the MDA-7 or IL-24 protein, such as the human MDA-7 protein represented by the sequence SEQ ID NO: 21, or the mouse MDA-7 protein represented by the sequence SEQ ID NO: 22, or a variant of the human MDA-7 protein (IL-24), represented by the sequence SEQ ID NO: 23, or 12) a polypeptide having 80%, in particular 90%, particularly 95% sequence identity with the sequence of a MDA-7 protein, 13) the vascular endothelial-cadherin protein, such as the human vascular endothelial-cadherin protein represented by the sequence SEQ ID NO: 24, or 14) the peptide originating from vascular endothelial-cadherin, represented by the sequence SEQ ID NO: 25, in which the Y685 tyrosine is phosphorylated by src kinase, 15) the TP53 protein, such as the human TP53 protein, represented by the sequence SEQ ID NO: 26, 16) the PADRE-OVA protein, represented by the sequence SEQ ID NO: 28.

The present invention also relates to a fusion peptide comprising a polypeptide of diagnostic or therapeutic interest and a transporter intended for the internalization of said polypeptide of interest into the target cells, said transporter being

- a peptide comprising the amino acid sequence SEQ ID NO: 1, or
- a peptide comprising an amino acid sequence having 93%, in particular 95%, particularly 98% sequence identity homology with the sequence SEQ ID NO: 1, said polypeptide of interest being chosen from:

1) the eIF3-f protein, such as the mouse eIF3-f protein represented by the sequence SEQ ID NO: 19, or the human eIF3-f protein represented by the sequence SEQ ID NO: 20, or a polypeptide having 80%, in particular 90%, particularly 95% sequence identity with the sequence of an eIF3-f protein, or 2) the FERM protein, such as the human FERM protein, represented by the sequence SEQ ID NO: 27, or a protein having 80%, in particular 90%, particularly 95% sequence identity with the sequence represented by the sequence SEQ ID NO: 27.

In another particular embodiment of the invention, said transporter is a peptide comprising the amino acid sequence SEQ ID NO: 55, or a peptide comprising an amino acid sequence having 93%, in particular 95%, particularly 98% sequence identity homology with the sequence SEQ ID NO: 55.

In another particular embodiment of the invention, said transporter is a peptide comprising the amino acid sequence SEQ ID NO: 56, or a peptide comprising an amino acid sequence having 93%, in particular 95%, particularly 98% sequence identity homology with the sequence SEQ ID NO: 56.

By "fusion peptide", is meant a recombinant or synthetic peptide containing at least two peptides, originating from two different proteins, one linked to the other directly by a peptide bond, or by a peptide linker, such as GSGG.

The polypeptide of interest can be linked to the N-terminal or C-terminal end of the transporter, providing that the biological property of the polypeptide of interest is not modified.

In a particular embodiment, in the fusion peptide according to the invention, the polypeptide of interest is fused to the N-terminal end of the transporter intended for the internalization of said polypeptide.

In another particular embodiment, in the fusion peptide according to the invention, the polypeptide of interest is fused to the C-terminal end of the transporter intended for the internalization of said polypeptide.

A polypeptide of interest capable of being included in a fusion peptide according to the invention can also be:

1) the SPEEDY protein, such as the *Xenopus* SPEEDY protein represented by the sequence SEQ ID NO: 2, or 2) the cdk (cycline-dependent kinase)-binding domain of a SPEEDY protein, such as the cdk-binding domain of the human SPEEDY protein, represented by the sequence SEQ ID NO: 3, the cdk-binding domain of the mouse SPEEDY protein, represented by the sequence SEQ ID NO: 4, the cdk-binding domain of a *Xenopus* SPEEDY protein, represented by the sequence SEQ ID NO: 5, the cdk-binding domain of a *Xenopus* SPEEDY protein, represented by the sequence SEQ ID NO: 6, the cdk-binding domain of a *drosophila* SPEEDY protein, represented by the sequence SEQ ID NO: 7, or 3) a peptide having 80%, in particular 90%, particularly 95% sequence identity with the sequence of the cdk-binding domain of a SPEEDY protein, and retaining the consensus sequence of a SPEEDY protein, represented by the sequence SEQ ID NO: 8, 4) the Cyclin E1 protein, such as the rat Cyclin E1 protein, represented by the sequence SEQ ID NO: 9, or 5) the CLS (Centrosomal Localization signal)-binding domain of a Cyclin E1 protein, such as the CLS-binding domain of the rat Cyclin E1 protein, represented by the sequence SEQ ID NO: 10, the CLS-binding domain of a mouse Cyclin E1 protein, represented by the sequence SEQ ID NO: 11 or SEQ ID NO: 12, the CLS-binding domain of a human Cyclin E1 protein, represented by the sequence SEQ ID NO: 13 or SEQ ID NO:14, or 6) a peptide having 80%, in particular 90%, particularly 95% sequence identity with the sequence of the CLS-binding domain of a Cyclin E1 protein, 7) the tristetraprolin protein (TTp), such as the mouse TTp protein represented by the sequence SEQ ID NO: 15, or the human TTp protein represented by the sequence SEQ ID NO: 16, or 8) a polypeptide having 80%, in particular 90%, particularly 95% sequence identity with the sequence of a TTp protein, 9) the Atrogin or MAFbx protein, such as the human Atrogin protein represented by the sequence SEQ ID NO: 17, or the mouse F-box 32 protein, represented by the sequence SEQ ID NO: 18, or 10) a polypeptide having 80%, in particular 90%, particularly 95% sequence identity with the sequence of an Atrogin or MAFbx protein, 11) the MDA-7 or IL-24 protein, such as the human MDA-7 protein represented by the sequence SEQ ID NO: 21, or the mouse MDA-7 protein represented by the sequence SEQ ID NO: 22, or a variant of the human MDA-7 protein (IL-24), represented by the sequence SEQ ID NO: 23, or 12) a polypeptide having 80%, in particular 90%, particularly 95% sequence identity with the sequence of a MDA-7 protein, 13) the vascular endothelial-cadherin protein, such as the human vascular endothelial-cadherin protein represented by the sequence SEQ ID NO: 24, or 14) the peptide originating from vascular endothelial-cadherin, represented by the sequence SEQ ID NO: 25, in which the Y685 tyrosine is phosphorylated by src kinase, 15) the TP53 protein, such as the human TP53 protein, represented by the sequence SEQ ID NO: 26, 16) the PADRE-OVA protein, represented by the sequence SEQ ID NO: 28.

In a more advantageous embodiment of the invention, a fusion peptide comprises the transporter represented by the sequence SEQ ID NO: 1.

In another more advantageous embodiment of the invention, a fusion peptide comprises the transporter represented by the sequence SEQ ID NO: 55.

In another more advantageous embodiment of the invention, a fusion peptide comprises the transporter represented by the sequence SEQ ID NO: 56.

In a more advantageous embodiment of the invention, one of the above-mentioned polypeptides of interest is linked directly by peptide bond to the N-terminal end of the transporter according to the invention, represented by the sequence SEQ ID NO: 1, or the sequence SEQ ID NO: 55, or the sequence SEQ ID NO: 56.

In a particularly advantageous embodiment, the fusion peptide according to the invention is chosen from:

1) the fusion peptide represented by the sequence SEQ ID NO: 48, in which the polypeptide of interest, namely the protein eIF-3f human represented by the sequence SEQ ID NO: 20, is linked directly to the N-terminal end of the transporter represented by the sequence SEQ ID NO: 1, or 2) the fusion peptide represented by the sequence SEQ ID NO: 40, in which the polypeptide of interest, namely the human FERM protein represented by the sequence SEQ ID NO: 27, is linked directly to the N-terminal end of the transporter represented by the sequence SEQ ID NO: 1.

A fusion peptide, in which a polypeptide of interest is linked directly by peptide bond to the N-terminal end of the transporter represented by the sequence SEQ ID NO: 1, can also be:

1) the fusion peptide represented by the sequence SEQ ID NO: 42, in which the polypeptide of interest is the *Xenopus* SPEEDY protein represented by the sequence SEQ ID NO: 2, or 2) the fusion peptide represented by the sequence SEQ ID NO: 43, in which the polypeptide of interest is the cdk (cycline-dependent kinase)-binding domain of the human SPEEDY protein, represented by the sequence SEQ ID NO: 3, or 3) the fusion peptide represented by the sequence SEQ ID NO: 44, in which the polypeptide of interest is the rat Cyclin E1 protein, represented by the sequence SEQ ID NO: 9, or 4) the fusion peptide represented by the sequence SEQ ID NO: 45, in which the polypeptide of interest is the CLS (Centrosomal Localization signal)-binding domain of a human Cyclin E1 protein, represented by the sequence SEQ ID NO: 13, or 5) the fusion peptide represented by the sequence SEQ ID NO: 46, in which the polypeptide of interest is the human tristetraprolin protein (TTP) represented by the sequence SEQ ID NO: 16, or 6) the fusion peptide represented by the sequence SEQ ID NO: 47, in which the polypeptide of interest is the human Atrogin protein represented by the sequence SEQ ID NO: 17, or 7) the fusion peptide represented by the sequence SEQ ID NO: 49, in which the polypeptide of interest is the human MDA-7 protein (IL24) represented by the sequence SEQ ID NO: 21, or 8) the fusion peptide represented by the sequence SEQ ID NO: 50, in which the polypeptide of interest is the human vascular endothelial-cadherin protein represented by the sequence SEQ ID NO: 24, or 9) the fusion peptide represented by the sequence SEQ ID NO: 51, in which the polypeptide of interest is the peptide originating from vascular endothelial-cadherin, represented by the sequence SEQ ID NO: 25, in which the Y685 tyrosine is phosphorylated by src kinase, or 10) the fusion peptide represented by the sequence SEQ ID NO: 52, in which the polypeptide of interest is the human TP53 protein, represented by the sequence SEQ ID NO: 26, 11) the fusion peptide represented by the sequence SEQ ID NO: 54, in which the polypeptide of interest is the PADRE-OVA protein represented by the sequence SEQ ID NO: 28.

In another more advantageous embodiment of the invention, one of the abovementioned polypeptides of interest is linked directly to the C-terminal end of the transporter according to the invention, represented by the sequence SEQ ID NO: 1, or the sequence SEQ ID NO: 55, or the sequence SEQ ID NO: 56.

In a particularly advantageous embodiment, the fusion peptide according to the invention is chosen from:

1) the fusion peptide represented by the sequence SEQ ID NO: 35, in which the polypeptide of interest, namely the human eIF-3f protein represented by the sequence SEQ ID NO: 20, is linked directly to the C-terminal end of the transporter represented by the sequence SEQ ID NO: 1, or 2) the fusion peptide represented by the sequence SEQ ID NO: 53, in which the polypeptide of interest, namely the human FERM protein represented by the sequence SEQ ID NO: 27, is linked directly to the C-terminal end of the transporter represented by the sequence SEQ ID NO: 1.

A fusion peptide, in which a polypeptide of interest is linked directly by peptide bond to the C-terminal end of the transporter represented by the sequence SEQ ID NO: 1, can also be:

1) the fusion peptide represented by the sequence SEQ ID NO: 29, in which the polypeptide of interest is the *Xenopus* SPEEDY protein represented by the sequence SEQ ID NO: 2, or 2) the fusion peptide represented by the sequence SEQ ID NO: 30, in which the polypeptide of interest is the cdk (cycline-dependent kinase)-binding domain of the human SPEEDY protein, represented by the sequence SEQ ID NO: 3, or 3) the fusion peptide represented by the sequence SEQ ID NO: 31, in which the polypeptide of interest is the rat Cyclin E1 protein, represented by the sequence SEQ ID NO: 9, or 4) the fusion peptide represented by the sequence SEQ ID NO: 32, in which the polypeptide of interest is the CLS (Centrosomal Localization signal)-binding domain of a human Cyclin E1 protein, represented by the sequence SEQ ID NO: 13, or 5) the fusion peptide represented by the sequence SEQ ID NO: 33, in which the polypeptide of interest is the human tristetraprolin protein (TTP) represented by the sequence SEQ ID NO: 16, or 6) the fusion peptide represented by the sequence SEQ ID NO: 34, in which the polypeptide of interest is the human Atrogin protein represented by the sequence SEQ ID NO: 17, or 7) the fusion peptide represented by the sequence SEQ ID NO: 36, in which the polypeptide of interest is the human MDA-7 protein (IL24) represented by the sequence SEQ ID NO: 21, or 8) the fusion peptide represented by the sequence SEQ ID NO: 37, in which the polypeptide of interest is the human vascular endothelial-cadherin protein represented by the sequence SEQ ID NO: 24, or 9) the fusion peptide represented by the sequence SEQ ID NO: 38, in which the polypeptide of interest is the peptide originating from vascular endothelial-cadherin, represented by the sequence SEQ ID NO: 25, in which the Y685 tyrosine is phosphorylated by src kinase, or 10) the fusion peptide represented by the sequence SEQ ID NO: 39, in which the polypeptide of interest is the human TP53 protein, represented by the sequence SEQ ID NO: 26, 11) the fusion peptide represented by the sequence SEQ ID NO: 41, in which the polypeptide of interest is the PADRE-OVA protein represented by the sequence SEQ ID NO: 28.

The present invention also relates to the nucleic acids encoding a fusion peptide as described above.

The present invention also relates to vectors comprising a nucleic acid encoding a fusion peptide as described above.

In a particular embodiment, the vector according to the invention also comprises the genetic means, in particular the origins of replication, the promoters, making it possible to control the expression of the abovementioned fusion proteins.

A subject of the present invention is also host cells comprising an expression vector. Said host cells can be prokaryotic cells, such as *E. coli, basillus*, in particular *basillus brevis*, or eukaryotic cells, such as yeasts, filamentous fungi, in particular *Trichoderma reesei* and *Aspergillus niger*, insect cells using the Baculoviruses, or cell lines such as CHO, HEK 293, or Cos.

A subject of the present invention is also a pharmaceutical composition comprising a polypeptide of interest and a transporter of the molecule of interest, said transporter being
 a peptide comprising the amino acid sequence SEQ ID NO: 1, or
 a peptide comprising an amino acid sequence having 93%, in particular 95%, particularly 98% sequence identity homology with the sequence SEQ ID NO: 1.
in combination with an excipient and/or a pharmaceutically acceptable vehicle, said polypeptide of interest being chosen from:
 1) the eIF3-f protein, such as the mouse eIF3-f protein represented by the sequence SEQ ID NO: 19, or the human eIF3-f protein represented by the sequence SEQ ID NO: 20, or a polypeptide having 80%, in particular 90%, particularly 95% sequence identity with the sequence of an eIF3-f protein, or
 2) the FERM protein, such as the human FERM protein, represented by the sequence SEQ ID NO: 27, or a protein having 80%, in particular 90%, particularly 95% sequence identity with the sequence represented by the sequence SEQ ID NO: 27.

In another particular embodiment of the invention, said transporter is a peptide comprising the amino acid sequence SEQ ID NO: 55, or a peptide comprising an amino acid sequence having 93%, in particular 95%, particularly 98% sequence identity homology with the sequence SEQ ID NO: 55.

In another particular embodiment of the invention, said transporter is a peptide comprising the amino acid sequence SEQ ID NO: 56, or a peptide comprising an amino acid sequence having 93%, in particular 95%, particularly 98% sequence identity homology with the sequence SEQ ID NO: 56.

The choice of a pharmaceutically acceptable vehicle is known to a person skilled in the art.

In an advantageous embodiment of a pharmaceutical composition, the molecule of interest can be chosen from the peptides, nucleoside analogues, or nucleic acids.

A transporter according to the invention can be also included in a pharmaceutical composition, which also comprises a polypeptide of interest, such as:
 1) the SPEEDY protein, such as the *Xenopus* SPEEDY protein represented by the sequence SEQ ID NO: 2, or
 2) the cdk (cycline-dependent kinase)-binding domain of a SPEEDY protein, such as the cdk-binding domain of the human SPEEDY protein, represented by the sequence SEQ ID NO: 3, the cdk-binding domain of the mouse SPEEDY protein, represented by the sequence SEQ ID NO: 4, the cdk-binding domain of a *Xenopus* SPEEDY protein, represented by the sequence SEQ ID NO: 5, the cdk-binding domain of a *Xenopus* SPEEDY protein, represented by the sequence SEQ ID NO: 6, the cdk-binding domain of a *drosophila* SPEEDY protein, represented by the sequence SEQ ID NO: 7, or
 3) a peptide having 80%, in particular 90%, particularly 95% sequence identity with the sequence of the cdk-binding domain of a SPEEDY protein, and retaining the consensus sequence of a SPEEDY protein, represented by the sequence SEQ ID NO: 8,
 4) the Cyclin E1 protein, such as the rat Cyclin E1 protein, represented by the sequence SEQ ID NO: 9, or
 5) the CLS (Centrosomal Localization signal)-binding domain of a Cyclin E1 protein, such as the CLS-binding domain of the rat Cyclin E1 protein, represented by the sequence SEQ ID NO: 10, the CLS-binding domain of a mouse Cyclin E1 protein, represented by the sequence SEQ ID NO: 11 or SEQ ID NO: 12, the CLS-binding domain of a human Cyclin E1 protein, represented by the sequence SEQ ID NO: 13 or SEQ ID NO:14, or
 6) a peptide having 80%, in particular 90%, particularly 95% sequence identity with the sequence of the CLS-binding domain of a Cyclin E1 protein,
 7) the tristetraprolin protein (TTp), such as the mouse TTp protein represented by the sequence SEQ ID NO: 15, or the human TTp protein represented by the sequence SEQ ID NO: 16, or
 8) a polypeptide having 80%, in particular 90%, particularly 95% sequence identity with the sequence of a TTp protein,
 9) the Atrogin or MAFbx protein, such as the human Atrogin protein represented by the sequence SEQ ID NO: 17, or the mouse F-box 32 protein, represented by the sequence SEQ ID NO: 18, or
 10) a polypeptide having 80%, in particular 90%, particularly 95% sequence identity with the sequence of an Atrogin or MAFbx protein,
 11) the MDA-7 or IL-24 protein, such as the human MDA-7 protein represented by the sequence SEQ ID NO: 21, or the mouse MDA-7 protein represented by the sequence SEQ ID NO: 22, or a variant of the human MDA-7 protein (IL-24), represented by the sequence SEQ ID NO: 23, or
 12) a polypeptide having 80%, in particular 90%, particularly 95% sequence identity with the sequence of a MDA-7 protein,
 13) the vascular endothelial-cadherin protein, such as the human vascular endothelial-cadherin protein represented by the sequence SEQ ID NO: 24, or
 14) the peptide originating from vascular endothelial-cadherin, represented by the sequence SEQ ID NO: 25, in which the Y685 tyrosine is phosphorylated by src kinase,
 15) the TP53 protein, such as the human TP53 protein, represented by the sequence SEQ ID NO: 26,
 16) the PADRE-OVA protein, represented by the sequence SEQ ID NO: 28.

In an advantageous embodiment, the pharmaceutical composition according to the invention comprises a fusion peptide as described above, in particular, a peptide chosen from a peptide represented by the sequence SEQ ID NO: 35, or a peptide represented by the sequence SEQ ID NO: 40.

In a particular embodiment of the invention, said pharmaceutical composition is formulated for a daily administration of 1 mg/m$^2$ to 1000 mg/m$^2$.

The administration of such a pharmaceutical composition can be carried out by oral route, by intravenous route, by parenteral route, by nasal route, by pulmonary route.

A subject of the present invention is also the use of a combination comprising:
 a molecule of diagnostic or therapeutic interest, and
 a transporter intended for the internalization of said molecule of interest into target cells,
for the preparation of a drug intended for the treatment or prevention of cancers such as melanomas, breast cancer, glioblastomas (brain tumours), colon cancer, lymphomas, said transporter being:
 a peptide comprising the amino acid sequence SEQ ID NO: 1, or
 a peptide comprising an amino acid sequence having 93%, in particular 95%, particularly 98% sequence identity homology with the sequence SEQ ID NO: 1.

More particularly, the present invention relates to the use of a fusion peptide chosen from a peptide represented by the sequence SEQ ID NO: 35, or a peptide represented by the sequence SEQ ID NO: 40, for the preparation of a drug intended for the treatment or prevention of cancers such a melanomas, breast cancer, glioblastomas (brain tumours), colon cancer, lymphomas.

BRIEF DESCRIPTION OF THE DRAWINGS

The present invention is illustrated by the following figures and examples. The examples hereafter are intended to clarify the subject-matter of the invention and illustrate advantageous embodiments, but are in no event intended to restrict the scope of the invention.

EXAMPLE 1

Figure 1A:
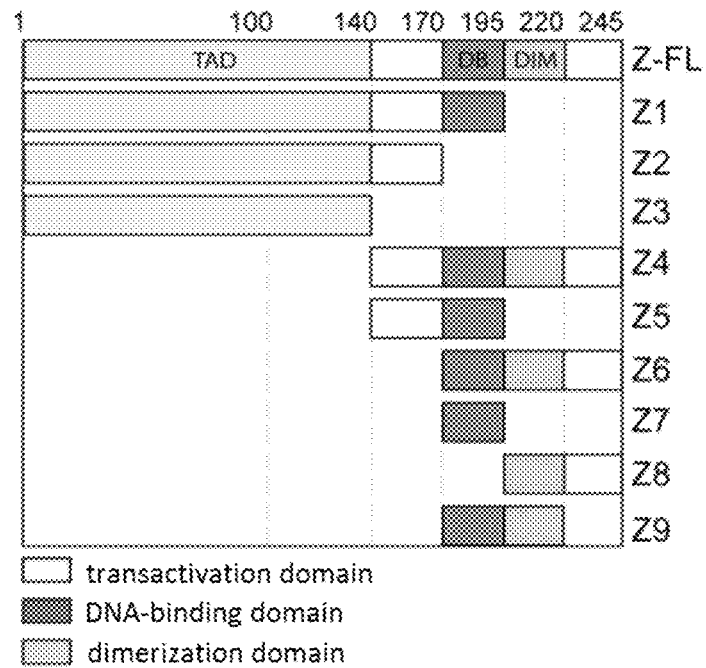
FIG. 1A shows the structure of the complete ZEBRA protein (Z-FL), as well as that of nine truncated ZEBRA protein fragments, namely Z1 (amino acids 1 to 195 of the ZEBRA protein), Z2 (amino acids 1 to 170 of the ZEBRA protein), Z3 (amino acids 1 to 140 of the ZEBRA protein), Z4 (amino acids 140 to 245 of the ZEBRA protein), Z5 (amino acids 140 to 195 of the ZEBRA protein), Z6 (amino acids 170 to 245 of the ZEBRA protein), Z7 (amino acids 170 to 195 of the ZEBRA protein), Z8 (amino acids 195 to 245 of the ZEBRA protein) and Z9 (amino acids 170 to 220 of the ZEBRA protein).

Materials and methods 1.1 Cloning of the ZEBRA Protein and its Fragments

The DNA fragments encoding the complete ZEBRA protein (Z-FL) or its fragments (Z1, Z2, Z3, Z4, Z5, Z6, Z7, Z8 and Z9) are obtained by PCR and inserted into the pET15b expression vector (Novagen) of E.coli, which makes it possible to express the peptides the N-terminal end of which is linked to a 6-histidine tag. The complete ZEBRA protein, as well as the truncated fragments, namely Z2, Z4, Z5, Z6, Z7, Z8 and Z9, are fused with EGFP (Enhanced Green Fluorescent Proteins) respectively, producing the Z-FL-EGFP, Z2-EGFP, Z3-EGFP, Z4-EGFP, Z5-EGFP, Z6-EGFP, Z8-EGFP and Z9-EGFP fusion proteins. The Z6 and Z9 fragments are also fused with β-galactosidase respectively, producing the Z6-βGal, Z9-βGal fusion proteins.

The primer sequences used for the construction of these fragments are listed in Table 1 below.

TABLE 1

| Name | 5' → 3' Sequence | Restriction site | SEQ ID NO. |
|---|---|---|---|
| Construction of complete ZEBRA | | | |
| ZebraXhoIfor | CCGCTCGAGATGATGGACCCAAACTCGAC | XhoI | SEQ ID NO: 60 |
| ZebraBamHIrev | CGCGGATCCGAAATTTAAGAGATCCTCGTG | BamHI | SEQ ID NO: 61 |
| ZebraBamHIStoprev | CGCGGATCCTTAGAAATTTAAGAGATCCTCGTG | BamHI | SEQ ID NO: 62 |
| Construction of truncated ZEBRA fragments | | | |
| ZebraAS1NdeIfor | GGAATTCCATATGGACCAAACTCGAC | NdeI | SEQ ID NO: 63 |
| ZebraAS195BamHIrev | CGCGGATCCTTATTGCTTAAACTTGGCCCGGC | BamHI | SEQ ID NO: 64 |
| ZebraAS170BamHIrev | CGCGGATCCTTATTCCTCCAGCGATTCTGGC | BamHI | SEQ ID NO: 65 |
| ZebraAS140BamHIrev | CGCGGATCCTTACTGTTGTCCTTGGTTAGCCC | BamHI | SEQ ID NO: 66 |
| ZebraAS170NdeIfor | GGAATTCCATATGCAGCTAGCAGACATTGGTGTTCC | NdeI | SEQ ID NO: 67 |
| ZebraAS195NdeIfor | GGAATTCCATATGCAACTGCTGCAGCACTACC | NdeI | SEQ ID NO: 68 |
| ZebraBamHIStoprev | CGCGGATCCTTAGAAATTTAAGAGATCCTCGTG | BamHI | SEQ ID NO: 69 |
| ZebraAS50NdeIffor | GGAATTCCATATGCCGGTGCTGCCAGAGCC | NdeI | SEQ ID NO: 70 |
| ZebraAS100NdeIfor | GGAATTCCATATGGACATAACCCAGAATCAACAG | NdeI | SEQ ID NO: 71 |
| ZebraAS50XhoIrev | CCGCTCGAGCGGCCACAGCACACAAGG | XhoI | SEQ ID NO: 72 |
| ZebraAS100XhoIrev | CCGCTCGAGTATGTCGGAGACTGGGAACAG | XhoI | SEQ ID NO: 73 |
| ZebraAS140XhoIrev | CCGCTCGAGCTGTTGTCCTTGGTTAGCCC | XhoI | SEQ ID NO: 74 |
| ZebraAS245XhoIrev | CCGCTCGAGGAAATTTAAGAGATCCTCGTG | XhoI | SEQ ID NO: 75 |
| ZebraAS195XhoIrev | CCGCTCGAGTTGCTTAAACTTGGCCCGGC | XhoI | SEQ ID NO: 76 |
| ZebraAS140XhoIrev | CCGCTCGAGCTGTTGTCCTTGGTTAGCCC | XhoI | SEQ ID NO: 77 |
| ZebraAS140NdeIfor | GGAATTCCATATGCAGCTAGCAGACATTGGTGTTCC | NdeI | SEQ ID NO: 78 |
| ZebraAS195NdeIfor | GGAATTCCATATGCAACTGCTGCAGCACTACC | NdeI | SEQ ID NO: 79 |
| ZebraAS170NdeIfor | GGAATTCCATATGGAGGAATGCGATTCTGAACTAG | NdeI | SEQ ID NO: 80 |
| ZebraAS220XhoIrev | CCGCTCGAGGCACATCTGCTTCAACAGG | XhoI | SEQ ID NO: 81 |
| ZebraAS100XhoIrev | CCGCTCGAGTATGTCGGAGACTGGGAACAG | XhoI | SEQ ID NO: 82 |
| ZebraAS175NdeIfor | GGAATTCCATATGAAGCGATACAAGAATCGGGTGGC | NdeI | SEQ ID NO: 83 |
| GFP fusion protein | | | |
| GFPNdeIfor | GGA ATTCCATATGGTGAGCAAGGGCGAGGA | NdeI | SEQ ID NO: 84 |
| GFPXhoIrev | CCGCTCGAGCTTGTACAGCTCG | XhoI | SEQ ID NO: 85 |
| GFPXhoIfor | CCGCTCGAGATGGTGAGCAAGGGCGAG | XhoI | SEQ ID NO: 86 |
| GFPBamHIrev | CGCGGATCCCTTGTACAGCTCGTCCATGC | BamHI | SEQ ID NO: 87 |

TABLE 1-continued

| Name | 5' → 3' Sequence | Restriction site | SEQ ID NO. |
|---|---|---|---|
| LacZ fusion protein | | | |
| lacZXhoIfor | CCG<u>CTCGAG</u>ATGATTACGGATTCACTGGCCGTCGTTTTACAACGTCG | XhoI | SEQ ID NO: 88 |
| LacZBamHIrev | CGC<u>GGATCC</u>TTTTTGACACCAGACCAACTGG | BamHI | SEQ ID NO: 89 |
| MDA7 fusion protein | | | |
| Mda7 N (D1) | TAACGC<u>CTCGAG</u>AATTTTCAACAGAGGCTGCAAAG | XhoI | SEQ ID NO: 90 |
| Mda7 N (R1 | ATTCTTAT<u>GGATCC</u>TTTAGAGCTTGTAGATTTT?TGCATCC | BamHI | SEQ ID NO: 91 |
| MDA7AS51XhoIfor | CCG<u>CTCGAG</u>GGCCAAGAATTCCACTTTGG | XhoI | SEQ ID NO: 92 |
| eIF3 fusion protein | | | |
| eIF3-N (D1) | TAACGC<u>CTCGAG</u>GCCACACCGGCGGTACCAGTAAGTGCTCCTCCG | XhoI | SEQ ID NO: 93 |
| eIF3-N (R1) | ATTCTTAT<u>GGATCC</u>TTACAGGTTTACAAGTTTTTCATTG | BamHI | SEQ ID NO: 94 |

1.2 Expression and Purification of Recombinant Proteins

The recombinant fusion proteins are expressed in the BL21 line (DE3) of E.coli, after induction with 0.5 mM IPTG for 15 h at 16° C. The cells are lysed by sonication in 20 mM of Tris buffer at pH 6.8 to 8, containing 250 mM of NaCl and 10% glycerol. The lysed cells are then treated with DNase I (Roche) in order to remove the nucleic acids. The purification of the proteins possessing an His6 tag is carried out by nickel affinity chromatography. The proteins are rinsed with an NaCl gradient of 0.5 to 1.5 M and eluted with a buffer containing 500 mM of imidazole, 20 mM of Tris, 75 mM of KCl, 0.5 M of NaCl and 10% glycerol. All the purification stages are carried out at 4° C. and in the presence of the protease inhibitors (Pepstatin, E-64, Aprotinin, Pefablock and the complete protease inhibitor mix, Roche). Before the transduction experiments, the purified proteins are dialysed against PBS (phosphate buffered saline).

1.3 Culture Medium and Transduction Experiments

The HeLa, Saos-2, C2C12 cell lines are utilized in the transduction experiments. The HeLa cells are maintained in DMEM culture medium (Dulbecco's Modified Eagle Medium) (Gibco), and the Saos-2 cells are maintained in the "MaCoy's 5A" culture medium (Gibco) completed with 50 U/ml of penicillin, 50 µg/ml of streptomycin and 2 mM of L-glutamine (Gibco), and 10-20% of the foetal calf serum inactivated at high temperature (Gibco). $7.5 \times 10^5$ cells per well are seeded on a 12-well plate 24 h before the transduction experiments. For microscopic analysis, the cells ($2.5 \times 10^5$) are plated in a 4-well culture chamber at least 24 h before the operation.

The internalization experiments are carried out at 60-80% confluence. The cells are rinsed twice with phosphate buffered saline before the addition of fresh culture medium devoid of serum. The culture medium contains the indicated quantity of proteins. 4 hours later, the culture medium is completed with foetal calf serum inactivated at high temperature (Gibco) for long-term incubation.

1.4 Immunocytochemistry and Fluorescence Microscopy

During the incubation of cells with the proteins fused to EGFP, the cells are rinsed with PBS, then subjected to moderate trypsinization (0.5% trypsin-EDTA) and several rinses with heparin (20 µg/ml) in PBS and fixed for 10 minutes in 4% PFA at ambient temperature. The cells are permeabilized and blocked with 0.25% and 5% BSA in PBS for 1 h at ambient temperature, and then incubated for 1 h at ambient temperature in a PBS buffer containing 0.1% TRITON™ X-100 and 5% BSA with a corresponding primary antibody. In order to detect the endosomal proteins, an anti-EEA1 antibody (4 µg/ml, Calbiochem), an anti-Rab7 antibody (5 µg/ml, Cell Signalling), an anti-clathrin or an anti-caveloelin-1 antibody (5 µg/ml, Santa Cruz Biotechnology) are used respectively. After three 10-minute rinses with PBS, the cells are incubated with a corresponding secondary antibody, namely anti-mouse ALEXA FLUOR® 555 and anti-rabbit ALEXA FLUOR® 647 (Molecular Probes), in a buffer containing 0.4% TRITON™ X-100 and 5% BSA. The cells are rinsed 5 times for 10 minutes with PBS and the nuclei are stained with Hoechst 33258 (Molecular Probes). The cell fluorescence on the unfixed cells is visualized using a fluorescence microscope (Nikon Eclipse TE2000-E) equipped with a GFP filter (465 to 495 nm excitation and 515 to 555 nm emission).

In order to study the localization of the fusion proteins in cells, confocal microscopy (TCS-SP2-Leica Manheim, Germany) is used. The images are acquired sequentially, with 488 nm excitation for Z9-EGFP (collection of fluorescence between 500 and 540 nm, displayed in green), 633 nm excitation for ALEXA FLUOR® 647 coupled with an anti-EEA1, an anti-Rab7, an anti-clathrin or an anti-caveloelin-1 (collection of fluorescence between 650 and 700 nm, displayed in red), and excitation at 405 nm for Hoechst (collection of fluorescence between 415 and 460 nm, displayed in blue).

1.5 Western Blot Analysis

After the transduction experiments, the cells are collected and the non-internalized proteins are removed by trypsinization. The complete extracted cell is prepared by lysis of mammal cells in the lysis buffer (Sigma) at 0° C. The cytosolic and nuclear fractions are separated with a cell compartmentalization kit (Pierce). The primary antibodies are respectively a mouse anti-ZEBRA Z125/Z130 monoclonal antibody and a mouse anti-GFP monoclonal antibody (Euromedex). After incubation with a mouse secondary antibody (Amersham) labelled with peroxidase, the membrane is rinsed and then analyzed by an advanced chemiluminescence detection system (Amersham).

1.6 Flow Cytometry Analysis

The cells are treated with 0.5% trypsin and 20 µg/ml of heparin for 10 minutes in order to remove proteins bound to the surface of cells before the green fluorescence analysis.

Only the living cells are analyzed and the dead cells are removed by Amino-Actinomycin D (7-AAD). The flow cytometry is implemented by the FACS (fluorescence-activated cell sorting) technique (Becton Dickinson).

1.7 DNA Retardation Gel Experiment (Electrophoretic mobility Shift Assay (EMSA))

The EMSA technique is implemented by the AP-1 probe, constituted by two hybridized oligonucleotides (5'-AGCACTGACTCATGAAGT-3' (SEQ ID NO: 58) and 5'-TACTTCATGAGTCAGTGCT-3' (SEQ ID NO: 59)). The cold probe is labelled with biotin and purified using a mini-column (MICROSPIN™ G-25, Active Motif). Up to 500 µg of the complete ZEBRA protein or its fragments are pre-incubated for 15 minutes on ice with 4× binding buffer B-1, 2× stabilizing buffer (Generka) and 1 mM of DTT. The biotin-labelled probe is mixed with 4× binding buffer C-1, 2× stabilizing buffer (Generka) and 50 ng/µl of poly (dI-dC) and added to the solution containing the proteins. After incubation of the reaction mixture for 15 minutes at 4° C., the samples are separated on non-denaturing polyacrylamide gel in 0.5×TBE buffer and then transferred to a Hybond™ H+ nylon membrane (Amersham). The presence of the bands is detected by the kit (LightShift Chemiluminescent EMSA Kit, Pierce).

1.8 Cytotoxicity Measurement

The integrity of the membrane is measured with the cytotoxicity detection kit (Roche Applied Science). $1×10^4$ HeLa or Saos2 cells are seeded in the 96-well plates 24 h before the treatment with Z9, in a culture medium without serum, at the concentrations indicated by the manufacturer. After treatment for 24 h, the measurement is implemented using lactic dehydrogenase according to the protocol supplied by the manufacturer.

1.9 Treatment with Chemical Products

Heparin, as well as the endocytotic inhibitors such as wortmannin, nystatin, chlorpromazine hydrochloride and methyl-3-cyclodextrin (MβCD), 2-deoxy-D-glucose and sodium azide, are bought from Sigma. Before the addition of Z9-EGFP, the cells are first incubated for 30 minutes in a culture medium without serum containing one of the products mentioned above, in an indicated concentration (20 µg/ml of heparin, 100 nM of wortmannin, 50 µg/ml of nystatin, 30 µM of chlorpromazine hydrochloride and 5-10 mM of methyl-β-cyclodextrin (MβCD)). The cells are then incubated for 3 hours at 37° C. or 4° C. in the presence of inhibitors and Z9-EGFP. Before fluorescence analysis by flow cytometry, the cells are incubated with 0.5% of trypsin-EDTA, in order to remove the proteins bound to the surface of cells. In order to exhaust the ATP reserve, the cells are pre-incubated for 1 hour in PBS containing 6 mM of 2-deoxy-D-glucose and 10 mM of sodium azide.

1.10 Detection of β-Galactosidase

After the transduction experiments, the cells are rinsed with 20 ng/ml of heparin in PBS, and treated with trypsin in order to remove the proteins bound to the surface of cells. The fixing and the detection are carried out according to the kit protocol (β-galactosidase Reporter Gene Staining Kit (Sigma)). The cells are incubated for 10 minutes at ambient temperature with 1× fixing solution, containing 2% formaldehyde and 0.2% glutaraldehyde. After three stages of rinsing with PBS at ambient temperature, the cells are revealed by a solution containing 20 mM of $MgCl_2$, 40 mM of potassium ferricyanide and 2 mg/mL of β-galactosidase, for 3 hours at 37° C. The images are captured by phase contrast microscopy (Nikon Eclipse TE2000-E).

1.11 Internalization of Cells by DNA/Z9 Complexes

The complexes formed between the siRNA or plasmid DNA or peptide nucleic acid (PNA) are produced by mixing 1 to 500 nmol/L of siRNA re-suspended in water or plasmid DNA or PNA with corresponding concentrations of Z9 from 1 to 40000 nmol/L in order to obtain siRNA/Z9 ratios ranging from 1/1 to 1/5, 1/10, 1/15, 1/20, 1/40, 1/60, 1/80. The Z9 peptide is re-suspended in PBS containing 10% glycerol and mixed with the siRNA at the concentrations indicated above. The Z9/nucleic acids mixtures are incubated on mammalian cells for 1 to 6 hours, then the cells are washed in order to remove the excess of Z9/nucleic acids and fresh medium is added to the cells.

EXAMPLE 2

Results 2.1 Identification of the ZEBRA Minimal Domain

The ZEBRA protein comprises three main domains: an N-terminal trans-activation domain (TAD, residues 1-140), a DNA-binding domain (DB, residues 175-195), a dimerization domain (DIM, residues 195-220) of the leucine zipper type. In order to identify the ZEBRA minimal domain required to carry out an internalization in a mammalian cell line, nine different deletion mutants of the complete ZEBRA protein (Z-FL) were constructed by the Inventors. These nine mutants are the deletion mutant Z1 comprising the TAD domains, the linker and DB (amino acids 1 to 195), the deletion mutant Z2 comprising the TAD domains and the linker (amino acids 1 to 170), the deletion mutant Z3 comprising only the TAD domain (amino acids 1 to 140), the deletion mutant Z4 comprising the linker, DB, DIM and the C-terminal domains (amino acids 140 to 245), the deletion mutant Z5 comprising the linker and DB domains (amino acids 140 to 195), the deletion mutant Z6 comprising the DB, DIM and C-terminal domains (amino acids 170 to 245), the deletion mutant Z7 comprising the DB domain (amino acids 170 to 195), the deletion mutant Z8 comprising the DIM and C-terminal domains (amino acids 195 to 245) and the deletion mutant Z9 comprising the DB and DIM domains (amino acids 170 to 220) (FIG. 1A).

Figure 1B:
FIG. 1B shows the expression of the complete ZEBRA protein (Z-FL) and its Z1, Z2, Z3, Z4, Z5, Z6, Z7 and Z8 fragments in $E.coli$ BL21 (DE3). The proteins are purified by nickel affinity chromatography, and separated by SDS-PAGE, then detected by Western blot using the anti-His antibody.

The complete ZEBRA protein (Z-FL) as well as its fragments (Z2, Z3, Z4, Z5, Z6, Z7 and Z8) are overexpressed in E.coli (FIG. 1B) and then purified according to the method described in section 1.2 above.

In order to determine the transduction capacity of these ZEBRA fragments, the Z2, Z3, Z4, Z5, Z6, Z8 and Z9 fragments are fused with EGFP (Enhanced Green Fluorescent Proteins).

Figure 1C:
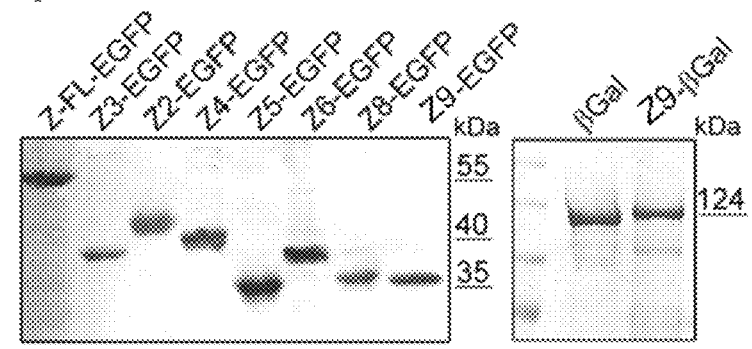
FIG. 1C shows the expression of the Z-FL-EGFP, Z2-EGFP, Z3-EGFP, Z4-EGFP, Z5-EGFP, Z6-EGFP, Z8-EGFP, Z9-EGFP and Z9-βGal fusion proteins in $E.coli$ BL21 (DE3). The proteins are separated by 13% SDS PAGE and detected by staining with Coomassie blue.

The EGFP fusion proteins are also overexpressed (FIG. 1C) and then purified according to the method described in section 1.2 above.

Figure 1D:
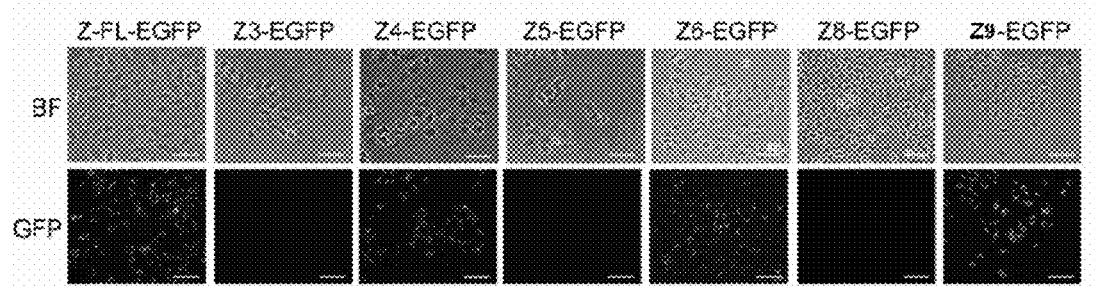
FIG. 1D shows the intracellular fluorescence emitted by the living HeLa cells after incubation for 15 hours respectively with 0.2 μM of Z-FL-EGFP, Z2-EGFP, Z3-EGFP, Z4-EGFP, Z5-EGFP, Z6-EGFP, Z8-EGFP and Z9-EGFP. The fluorescence emitted by cells is observed by fluorescence microscopy. The photos in the top line represent, for each of the fusion proteins, the visualization of living cells before the transduction carried out by the complete ZEBRA protein or before that by different truncated ZEBRA fragments. The photos in the bottom line represent, for each of the fusion proteins, the visualization of cells after the internalization of the different fusion proteins indicated.
Figure 1E:
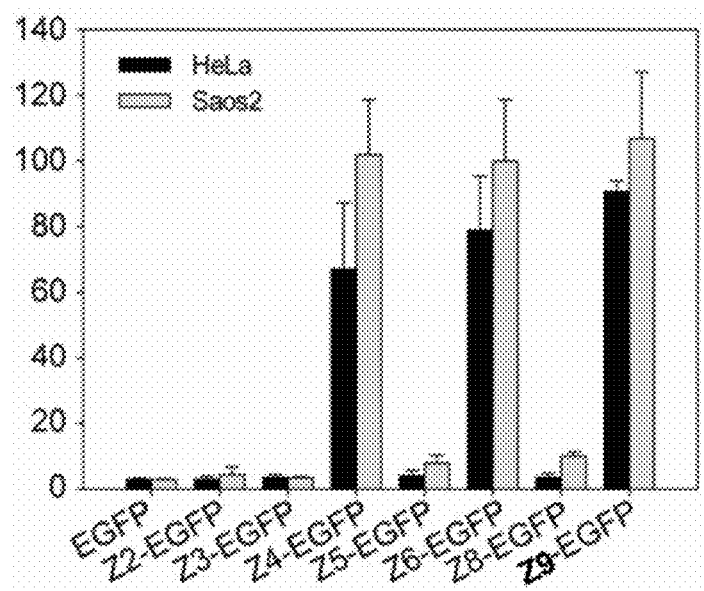
FIG. 1E shows the analysis of the HeLa and Saos2 cells by flow cytometry. The cells are incubated respectively with 0.2 μM of Z-FL-EGFP, Z2-EGFP, Z3-EGFP, Z4-EGFP, Z5-EGFP, Z6-EGFP, Z8-EGFP and Z9-EGFP, and then treated with trypsin before the FACS analysis. The mean fluorescence intensity is obtained from three independent experiments.
Figure 1F:
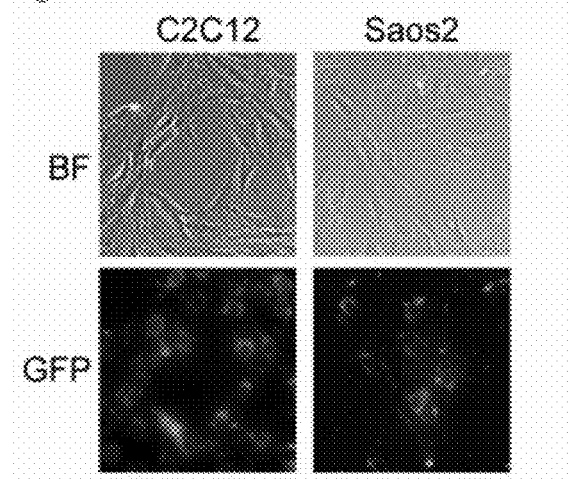
FIG. 1F shows the accumulation of Z9-EGFP in the C2C12 and Saos2 cells. 0.2 μM of Z9-EGFP is added to the culture medium without serum. The intracellular fluorescence is visualized by florescence microscopy. The photos in the top line represent for each of the cell lines the visualization of living cells before the transduction carried out by the Z9-EGFP fragment. The photos in the bottom line represent respectively the visualization of cells after the internalization of the different fusion proteins indicated.

The fusion proteins are added to the culture medium containing a cervical cancer (HeLa) or osteosarcoma (Saos2) cell line. After incubating for 24 h, the fluorescence emitted by the unfixed living cells is detected by flow cytometry or by fluorescence microscopy. Only the constructions Z-FL-EGFP, Z4-EGFP, Z6-EGFP and Z9-EGFP can be internalized inside HeLa cells (FIG. 1D). No fluorescent signal is detected in the cells incubated with the Z3-EGFP fragment, which contains only the N-terminal end of natural ZEBRA, or the Z5-EGFP fragment, which does not contain the dimerization domain, or the Z8-EGFP fragment, which does not contain the basic domain. The efficiency of internalization carried out by the Z2, Z3, Z4, Z5, Z6, Z8 and Z9 fragments is also evaluated in the HeLa and Saos2 cell lines by flow cytometry after incubation for 15 h. This method confirms the internalization of Z4-EGFP, Z6-EGFP and Z9-EGFP into the two cell lines (FIG. 1E). Furthermore, the internalization of Z9-EGFP into mouse myoblasts (C2C12) and the Saos2 cell line is observed by fluorescence microscopy (FIG. 1F).

These results mean that the presence of the DNA-binding domain (BD) and of the dimerization domain (DIM) is indispensable and sufficient to carry out the internalization. The minimal domain for carrying out an internalization of peptide is the Z9 mutant, comprising the DB and DIM domains, which makes it possible to carry out an internalization of polypeptides into the target cells with almost 100% efficiency.

2.2 DNA-Binding Capacity

Figure 2:
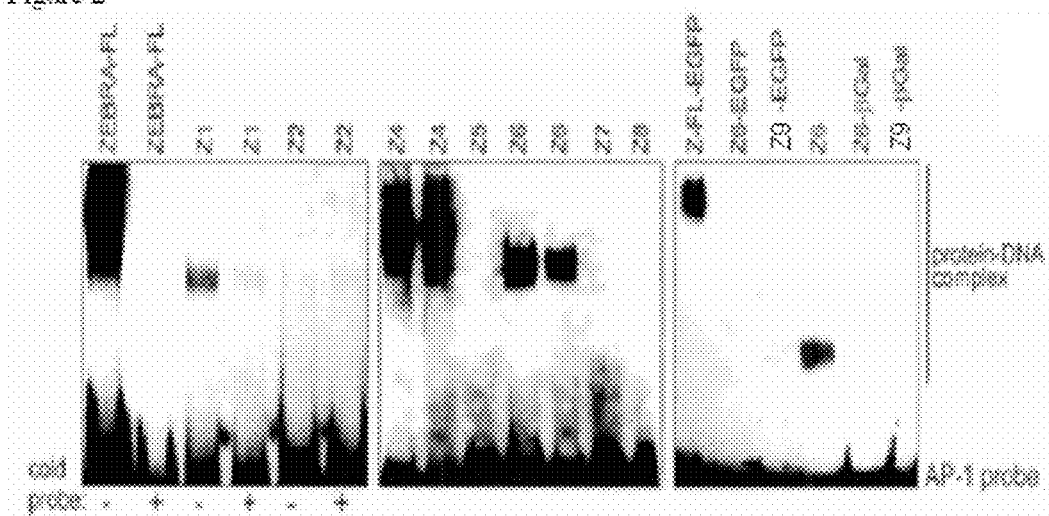
FIG. 2 shows the result of the DNA retardation gel experiment. The different truncated fragments of the ZEBRA protein and the fusion proteins, namely Z-FL-EGFP, Z6-EGFP, Z9-EGFP, Z6-βGal, Z9-βGal, are analyzed for their capacity to bind to the DNA AP-1 probe. The signals are detected by Chemiluminescent Assay (Pierce).

Given that the ZEBRA protein is a transcription factor which is bound to the DNA by its DNA-binding domain (residues of 175 to 195 aa), the DNA-binding capacity of different fragments of the ZEBRA protein is analyzed by the DNA retardation gel technique (Electrophoretic mobility shift assay). It is already known that ZEBRA recognizes the consensus heptamer TGA G/C TCA, which can bind to AP-1 (activator protein). This heptamer is used in the invention as a probe to evaluate the DNA-binding capacity. FIG. 3 shows that the Z4 and Z6 fragments, which include both the DNA-binding domain and the dimerization domain can bind to the probe with an efficiency almost equal to that of the total ZEBRA protein. The Z8 fragment, which contains only the DIM domain, the Z5 and Z7 fragments, which contain only the DB domain, or the Z2 and Z3 fragments, which contain neither the DIM domain, nor the DB domain, cannot bind to the probe (FIG. 2).

These results confirm that the presence of the DNA-binding domain (BD) and of the dimerization domain (DIM) is indispensable and sufficient to achieve a bond to the DNA.

On the other hand, no fusion protein analyzed in this experiment (Z6-EGFP, Z9-EFGP, Z6-βGal, Z9-βGal) exhibits any DNA-binding capacity.

2.3 Z9-EGFP Internalization Kinetics

Figure 3A:
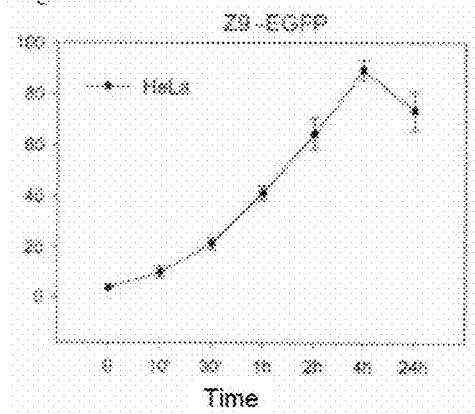
FIG. 3A shows the time-dependent intracellular internalization of Z9-EGFP into the HeLa cells. The cells are incubated for 10 minutes, 30 minutes, 1 hour, 2 hours, 4 hours and 24 hours respectively, with 0.2 μM of Z9-EGFP at 37° C. The cells are then treated with trypsin for 10 minutes at 37° C. The mean cell fluorescence is analyzed by flow cytometry. The X-axis represents the incubation time of cells with Z9-EGFP. The Y-axis represents the mean cell fluorescence.
Figure 3B:
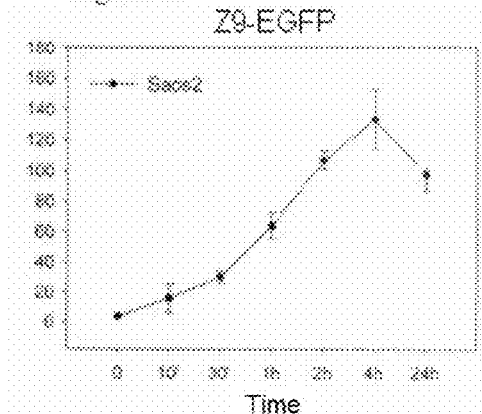
FIG. 3B shows the time-dependent intracellular internalization of Z9-EGFP into the Saos2 cells. The cells are incubated for 10 minutes, 30 minutes, 1 hour, 2 hours, 4 hours and 24 hours respectively, with 0.2 μM of Z9-EGFP at 37° C. The cells are then treated with trypsin for 10 minutes at 37° C. The mean cell fluorescence is analyzed by flow cytometry. The X-axis represents the incubation time of cells with Z9-EGFP. The Y-axis represents the mean cell fluorescence.

The translocation of Z9-EGFP is monitored by measuring the fluorescence in the living cells by flow cytometry. The addition of a low concentration of Z9-EGFP (0.2 µM) to the culture medium without serum of HeLa or Saos2 cells leads to a rapid intracellular accumulation of fusion proteins (FIGS. 3A and 3B). After the removal of the proteins binding to the surface of cells with trypsin/heparin, these signals are detected, and remain stable for at least 24 hours (FIGS. 3A and 3B). The increase in the fluorescence intensity in the Saos2 cells after the transduction is due rather to the large size of these cells relative to that of the HeLa cells, but not to a better efficiency of translocation in the former.

Figure 3C:
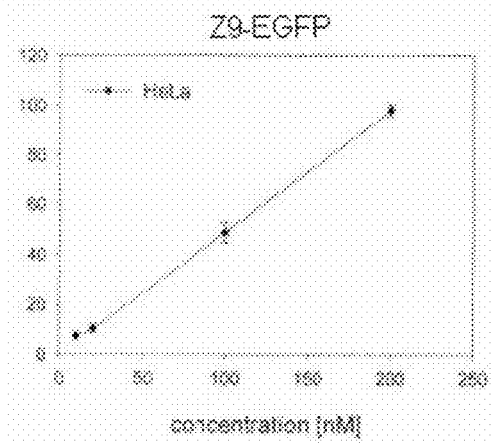
FIG. 3C shows the dose-dependent intracellular internalization of Z9-EGFP into the HeLa cells. Z9-EGFP at different concentrations (10, 20, 100, 200 nM) is added respectively to the culture medium without serum. After incubation for 4 hours, the cells are rinsed with PBS, and then treated with trypsin for 10 minutes at 37° C. The cell fluorescence is measured by flow cytometry. All the transduction experiments are carried out in triplicate. The X-axis represents the cell concentration (nM). The Y-axis represents the percentage of EGFP-positive cells.
Figure 3D:
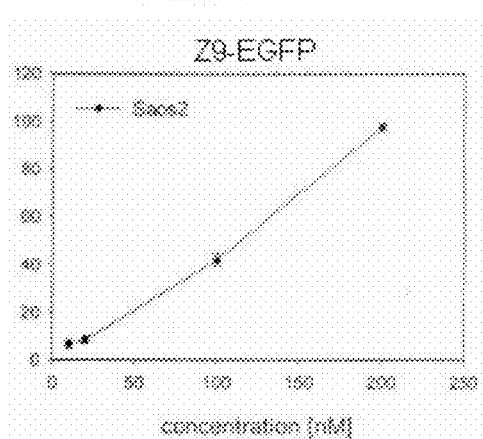
FIG. 3D shows the dose-dependent intracellular internalization of Z9-EGFP into the Saos2 cells. Z9-EGFP at different concentrations (10, 20, 100, 200 nM) is added respectively into the culture medium without serum. After incubation for 4 hours, the cells are rinsed with PBS, and then treated with trypsin for 10 minutes at 37° C. The cell fluorescence is measured by flow cytometry. All the transduction experiments are carried out in triplicate in two independent experiments. The X-axis represents the cell concentration (nM). The Y-axis represents the percentage of EGFP-positive cells.

The dose-dependent intracellular internalization of Z9-EGFP into the cells is analyzed in the HeLa and Saos2 cells. The cells are incubated for 4 hours with the different concentrations of Z9-EGFP (10, 20 100 and 200 nM) (FIGS. 3C and 3D).

The cell internalization of Z9-EGFP is characterized by the imaging of living cells. 0.3 µM of ZEBRA-EGFP is added to the HeLa cells and visualized directly by fluorescence microscopy over 1 hour. The rapid accumulation of EGFP signals in the cell membranes can be observed as from the first 15 minutes. Then the EGFP signals are transported rapidly inside cells.

2.4 Z9-EGFP Cytotoxicity

Figure 3E:
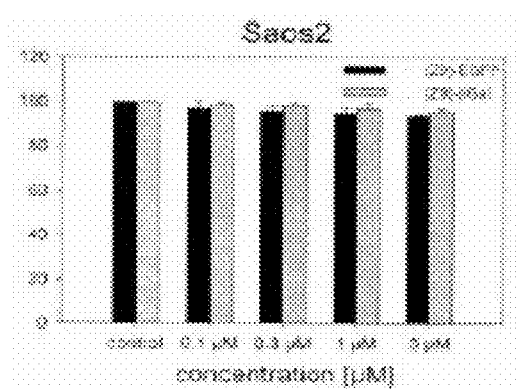
FIG. 3E shows the viability of the Saos2 cells after the internalization of Z9-EGFP at different concentrations. The Saos2 cells are incubated for 24 hours with respectively 0.1 μM, 0.3 μM, 1 μM or 3 μM of Z9-EGFP in the culture medium at 37° C. The cytotoxicity after the internalization of Z9-EGFP is determined by the presence of lactic dehydrogenase (LDH) in the culture medium. Each column represents the average viability of two independent experiments repeated in triplicate. The X-axis represents the cell concentration (μM). The Y-axis represents the cell viability.
Figure 3F:
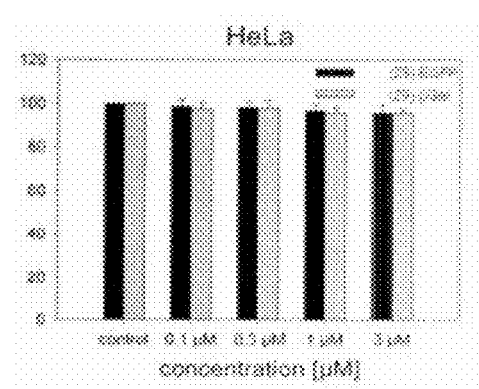
FIG. 3F shows the viability of the HeLa cells after the internalization of Z9-EGFP at different concentrations. The HeLa cells are incubated for 24 hours with respectively 0.1 μM, 0.3 μM, 1 μM or 3 μM of Z9-EGFP in the culture medium at 37° C. The cytotoxicity after the internalization of Z9-EGFP is determined by the presence of lactic dehydrogenase (LDH) in the culture medium. Each column represents the average viability of two independent experiments repeated in triplicate. The X-axis represents the cell concentration (μM). The Y-axis represents the cell viability.

The toxicity of Z9-EGFP and that of Z9-βGal are measured using lactic dehydrogenase (LDH). The LDH enzyme is cytosolic and can be detected in the culture medium after the rupture of the cell membranes. The Saos2 and HeLa cells are incubated with a fusion protein (Z9-EGFP or Z9-βGal) of different indicated concentrations (0.1-0.3 µM). 24 hours after the addition of the fusion proteins, no difference in cell viability is observed between the cells incubated with the fusion protein Z9-EGFP or Z9-βGal and those incubated in the culture medium without fusion protein (FIGS. 3E and 3F).

2.5 Internalization Mechanism

The heparan sulphate proteoglycans (HSPGs) play a significant role in the cell internalization carried out by CCps.

Figure 1G:
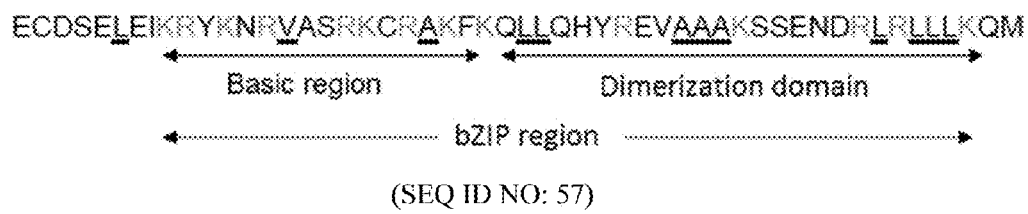
FIG. 1G represents the amino acid sequence of the minimal domain of the ZEBRA protein (SEQ ID NO: 57). The basic residues are marked in grey, and the hydrophobic residues are underlined.
Figure 4A:
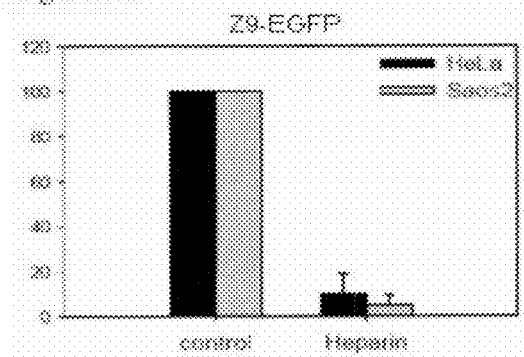
FIG. 4A shows the effect of heparin on the internalization of Z9-EGFP fragment into the HeLa cells represented by the black bar, and the Saos2 cells represented by the grey bar. The cells are incubated for 30 minutes at 37° C. with 20 µg/ml of heparin and then exposed to 0.2 µM of Z9-EGFP for 3 hours at 37° C. The cells are incubated with trypsin for 10 minutes at 37° C. and rinsed before being analyzed by flow cytometry. The Y-axis represents the level of internalization of Z9-EGFP into the cells.

In order to evaluate the role of HSPGs involved in the internalization carried out by Z9-EGFP, the HeLa and Saos2 cells are incubated for 30 minutes with 20 µg/ml of heparin before the addition of Z9-EGFP. The heparin is a structural homologue of HSPGs and can compete with the binding of the latter to Z9-EGFP. The internalization of Z9-EGFP is significantly inhibited by the presence of heparin (FIG. 4A). These results show that the cell internalization of Z9-EGFP requires the interaction between negatively charged HSPGs and the basic amino acids located in the Z9 sequence (FIG. 1G).

Figure 4B:
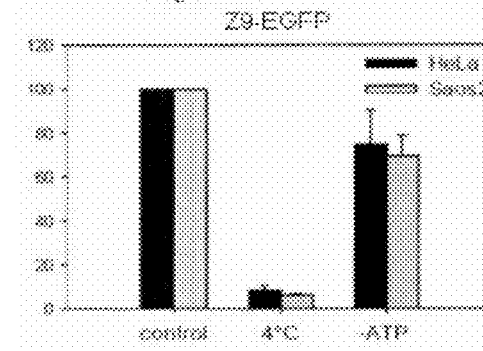
FIG. 4B shows the effect of low temperature and exhaustion of the cellular ATP reserve on the internalization of Z9-EGFP fragment. The HeLa cells represented by the black bar and the Saos2 cells represented by the grey bar are incubated with 0.2 µM of Z9-EGFP for 1 hour at 4° C. In order to exhaust the cellular ATP reserve, the cells are incubated for 1 hour with 6 mM of 2-deoxy-D-glucose and 10 mM of sodium azide, then exposed to 0.2 µM of Z9-EGFP for 1 hour. After the treatment with trypsin, the cells are analyzed by flow cytometry. The Y-axis represents the level of internalization of Z9-EGFP into the cells.

The effect of low temperature and the effect of the exhaustion of the cellular ATP reserve on the internalization of Z9-EGFP fragment is analyzed. After the incubation of HeLa and Saos2 cells at 4° C., the intracellular fluorescent signal in these cells is considerably reduced (FIG. 4B). After the exhaustion of the cellular ATP reserve, only a 20-30% reduction in cell fluorescence is observed in all the cell lines studied (FIG. 4B).

These results mean that the internalization of Z9-EGFP is generally independent of ATP.

Figure 4C:
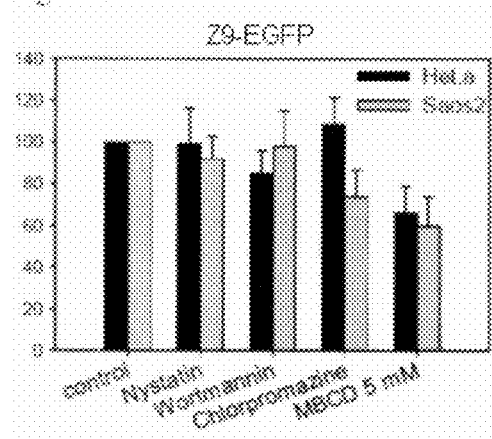
FIG. 4C shows the effect of different endocytotic inhibitors on the internalization of Z9-EGFP fragment into the HeLa cells represented by the black bar, and the Saos2 cells represented by the grey bar. The cells are treated respectively with 20 µg/ml of heparin, 100 nM of wortmannin, 50 µg/ml of nystatin, 30 µM of chlorpromazine hydrochloride and 5-10 mM of methyl-β-cyclodextrin (MβCD) for 30 minutes, before the addition of 0.2 µM of Z9-EGFP. The mean cell fluorescence measured in the treated cells is normalized with respect to that measured in the untreated cells, as a control. Each experiment is repeated independently in triplicate. The Y-axis represents the level of internalization of Z9-EGFP into the cells.

In order to clarify the internalization route of ZEBRA, the effect of several endocytosis inhibitors is analyzed. Nystatin is a known caveolin-dependent endocytosis inhibitor. The HeLa and Saos2 cells are treated with 50 µg/ml of nystatin before the addition of 0.2 µM of Z9-EGFP. In all the cell lines, the fluorescent signal for Z9-EGFP in the presence of nystatin is identical to that under the control conditions (FIG. 4C). These results show that the internalization of Z9-EGFP does not take the caveolin-dependent endocytosis route.

Macropinocytosis, the internalization route taken by CPPs, is a rapid and non-specific internalization mechanism. Macropinocytosis depends on the activity of phosphatidylinosital-3-kinase (PI3K) and is inhibited by wortmannin. The impact of wortmannin on the HeLa and Saos2 cells is analyzed. The efficiency of Z9-EGFP internalization into all the cell lines treated with 100 nM of wortmannin is not modified relative to that into the untreated cell lines (FIG. 4C). These results indicate that the internalization using Z9 does not take the macropinocytosis route.

In order to analyze whether the internalization of Z9-EGFP involves endocytosis using CCP, the internalization of Z9-EGFP is measured in the presence of chlorpromazine. After incubation of HeLa and Saos2 cells for 30 minutes with 30 µM of chlorpromazine, Z9-EGFP is added to the culture medium. The fluorescence emitted by EGFP is considerably reduced in the Saos2 cells, but not in the HeLa cells (FIG. 4C). These results mean that there may be different Z9-EGFP internalization mechanisms depending on the type of cells.

Figure 7:
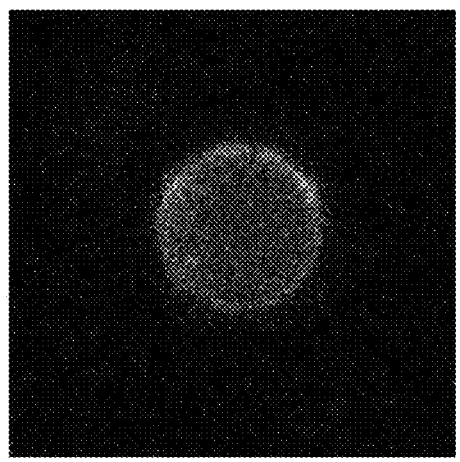
FIG. 7 shows the entry of Z9-EGFP into synthetic liposomes.

In order to analyze whether the internalization of Z9-EGFP involves endocytosis using lipid rafts, the cells are treated with methyl-β-cyclodextrin in order to remove cholesterols associated with the surface of cells. This treatment results from lipid raft disruption. FIG. 4C shows that the internalization of Z9-EGFP into the treated cells is affected relative to that into the control cells. These results show that endocytosis using lipid rafts is involved in the internalization of Z9-EGFP. However, 60% of the internalization of Z9-EGFP uses another mechanism. This finding is supported by the experiments on the entry of Z9-EGFP into synthetic liposomes (FIG. 7). The dark red lipophilic stain (10 µM), is added to the synthetic liposome preparation Immediately after the staining reaction, the liposomes are incubated for 30 minutes with Z9-EGFP and analyzed by confocal microscopy. The fluorescence emitted by GFP is detected in turn and inside lipid vesicles, this means a direct translocation through the lipid membrane.

2.6 Intracellular Localization of Z9-EGFP

Immunofluorescence microscopy is used to study the subcellular co-localization of the Z9-EGFP peptide internalized with endosome markers such as EEA1, Rab7, caveolin-1, and calthrin. The HeLa and Saos2 cells are incubated for 30 minutes for up to 15 h with Z9-EGFP at 37° C. The protein internalization is analyzed by confocal microscopy. The presence of Z9-EGFP inside cells is confirmed by the direct visualization of the intracellular fluorescence emitted by EGFP or by a labelled antibody which is directed against EGFP.

Figure 5A:
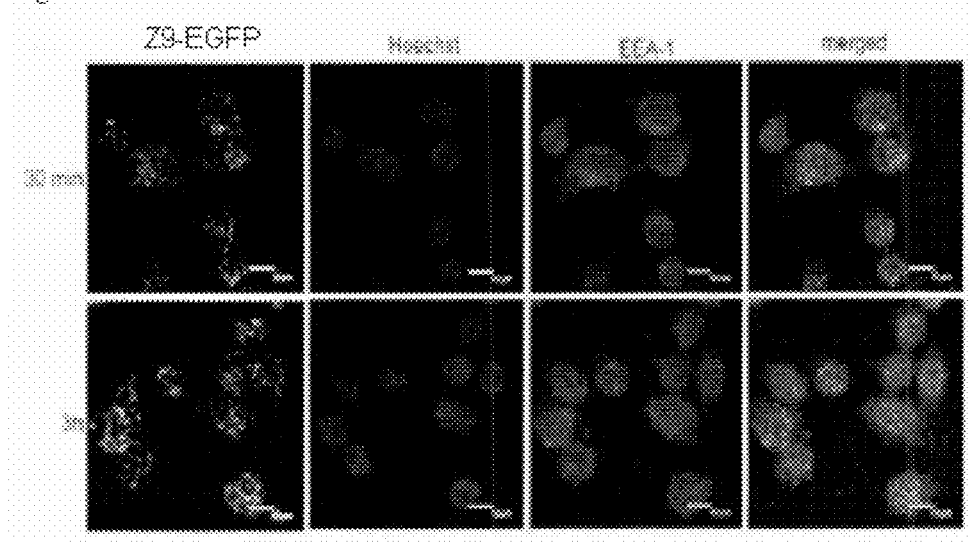
FIG. 5A shows the intracellular localization of Z9-EGFP in the HeLa cells. The cells are incubated for 30 minutes or 3 hours respectively with 0.2 µM of Z9-EGFP. The cells are visualized by confocal microscopy. The images are acquired sequentially. The white arrows in the photos in the first column on the left indicate the presence of Z9-EGFP in the cells. The white arrows in the photos in the second column from the left indicate the nuclei, which are revealed by the fluorescent stain Hoechst 33258. The white arrows in the photos in the third column from the left indicate the EEA-1 endosome markers, which are revealed by the fluorescent stain ALEXA FLUOR® 647. The white arrows in the photos in the first column on the right indicate the superimposition of the fluorescent signals emitted by the nuclei, by Z9-EGFP in the cells, and by the EEA-1 markers. The white bar represents 10 µm.
Figure 5B:
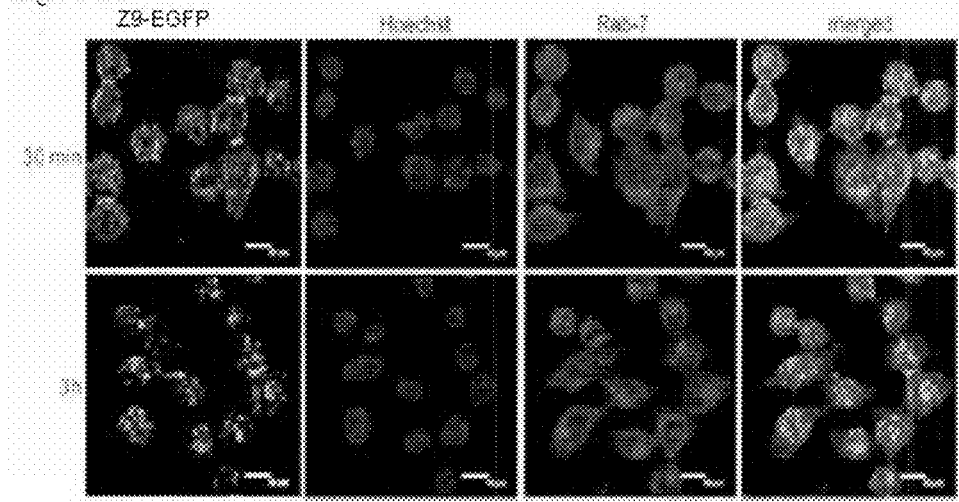
FIG. 5B shows the intracellular localization of Z9-EGFP in the HeLa cells. The cells are incubated for 30 minutes or 3 hours respectively with 0.2 µM of Z9-EGFP. The cells are visualized by confocal microscopy. The images are acquired sequentially. The white arrows in the photos in the first column on the left indicate the presence of Z9-EGFP in the cells. The white arrows in the photos in the second column from the left indicate the nuclei, which are revealed by the fluorescent stain Hoechst 33258. The white arrows in the photos in the third column from the left indicate the Rab-7 endosome markers, which are revealed by the fluorescent stain ALEXA FLUOR® 647. The white arrows in the photos in the first column on the right indicate the superimposition of the fluorescent signals emitted by the nuclei, by Z9-EGFP in the cells, and by the Rab-7 markers. The white bar represents 10 µm.
Figure 5C:
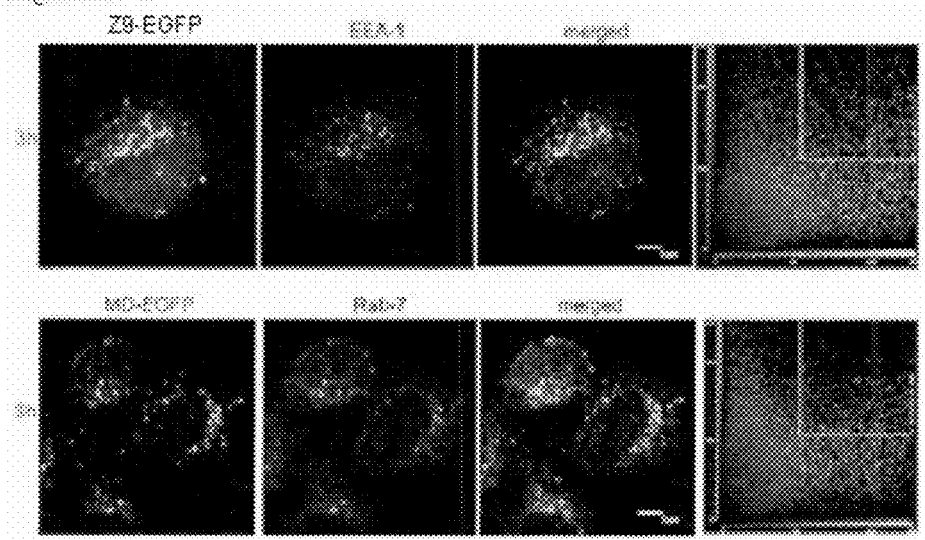
FIG. 5C shows the intracellular localization of Z9-EGFP in the HeLa cells. The cells are incubated for 3 hours respectively with 0.2 µM of Z9-EGFP. The white arrows in the photos in the second column from the left indicate the Rab-7 or EEA-1 endosome markers, which are revealed by the fluorescent stain ALEXA FLUOR® 647. The white arrows in the photos in the third column from the right indicate the superimposition of the fluorescent signals emitted by Z9-EGFP in the cells and by the Rab-7 or EEA-1 markers. The white bar represents 5 µm. The diagram on the right represents the relative intensity of pixels.
Figure 5D:
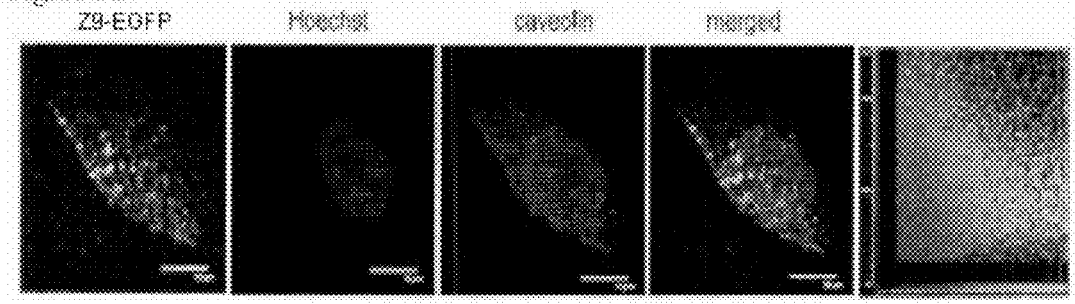
FIG. 5D shows the intracellular localization of Z9-EGFP in the HeLa cells. The cells are incubated for 3 hours respectively with 0.2 µM of Z9-EGFP. The white arrows in the photos in the first column on the left indicate the presence of Z9-EGFP in the cells. The white arrows in the photos in the second column from the left indicate the nuclei, which are revealed by the fluorescent stain Hoechst 33258. The white arrows in the photos in the third column from the left indicate the caveolin-1 endosome markers, which are revealed by ALEXA FLUOR® 647. The white arrows in the photos in the second column from the right indicate the superimposition of the fluorescent signals emitted by the nuclei, by Z9-EGFP in the cells, and by the caveolin-1 markers. The diagram on the right represents the relative intensity of pixels.
Figure 5E:
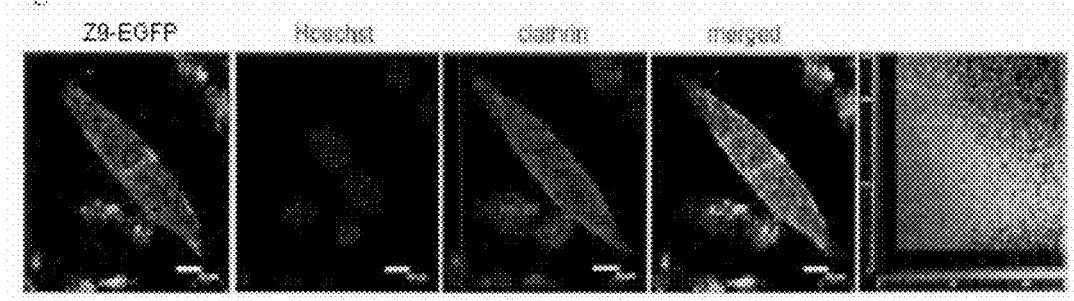
FIG. 5E shows the intracellular localization of Z9-EGFP in the HeLa cells. The cells are incubated for 3 hours respectively with 0.2 µM of Z9-EGFP. The white arrows in the photos in the first column on the left indicate the presence of Z9-EGFP in the cells. The white arrows in the photos in the second column from the left indicate the nuclei, which are revealed by the fluorescent stain Hoechst 33258. The white arrows in the photos in the third column from the left indicate the clathrin endosome markers, which are revealed by ALEZA FLUOR® 647. The white arrows in the photos in the second column from the right indicate the superimposition of the fluorescent signals emitted by the nuclei, by Z9-EGFP in the cells, and by the clathrin markers. The diagram on the right represents the relative intensity of pixels.

The majority of the EGFP signal is not co-localized with that of EEA1 and Rab7 in the same cell line (FIGS. 5A, 5B, 5C). Nevertheless, part of the EGFP signal is superimposed with that of the endosomal marker. The variation in incubation time does not modify this result. Moreover, the EGFP signal is also not co-localized with that of caveolin or clathrin (FIG. 5D, 5E).

2.7 Internalization of β-Galactosidase into the Cells

Figure 6:
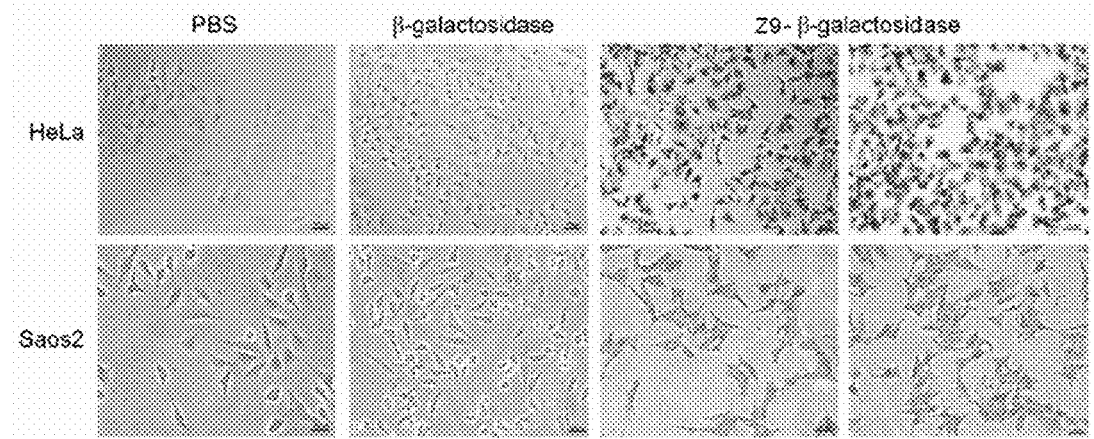
FIG. 6 shows the internalization of the functional β-galactosidase into the HeLa and Saos2 cells using Z9 fragment. The cells are fixed and detected by the X-Gal detection kit (Sigma), after incubation for 16 hours with 0.2 µM of Z9-β-galactosidase at 37° C. The presence of the β-galactosidase is visualized by phase contrast microscopy. The photos in the first column on the left represent the cells incubated only in a PBS buffer. The photos in the second column from the left represent the cells incubated with the β-galactosidase. The photos of two columns on the right represent the cells incubated with the Z9-β-galactosidase fusion protein. The black bar represents 10 µm.

In order to test the ability of the Z9 fragment as a transporter intended for the internalization of a molecule of interest into the target cells, the Z9 fragment is fused to β-galactosidase, a 120 kDa protein. The Z9-βGal fusion protein is added to the HeLa or Saos2 cells in a culture medium without serum. The cells are fixed and revealed by the method described in the section above. FIG. 6 shows the internalization of β-galactosidase into the HeLa or Saos2 cells. The presence of functional β-galactosidase in the cells is revealed by staining cells blue. Like the internalization of EGFP by the Z9 fragment, Z9-β-galactosidase is internalized into 100% of the cell population. The β-galactosidase protein is also used alone as a negative control, and no β-galactosidase activity is detected in the control cells.

2.8 Activation of the Caspase Pathway

Figure 8:
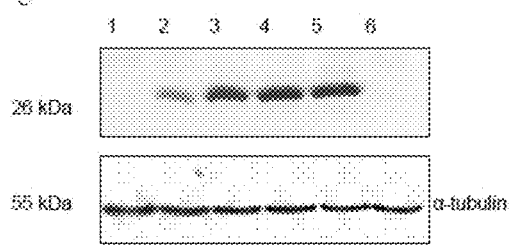
FIG. 8 shows the analysis of the activation of the caspase pathway in mouse glioblastoma cells (GL26) after treatment and internalization of the Z9-eIF3-f fusion protein, represented by the sequence SEQ ID NO: 35. Track 1: control without protein; tracks 2 to 5: 0.07 nM, 0.13 nM; 0.25 nM; 0.31 nM respectively; track 6: control with etoposide. The activation of the caspase pathway is carried out by detection of activated and cleaved caspase-9 in order to produce a 26 kDa band.
Figure 9:
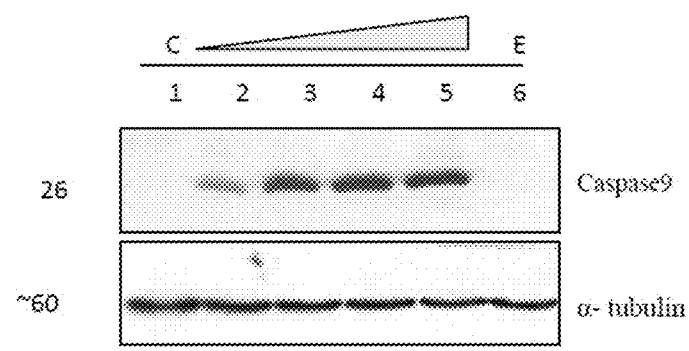
FIG. 9 shows the analysis of the activation of the caspase route in mouse glioblastoma cells (GL26) after treatment and internalization of the fusion protein Z9-eIF3-f, represented by the sequence SEQ ID NO: 35. Track 1: control without protein; tracks 2 to 5: 0.07 nM, 0.13 nM; 0.25 nM; 0.31 nM respectively; track 6: control with etoposide. The activation of the caspase route is carried out by detection of the activated and cleaved caspase-9 in order to produce a 26 kDa band.

The activation of the caspase pathway is analyzed in mouse glioblastoma cells (GL26) after treatment and internalization of the Z9-eIF3-f fusion protein. The eIF3-f protein can interact with a CDK11(CDK11p46) isoform treated with caspases. The mouse glioblastoma cells (GL26) are internalized by the Z9-eIF3-f fusion protein constructed by the primers eIF3-N (D1) and eIF3-N (R1). The activation of the caspase pathway is carried out by detection of the cleaved activated caspase-9 in order to produce a 26 kDa band (FIG. 8).

2.9 Internalization of the FERM-MD (Z9) Fusion Protein into the Cells

Figure 10A:
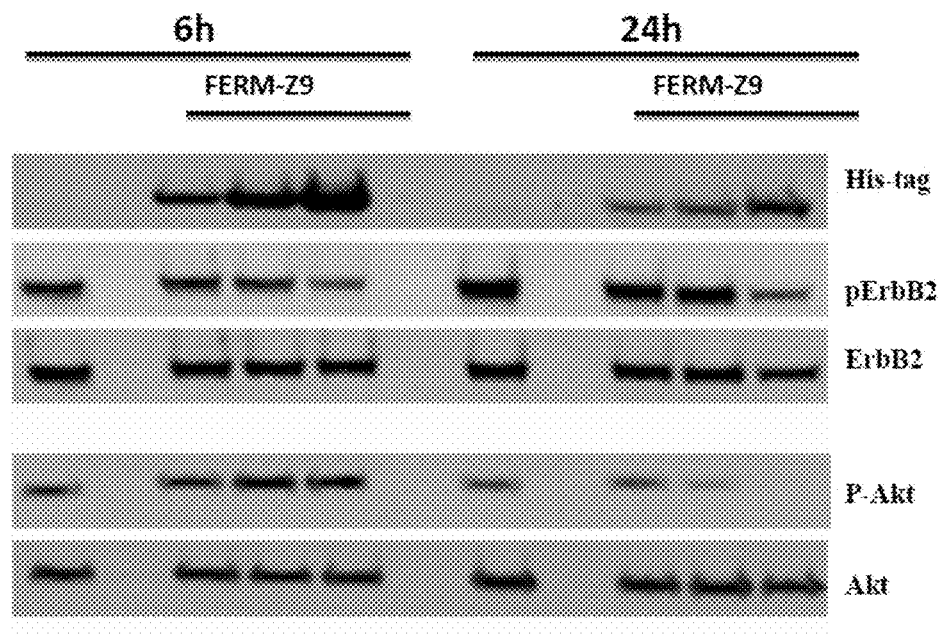
FIG. 10A shows the analysis of the cellular effects in human mammary carcinoma cells (SKBR3) after treatment and internalization of the FERM-Z9 fusion protein, represented by the sequence 40. Track 1: T=0, control without protein; tracks 2 to 4: 0.3 µM, 0.6 µM; 0.9 µM respectively after treatment for 6 hours in the presence of the FERM-Z9 fusion protein; track 5: T=0, control without protein; tracks 6 to 8: 0.3 µM, 0.6 µM; 0.9 µM respectively after treatment for 24 h in the presence of the FERM-Z9 fusion protein. The internalization of the FERM-Z9 fusion protein is revealed by an anti-histidine antibody (His-tag); the activity of the ErbB2 and Akt proteins by anti-phospho ErbB2 (pErbB2) and Akt (P-Akt) antibodies respectively. The presence of the ErbB2 and Akt proteins as a control is revealed by anti-ErbB2 (ErbB2) and Akt (Akt) antibodies respectively. A reduction in the activity and phosphorylation of the ErbB2 receptor and of the Akt protein is detected after treatment for 24 hours with the FERM-Z9 fusion protein for concentrations ranging from 0.3 µM to 0.9 µM.
Figure 10B:
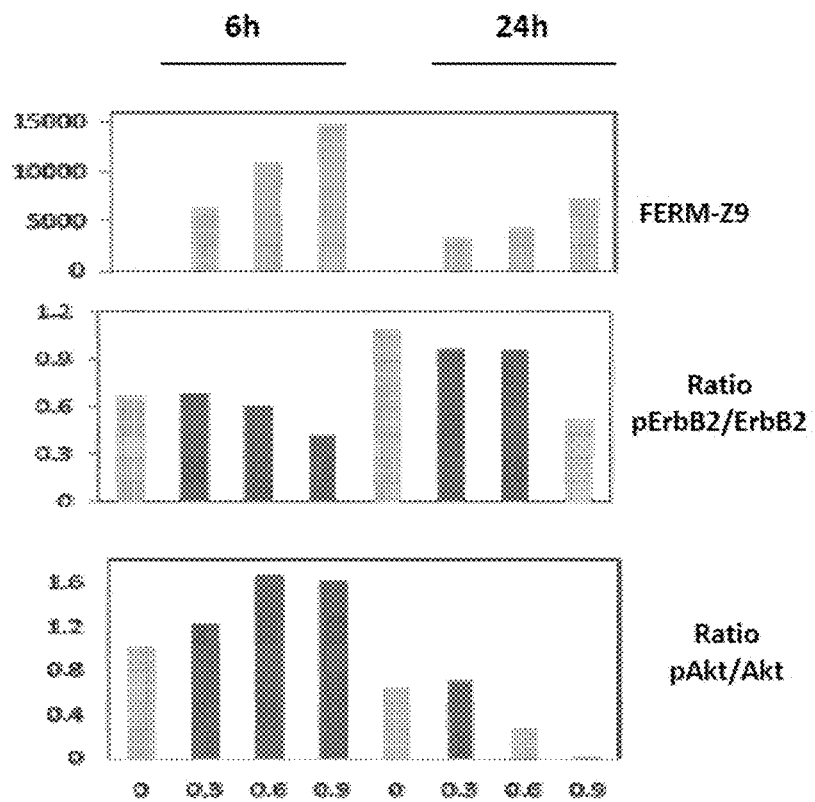
FIG. 10B shows a diagrammatic representation of the cellular effects in human mammary carcinoma cells (SKBR3) after treatment for 6 or 24 hours and internalization of the FERM-Z9 fusion protein. Top diagram; quantitative analysis of the FERM-Z9 fusion protein detected in the human mammary carcinoma cells (SKBR3) after treatment and internalization. The Y-axis indicates the number of FERM-Z9 fusion proteins revealed by an anti-histidine antibody (arbitrary units). The X-axis indicates the concentration of FERM-Z9 fusion protein used in the treatment of the SKBR3 cells at 6 or 24 hours. The quantities of ErbB2 and Akt proteins phosphorylated after treatment are quantified relative to the total quantity of ErbB2 and Akt protein respectively indicating a reduction in phosphorylation as a consequence of the activity of these proteins as a function of the growing quantities of FERM-Z9 fusion protein used in these experiments.

The FERM-MD (Z9) fusion protein is internalized into human mammary carcinoma cells (SKBR3). The presence of the fusion protein in the cells is revealed by an anti-histidine antibody (His-tag) after treatment for 6 hours (FIGS. 10A and 10B). The ErbB2 and Akt proteins, which express in the SKBR3 cells are used as controls, and are revealed by anti-ErbB2 (ErbB2) and Akt (Aid) antibodies respectively. A reduction in the activity and phosphorylation of the ErbB2 receptor and of the Akt protein is detected after treatment for 24 hours with the FERM-MD (Z9) fusion protein for concentrations ranging from 0.3 μM to 0.9 μM.

The invention claimed is:

1. A composition, comprising:
    a target polypeptide selected from the group consisting of a mouse eukaryotic initiation factor 3 (eIF3-f) comprising SEQ ID NO: 19, human eIF3-f comprising SEQ ID NO: 20, and a protein having a 4.1 ezrin, radixin, moesin (FERM) domain comprising SEQ ID NO: 27; and
    a transporter polypeptide comprising the DNA-binding domain (DB) and the leucine zipper type dimerization domain (DIM) of an EBV ZEBRA protein comprising the amino acid sequence of SEQ ID NO: 1,
    wherein the target polypeptide is linked to the transporter polypeptide by a covalent bond, a non-covalent bond, an ionic bond, a hydrogen bond, or a hydrophobic bond.

2. The composition according to claim 1, wherein the transporter polypeptide is present in the composition at a concentration of less than 1 nM.

3. The composition according to claim 1, wherein the transporter polypeptide is present in the composition at a concentration of less than 0.1 nM.

4. The composition according to claim 1, wherein the transporter polypeptide is present in the composition at a concentration of less than 0.03 nM.

5. The composition according to claim 1, wherein the transporter polypeptide is present in the composition at a concentration of less than 5 nM.

6. A pharmaceutical composition, comprising the composition of claim 1 and a pharmaceutically acceptable carrier.

7. The pharmaceutical composition according to claim 6, wherein said target polypeptide and said transporter polypeptide are in the form of a fusion protein.

8. The pharmaceutical composition according to claim 6, said composition being formulated for a daily administration of 1 mg/m$^2$ to 1000 mg/m$^2$.

9. A fusion protein, comprising
    a target polypeptide selected from the group consisting of mammalian eukaryotic initiation factor of 3 (eIF3-f) comprising SEQ ID NO: 19, human eIF3-f comprising SEQ ID NO: 20, and a protein having a 4.1 ezrin, radixin, moesin (FERM) domain comprising SEQ ID NO: 27;
    fused with a transporter polypeptide comprising the DNA-binding domain (DB) and the leucine zipper type dimerization domain (DIM) of an EBV ZEBRA protein comprising the amino acid SEQ ID NO: 1.

10. The fusion peptide according to claim 9, wherein the target polypeptide is fused to the N-terminal end of the transporter polypeptide.

11. The fusion peptide according to claim 9, wherein the target polypeptide is fused to the C-terminal end of the transporter polypeptide.

12. The fusion peptide according to claim 9, comprising the amino acid sequence selected from the group consisting of SEQ ID NO: 35, SEQ ID NO: 48, SEQ ID NO: 40, and SEQ ID NO: 53.

* * * * *

SEQUENCE LISTING

```
<160> NUMBER OF SEQ ID NOS: 94

<210> SEQ ID NO 1
<211> LENGTH: 51
<212> TYPE: PRT
<213> ORGANISM: Epstein Barr virus

<400> SEQUENCE: 1

Glu Cys Asp Ser Glu Leu Glu Ile Lys Arg Tyr Lys Asn Arg Val Ala
1               5                   10                  15

Ser Arg Lys Cys Arg Ala Lys Phe Lys Gln Leu Leu Gln His Tyr Arg
            20                  25                  30

Glu Val Ala Ala Ala Lys Ser Ser Glu Asn Asp Arg Leu Arg Leu Leu
        35                  40                  45

Leu Lys Gln
    50

<210> SEQ ID NO 2
<211> LENGTH: 298
<212> TYPE: PRT
<213> ORGANISM: Xenopus

<400> SEQUENCE: 2

Met Arg His Met Gln Ser Ala Thr Arg Ala Thr Leu Val Cys Gly Ser
1               5                   10                  15

Gly Val Lys Gln Ile Ile Ala Lys Gly His Pro Asn Thr Arg Val Phe
            20                  25                  30

Gly Ala Arg Lys Ala Arg Ile Pro Glu Arg Glu Val Leu Ala Ala Lys
        35                  40                  45
```

-continued

```
Pro Lys Ile Thr Arg Ile Thr His Leu Asn Leu Gln Pro Gln Glu Arg
    50                  55                  60

Gln Ala Phe Tyr Arg Leu Leu Glu Asn Glu Leu Ile Gln Glu Phe Leu
65              70                  75                  80

Ser Met Asp Ser Cys Leu Lys Ile Ser Asp Lys Tyr Leu Ile Ala Met
                85                  90                  95

Val Leu Ala Tyr Phe Lys Arg Ala Gly Leu Tyr Thr Gly Glu Tyr Thr
            100                 105                 110

Thr Met Asn Phe Phe Val Ala Leu Tyr Leu Ala Asn Asp Met Glu Glu
        115                 120                 125

Asp Glu Glu Asp Tyr Lys Tyr Glu Ile Phe Pro Trp Ala Leu Gly Asp
    130                 135                 140

Ser Trp Arg Glu Phe Phe Pro Gln Phe Leu Arg Leu Arg Asp Asn Phe
145                 150                 155                 160

Trp Ala Lys Met Asn Tyr Arg Ala Val Val Ser Arg Arg Cys Cys Asp
                165                 170                 175

Glu Val Met Ala Lys Asp Pro Thr His Trp Ala Trp Leu Arg Asp Arg
            180                 185                 190

Pro Ile His His Ser Gly Ala Leu Arg Gly Tyr Leu Arg Asn Glu Asp
        195                 200                 205

Asp Phe Phe Pro Arg Gly Pro Gly Leu Thr Pro Ala Ser Cys Ala Leu
    210                 215                 220

Cys His Lys Ala Ser Val Cys Asp Ser Gly Val Ala His Asp Asn
225                 230                 235                 240

Ser Ser Pro Glu Gln Glu Ile Phe His Tyr Thr Asn Arg Glu Trp Ser
                245                 250                 255

Gln Glu Leu Leu Ile Leu Pro Pro Glu Leu Leu Leu Asp Pro Glu Ser
            260                 265                 270

Thr Tyr Asp Ile His Ile Phe Gln Glu Pro Leu Val Gly Leu Glu Pro
        275                 280                 285

Asp Gly Ala Ala Leu Glu Trp His His Leu
    290                 295

<210> SEQ ID NO 3
<211> LENGTH: 131
<212> TYPE: PRT
<213> ORGANISM: Homo sapiens

<400> SEQUENCE: 3

Gln Glu Val Gln Ala Phe Leu Ser Leu Leu Glu Asp Ser Phe Val Gln
1               5                   10                  15

Glu Phe Leu Ser Lys Asp Pro Cys Phe Gln Ile Ser Asp Lys Tyr Leu
                20                  25                  30

Leu Ala Met Val Leu Val Tyr Phe Gln Arg Ala His Leu Lys Leu Ser
            35                  40                  45

Glu Tyr Thr His Ser Ser Leu Phe Leu Ala Leu Tyr Leu Ala Asn Asp
        50                  55                  60

Met Glu Glu Asp Leu Glu Gly Pro Lys Cys Gly Ile Phe Pro Trp Ala
65              70                  75                  80

Leu Gly Lys Asp Trp Cys Leu Arg Val Gly Lys Phe Leu His Gln Arg
                85                  90                  95

Asp Lys Leu Trp Ala Arg Met Gly Phe Arg Ala Val Val Ser Arg Gln
            100                 105                 110

Cys Cys Glu Glu Val Met Ala Lys Glu Pro Phe His Trp Ala Trp Thr
```

Arg Asp Arg
    130

<210> SEQ ID NO 4
<211> LENGTH: 131
<212> TYPE: PRT
<213> ORGANISM: Mus musculus

<400> SEQUENCE: 4

Gln Glu Met Thr Ala Phe Phe Lys Leu Phe Asp Asp Leu Ile Gln
1               5                   10                  15

Asp Phe Leu Trp Met Asp Cys Cys Lys Ile Ala Asp Lys Tyr Leu
            20                  25                  30

Leu Ala Met Thr Phe Val Tyr Phe Lys Arg Ala Lys Phe Thr Ile Asn
            35                  40                  45

Glu His Thr Arg Ile Asn Phe Phe Ile Ala Leu Tyr Leu Ala Asn Thr
        50                  55                  60

Val Glu Glu Asp Glu Glu Ala Lys Tyr Glu Ile Phe Pro Trp Ala
65                  70                  75                  80

Leu Gly Lys Asn Trp Arg Lys Leu Phe Pro Asn Phe Leu Lys Leu Arg
                85                  90                  95

Asp Gln Leu Trp Asp Arg Ile Asp Tyr Arg Ala Ile Val Ser Arg Arg
            100                 105                 110

Cys Cys Glu Glu Val Met Ala Ile Ala Pro Thr His Tyr Ile Trp Gln
        115                 120                 125

Arg Glu Arg
    130

<210> SEQ ID NO 5
<211> LENGTH: 133
<212> TYPE: PRT
<213> ORGANISM: Xenopus

<400> SEQUENCE: 5

Pro Gln Glu Arg Gln Ala Phe Tyr Arg Leu Leu Glu Asn Glu Leu Ile
1               5                   10                  15

Gln Glu Phe Leu Ser Met Asp Ser Cys Leu Lys Ile Ser Asp Lys Tyr
            20                  25                  30

Leu Ile Ala Met Val Leu Ala Tyr Phe Lys Arg Ala Gly Leu Tyr Thr
            35                  40                  45

Gly Glu Tyr Thr Thr Met Asn Phe Phe Val Ala Leu Tyr Leu Ala Asn
        50                  55                  60

Asp Met Glu Glu Asp Glu Glu Asp Tyr Lys Tyr Glu Ile Phe Pro Trp
65                  70                  75                  80

Ala Leu Gly Asp Ser Trp Arg Glu Phe Phe Pro Gln Phe Leu Arg Leu
                85                  90                  95

Arg Asp Asn Phe Trp Ala Lys Met Asn Tyr Arg Ala Val Val Ser Arg
            100                 105                 110

Arg Cys Cys Asp Glu Val Met Ala Lys Asp Pro Thr His Trp Ala Trp
        115                 120                 125

Leu Arg Asp Arg Pro
    130

<210> SEQ ID NO 6
<211> LENGTH: 133
<212> TYPE: PRT

<213> ORGANISM: Xenopus

<400> SEQUENCE: 6

Pro Gln Glu Arg Gln Ala Phe Tyr Arg Leu Leu Glu Asn Glu Leu Ile
1               5                   10                  15

Gln Glu Phe Leu Ser Met Asp Ser Cys Leu Lys Ile Ser Asp Lys Tyr
            20                  25                  30

Leu Ile Ala Met Val Leu Ala Tyr Phe Lys Arg Ala Gly Leu Tyr Thr
        35                  40                  45

Gly Glu Tyr Thr Thr Met Asn Phe Phe Val Ala Leu Tyr Leu Ala Asn
    50                  55                  60

Asp Met Glu Glu Asp Glu Asp Tyr Lys Tyr Glu Ile Phe Pro Trp
65                  70                  75                  80

Ala Leu Gly Asp Ser Trp Arg Glu Phe Phe Pro Gln Phe Leu Arg Leu
                85                  90                  95

Arg Asp Asn Phe Trp Ala Lys Met Asn Tyr Arg Ala Val Val Ser Arg
            100                 105                 110

Arg Cys Cys Asp Glu Val Met Ala Lys Asp Pro Thr His Trp Ala Trp
        115                 120                 125

Leu Arg Asp Arg Pro
    130

<210> SEQ ID NO 7
<211> LENGTH: 131
<212> TYPE: PRT
<213> ORGANISM: Drosophila

<400> SEQUENCE: 7

Gln Glu Met Thr Ala Phe Phe Lys Leu Phe Asp Asp Leu Ile Gln
1               5                   10                  15

Asp Phe Leu Trp Met Asp Cys Cys Lys Ile Ala Asp Lys Tyr Leu
            20                  25                  30

Leu Ala Met Thr Phe Val Tyr Phe Lys Arg Ala Lys Phe Thr Ile Asn
        35                  40                  45

Glu His Thr Arg Ile Asn Phe Phe Ile Ala Leu Tyr Leu Ala Asn Thr
    50                  55                  60

Val Glu Glu Asp Glu Glu Ala Lys Tyr Glu Ile Phe Pro Trp Ala
65                  70                  75                  80

Leu Gly Lys Asn Trp Arg Lys Leu Phe Pro Asn Phe Leu Lys Leu Arg
                85                  90                  95

Asp Gln Leu Trp Asp Arg Ile Asp Tyr Arg Ala Ile Val Ser Arg Arg
            100                 105                 110

Cys Cys Glu Glu Val Met Ala Ile Ala Pro Thr His Tyr Ile Trp Gln
        115                 120                 125

Arg Glu Arg
    130

<210> SEQ ID NO 8
<211> LENGTH: 133
<212> TYPE: PRT
<213> ORGANISM: Artificial sequence
<220> FEATURE:
<223> OTHER INFORMATION: Human protein derivative
<220> FEATURE:
<221> NAME/KEY: MISC_FEATURE
<222> LOCATION: (1)..(6)
<223> OTHER INFORMATION: X is selected from: A, R, N, D, C, E, S, Q, G,
      H, I, L, K, M, F, P, S, T, W, Y, V
<220> FEATURE:

-continued

```
<221> NAME/KEY: MISC_FEATURE
<222> LOCATION: (8)..(9)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (11)..(18)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (21)..(22)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (24)..(29)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (34)..(35)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (37)..(39)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (42)..(42)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (45)..(56)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (58)..(58)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (65)..(67)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (68)..(72)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (70)..(73)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (75)..(75)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (78)..(81)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (83)..(92)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (94)..(96)
<223> OTHER INFORMATION: X is selected from: A, R, N, D, C, E, S, Q, G,
      H, I, L, K, M, F, P, S, T, W, Y, V
```

```
<220> FEATURE:
<221> NAME/KEY: MISC_FEATURE
<222> LOCATION: (97)..(109)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (113)..(114)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (116)..(116)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (118)..(127)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (129)..(129)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (131)..(131)
<223> OTHER INFORMATION: X is selected from: A, R, N, D, C, E, S, Q, G,
      H, I, L, K, M, F, P, S, T, W, Y, V
<220> FEATURE:
<221> NAME/KEY: MISC_FEATURE
<222> LOCATION: (133)..(133)
<223> OTHER INFORMATION: X is selected from: A, R, N, D, C, E, S, Q, G,
      H, I, L, K, M, F, P, S, T, W, Y, V

<400> SEQUENCE: 8

Xaa Xaa Xaa Xaa Xaa Xaa Phe Xaa Xaa Leu Xaa Xaa Xaa Xaa Xaa
1               5                   10                  15

Xaa Xaa Leu Phe Xaa Xaa Asp Xaa Xaa Xaa Xaa Xaa Asp Lys Tyr
            20                  25                  30

Leu Xaa Xaa Met Xaa Xaa Xaa Tyr Phe Xaa Arg Ala Xaa Xaa Xaa Xaa
        35                  40                  45

Xaa Xaa Xaa Xaa Xaa Xaa Xaa Xaa Phe Xaa Ala Leu Tyr Leu Ala Asn
50                  55                  60

Xaa Xaa Xaa Glu Asp Xaa Xaa Xaa Xaa Lys Xaa Ile Phe Xaa Xaa Xaa
65                  70                  75                  80

Xaa Gly Xaa Xaa Xaa Xaa Xaa Xaa Xaa Xaa Xaa Phe Xaa Xaa Xaa
            85                  90                  95

Arg Xaa Xaa Xaa Xaa Xaa Xaa Xaa Xaa Xaa Xaa Xaa Val Ser Arg
            100                 105                 110

Xaa Xaa Cys Xaa Glu Xaa Xaa Xaa Xaa Xaa Xaa Xaa Xaa Xaa Trp
    115                 120                 125

Xaa Arg Xaa Arg Xaa
    130

<210> SEQ ID NO 9
<211> LENGTH: 411
<212> TYPE: PRT
<213> ORGANISM: Rattus norvegicus

<400> SEQUENCE: 9

Met Pro Arg Glu Arg Lys Glu Arg Asp Ser Lys Asp His Ser Asn Met
1               5                   10                  15

Lys Glu Glu Gly Gly Ser Asp Leu Ser Val Arg Ser Arg Lys Arg Lys
            20                  25                  30
```

```
Ala Asn Val Ala Val Phe Leu Gln Asp Pro Asp Glu Glu Ile Ala Lys
             35                  40                  45

Ile Asp Lys Thr Val Lys Ser Gln Asp Ser Ser Gln Pro Trp Asp Asp
 50                  55                  60

Asp Ser Ala Cys Val Asp Pro Cys Ser Phe Ile Pro Thr Pro Asn Lys
 65                  70                  75                  80

Glu Glu Asp Asn Glu Leu Glu Tyr Pro Lys Thr Ala Phe Gln Pro Arg
                 85                  90                  95

Lys Ile Arg Pro Pro Arg Ala Ser Pro Leu Pro Val Leu Asn Trp Gly
                100                 105                 110

Asn Arg Glu Glu Val Trp Arg Ile Met Leu Asn Lys Glu Lys Thr Tyr
                115                 120                 125

Leu Arg Asp Glu His Phe Leu Gln Arg His Pro Leu Leu Gln Ala Arg
                130                 135                 140

Met Arg Ala Val Leu Leu Asp Trp Leu Met Glu Val Cys Glu Val Tyr
145                 150                 155                 160

Lys Leu His Arg Glu Thr Phe Tyr Leu Ala Gln Asp Phe Phe Asp Arg
                165                 170                 175

Tyr Met Ala Ser Gln Gln Asn Ile Ile Lys Thr Leu Leu Gln Leu Ile
                180                 185                 190

Gly Ile Ser Ala Leu Phe Ile Ala Ser Lys Leu Glu Glu Ile Tyr Pro
                195                 200                 205

Pro Lys Leu His Gln Phe Ala Tyr Val Thr Asp Gly Ala Cys Ser Gly
                210                 215                 220

Asp Glu Ile Leu Thr Met Glu Leu Met Met Met Lys Ala Leu Lys Trp
225                 230                 235                 240

Arg Leu Ser Pro Leu Thr Ile Val Ser Trp Leu Asn Val Tyr Val Gln
                245                 250                 255

Val Ala Tyr Val Asn Asp Thr Gly Glu Val Leu Met Pro Gln Tyr Pro
                260                 265                 270

Gln Gln Val Phe Val Gln Ile Ala Glu Leu Leu Asp Leu Cys Val Leu
                275                 280                 285

Asp Val Gly Cys Leu Glu Phe Pro Tyr Gly Val Leu Ala Ala Ser Ala
                290                 295                 300

Leu Tyr His Phe Ser Ser Leu Glu Leu Met Gln Lys Val Ser Gly Tyr
305                 310                 315                 320

Gln Trp Cys Asp Ile Glu Lys Cys Val Lys Trp Met Val Pro Phe Ala
                325                 330                 335

Met Val Ile Arg Glu Met Gly Ser Ser Lys Leu Lys His Phe Arg Gly
                340                 345                 350

Val Pro Met Glu Asp Ser His Asn Ile Gln Thr His Thr Asn Ser Leu
                355                 360                 365

Asp Leu Leu Asp Lys Ala Gln Ala Lys Lys Ala Ile Leu Ser Glu Gln
                370                 375                 380

Asn Arg Ile Ser Pro Pro Pro Ser Gly Val Leu Thr Pro Pro His Ser
385                 390                 395                 400

Ser Lys Lys Gln Ser Ser Glu Gln Glu Thr Glu
                405                 410

<210> SEQ ID NO 10
<211> LENGTH: 20
<212> TYPE: PRT
<213> ORGANISM: Rattus norvegicus

<400> SEQUENCE: 10
```

-continued

Glu Leu Met Met Met Lys Ala Leu Lys Trp Arg Leu Ser Pro Leu Thr
1               5                   10                  15

Ile Val Ser Trp
            20

<210> SEQ ID NO 11
<211> LENGTH: 20
<212> TYPE: PRT
<213> ORGANISM: Mus musculus

<400> SEQUENCE: 11

Glu Leu Met Met Met Lys Ala Leu Lys Trp Arg Leu Ser Pro Leu Thr
1               5                   10                  15

Ile Val Ser Trp
            20

<210> SEQ ID NO 12
<211> LENGTH: 20
<212> TYPE: PRT
<213> ORGANISM: Mus musculus

<400> SEQUENCE: 12

Glu Leu Met Met Met Lys Ala Leu Lys Trp Arg Leu Ser Pro Leu Thr
1               5                   10                  15

Ile Val Ser Trp
            20

<210> SEQ ID NO 13
<211> LENGTH: 20
<212> TYPE: PRT
<213> ORGANISM: Homo sapiens

<400> SEQUENCE: 13

Glu Leu Met Ile Met Lys Ala Leu Lys Trp Arg Leu Ser Pro Leu Thr
1               5                   10                  15

Ile Val Ser Trp
            20

<210> SEQ ID NO 14
<211> LENGTH: 20
<212> TYPE: PRT
<213> ORGANISM: Homo sapiens

<400> SEQUENCE: 14

Glu Leu Met Ile Met Lys Ala Leu Lys Trp Arg Leu Ser Pro Leu Thr
1               5                   10                  15

Ile Val Ser Trp
            20

<210> SEQ ID NO 15
<211> LENGTH: 319
<212> TYPE: PRT
<213> ORGANISM: Mus musculus

<400> SEQUENCE: 15

Met Asp Leu Ser Ala Ile Tyr Glu Ser Leu Gln Ser Met Ser His Asp
1               5                   10                  15

Leu Ser Ser Asp His Gly Gly Thr Glu Ser Leu Gly Gly Leu Trp Asn
                20                  25                  30

Ile Asn Ser Asp Ser Ile Pro Ser Gly Val Thr Ser Arg Leu Thr Gly
            35                  40                  45

-continued

```
Arg Ser Thr Ser Leu Val Glu Gly Arg Ser Cys Gly Trp Val Pro Pro
 50                  55                  60

Pro Pro Gly Phe Ala Pro Leu Ala Pro Arg Pro Gly Pro Glu Leu Ser
 65                  70                  75                  80

Pro Ser Pro Thr Ser Pro Thr Ala Thr Pro Thr Thr Ser Ser Arg Tyr
                 85                  90                  95

Lys Thr Glu Leu Cys Arg Thr Tyr Ser Glu Ser Gly Arg Cys Arg Tyr
                100                 105                 110

Gly Ala Lys Cys Gln Phe Ala His Gly Leu Gly Glu Leu Arg Gln Ala
                115                 120                 125

Asn Arg His Pro Lys Tyr Lys Thr Glu Leu Cys His Lys Phe Tyr Leu
130                 135                 140

Gln Gly Arg Cys Pro Tyr Gly Ser Arg Cys His Phe Ile His Asn Pro
145                 150                 155                 160

Thr Glu Asp Leu Ala Leu Pro Gly Gln Pro His Val Leu Arg Gln Ser
                165                 170                 175

Ile Ser Phe Ser Gly Leu Pro Ser Gly Arg Arg Ser Ser Pro Pro Pro
                180                 185                 190

Pro Gly Phe Ser Gly Pro Ser Leu Ser Ser Cys Ser Phe Ser Pro Ser
                195                 200                 205

Ser Ser Pro Pro Pro Gly Asp Leu Pro Leu Ser Pro Ser Ala Phe
210                 215                 220

Ser Ala Ala Pro Gly Thr Pro Val Thr Arg Arg Asp Pro Asn Gln Ala
225                 230                 235                 240

Cys Cys Pro Ser Cys Arg Arg Ser Thr Thr Pro Ser Thr Ile Trp Gly
                245                 250                 255

Pro Leu Gly Gly Leu Ala Arg Ser Pro Ser Ala His Ser Leu Gly Ser
                260                 265                 270

Asp Pro Asp Asp Tyr Ala Ser Ser Gly Ser Ser Leu Gly Gly Ser Asp
                275                 280                 285

Ser Pro Val Phe Glu Ala Gly Val Phe Gly Pro Pro Gln Thr Pro Ala
                290                 295                 300

Pro Pro Arg Arg Leu Pro Ile Phe Asn Arg Ile Ser Val Ser Glu
305                 310                 315

<210> SEQ ID NO 16
<211> LENGTH: 326
<212> TYPE: PRT
<213> ORGANISM: Homo sapiens

<400> SEQUENCE: 16

Met Asp Leu Thr Ala Ile Tyr Glu Ser Leu Leu Ser Leu Ser Pro Asp
1                   5                   10                  15

Val Pro Val Pro Ser Asp His Gly Gly Thr Glu Ser Ser Pro Gly Trp
                20                  25                  30

Gly Ser Ser Gly Pro Trp Ser Leu Ser Pro Ser Asp Ser Ser Pro Ser
                35                  40                  45

Gly Val Thr Ser Arg Leu Pro Gly Arg Ser Thr Ser Leu Val Glu Gly
                50                  55                  60

Arg Ser Cys Gly Trp Val Pro Pro Pro Gly Phe Ala Pro Leu Ala
65                  70                  75                  80

Pro Arg Leu Gly Pro Glu Leu Ser Pro Ser Thr Ser Pro Thr Ala
                85                  90                  95

Thr Ser Thr Thr Pro Ser Arg Tyr Lys Thr Glu Leu Cys Arg Thr Phe
```

```
                    100                 105                 110
Ser Glu Ser Gly Arg Cys Arg Tyr Gly Ala Lys Cys Gln Phe Ala His
            115                 120                 125

Gly Leu Gly Glu Leu Arg Gln Ala Asn Arg His Pro Lys Tyr Lys Thr
        130                 135                 140

Glu Leu Cys His Lys Phe Tyr Leu Gln Gly Arg Cys Pro Tyr Gly Ser
145                 150                 155                 160

Arg Cys His Phe Ile His Asn Pro Ser Glu Asp Leu Ala Ala Pro Gly
                165                 170                 175

His Pro Pro Val Leu Arg Gln Ser Ile Ser Phe Ser Gly Leu Pro Ser
            180                 185                 190

Gly Arg Arg Thr Ser Pro Pro Pro Gly Leu Ala Gly Pro Ser Leu
        195                 200                 205

Ser Ser Ser Ser Phe Ser Pro Ser Ser Pro Pro Pro Gly Asp
210                 215                 220

Leu Pro Leu Ser Pro Ser Ala Phe Ser Ala Ala Pro Gly Thr Pro Leu
225                 230                 235                 240

Ala Arg Arg Asp Pro Thr Pro Val Cys Cys Pro Ser Cys Arg Arg Ala
                245                 250                 255

Thr Pro Ile Ser Val Trp Gly Pro Leu Gly Gly Leu Val Arg Thr Pro
                260                 265                 270

Ser Val Gln Ser Leu Gly Ser Asp Pro Asp Glu Tyr Ala Ser Ser Gly
            275                 280                 285

Ser Ser Leu Gly Gly Ser Asp Ser Pro Val Phe Glu Ala Gly Val Phe
        290                 295                 300

Ala Pro Pro Gln Pro Val Ala Ala Pro Arg Arg Leu Pro Ile Phe Asn
305                 310                 315                 320

Arg Ile Ser Val Ser Glu
            325

<210> SEQ ID NO 17
<211> LENGTH: 355
<212> TYPE: PRT
<213> ORGANISM: Homo sapiens

<400> SEQUENCE: 17

Met Pro Phe Leu Gly Gln Asp Trp Arg Ser Pro Gly Gln Asn Trp Val
1               5                   10                  15

Lys Thr Ala Asp Gly Trp Lys Arg Phe Leu Asp Glu Lys Ser Gly Ser
            20                  25                  30

Phe Val Ser Asp Leu Ser Ser Tyr Cys Asn Lys Glu Val Tyr Asn Lys
        35                  40                  45

Glu Asn Leu Phe Asn Ser Leu Asn Tyr Asp Val Ala Ala Lys Lys Arg
    50                  55                  60

Lys Lys Asp Met Leu Asn Ser Lys Thr Lys Thr Gln Tyr Phe His Gln
65                  70                  75                  80

Glu Lys Trp Ile Tyr Val His Lys Gly Ser Thr Lys Glu Arg His Gly
                85                  90                  95

Tyr Cys Thr Leu Gly Glu Ala Phe Asn Arg Leu Asp Phe Ser Thr Ala
            100                 105                 110

Ile Leu Asp Ser Arg Arg Phe Asn Tyr Val Val Arg Leu Leu Glu Leu
        115                 120                 125

Ile Ala Lys Ser Gln Leu Thr Ser Leu Ser Gly Ile Ala Gln Lys Asn
    130                 135                 140
```

```
Phe Met Asn Ile Leu Glu Lys Val Val Leu Lys Val Leu Glu Asp Gln
145                 150                 155                 160

Gln Asn Ile Arg Leu Ile Arg Glu Leu Leu Gln Thr Leu Tyr Thr Ser
            165                 170                 175

Leu Cys Thr Leu Val Gln Arg Val Gly Lys Ser Val Leu Val Gly Asn
            180                 185                 190

Ile Asn Met Trp Val Tyr Arg Met Glu Thr Ile Leu His Trp Gln Gln
            195                 200                 205

Gln Leu Asn Asn Ile Gln Ile Thr Arg Pro Ala Phe Lys Gly Leu Thr
            210                 215                 220

Phe Thr Asp Leu Pro Leu Cys Leu Gln Leu Asn Ile Met Gln Arg Leu
225                 230                 235                 240

Ser Asp Gly Arg Asp Leu Val Ser Leu Gly Gln Ala Ala Pro Asp Leu
            245                 250                 255

His Val Leu Ser Glu Asp Arg Leu Leu Trp Lys Lys Leu Cys Gln Tyr
            260                 265                 270

His Phe Ser Glu Arg Gln Ile Arg Lys Arg Leu Ile Leu Ser Asp Lys
            275                 280                 285

Gly Gln Leu Asp Trp Lys Lys Met Tyr Phe Lys Leu Val Arg Cys Tyr
290                 295                 300

Pro Arg Lys Glu Gln Tyr Gly Asp Thr Leu Gln Leu Cys Lys His Cys
305                 310                 315                 320

His Ile Leu Ser Trp Lys Gly Thr Asp His Pro Cys Thr Ala Asn Asn
            325                 330                 335

Pro Glu Ser Cys Ser Val Ser Leu Ser Pro Gln Asp Phe Ile Asn Leu
            340                 345                 350

Phe Lys Phe
        355

<210> SEQ ID NO 18
<211> LENGTH: 355
<212> TYPE: PRT
<213> ORGANISM: Mus musculus

<400> SEQUENCE: 18

Met Pro Phe Leu Gly Gln Asp Trp Arg Ser Pro Gly Gln Ser Trp Val
1               5                   10                  15

Lys Thr Ala Asp Gly Trp Lys Arg Phe Leu Asp Glu Lys Ser Gly Ser
            20                  25                  30

Phe Val Ser Asp Leu Ser Ser Tyr Cys Asn Lys Glu Val Tyr Ser Lys
            35                  40                  45

Glu Asn Leu Phe Ser Ser Leu Asn Tyr Asp Val Ala Ala Lys Lys Arg
50                  55                  60

Lys Lys Asp Ile Gln Asn Ser Lys Thr Lys Thr Gln Tyr Phe His Gln
65                  70                  75                  80

Glu Lys Trp Ile Tyr Val His Lys Gly Ser Thr Lys Glu Arg His Gly
            85                  90                  95

Tyr Cys Thr Leu Gly Glu Ala Phe Asn Arg Leu Asp Phe Ser Thr Ala
            100                 105                 110

Ile Leu Asp Ser Arg Arg Phe Asn Tyr Val Val Arg Leu Leu Glu Leu
            115                 120                 125

Ile Ala Lys Ser Gln Leu Thr Ser Leu Ser Gly Ile Ala Gln Lys Asn
            130                 135                 140

Phe Met Asn Ile Leu Glu Lys Val Val Leu Lys Val Leu Glu Asp Gln
145                 150                 155                 160
```

```
Gln Asn Ile Arg Leu Ile Arg Glu Leu Leu Gln Thr Leu Tyr Thr Ser
                165                 170                 175
Leu Cys Thr Leu Val Gln Arg Val Gly Lys Ser Val Leu Val Gly Asn
            180                 185                 190
Ile Asn Met Trp Val Tyr Arg Met Glu Thr Ile Leu His Trp Gln Gln
        195                 200                 205
Gln Leu Asn Ser Ile Gln Ile Ser Arg Pro Ala Phe Lys Gly Leu Thr
    210                 215                 220
Ile Thr Asp Leu Pro Val Cys Leu Gln Leu Asn Ile Met Gln Arg Leu
225                 230                 235                 240
Ser Asp Gly Arg Asp Leu Val Ser Leu Gly Gln Ala Ala Pro Asp Leu
                245                 250                 255
His Val Leu Ser Glu Asp Arg Leu Leu Trp Lys Arg Leu Cys Gln Tyr
            260                 265                 270
His Phe Ser Glu Arg Gln Ile Arg Lys Arg Leu Ile Leu Ser Asp Lys
        275                 280                 285
Gly Gln Leu Asp Trp Lys Lys Met Tyr Phe Lys Leu Val Arg Cys Tyr
    290                 295                 300
Pro Arg Arg Glu Gln Tyr Gly Val Thr Leu Gln Leu Cys Lys His Cys
305                 310                 315                 320
His Ile Leu Ser Trp Lys Gly Thr Asp His Pro Cys Thr Ala Asn Asn
                325                 330                 335
Pro Glu Ser Cys Ser Val Ser Leu Ser Pro Gln Asp Phe Ile Asn Leu
            340                 345                 350
Phe Lys Phe
        355

<210> SEQ ID NO 19
<211> LENGTH: 361
<212> TYPE: PRT
<213> ORGANISM: Mus musculus

<400> SEQUENCE: 19

Met Ala Ser Pro Ala Val Pro Ala Asn Val Pro Pro Ala Thr Ala Ala
1               5                   10                  15
Ala Ala Pro Ala Pro Val Val Thr Ala Ala Pro Ala Ser Ala Pro Thr
            20                  25                  30
Pro Ser Thr Pro Ala Pro Thr Pro Ala Ala Thr Pro Ala Ala Ser Pro
        35                  40                  45
Ala Pro Val Ser Ser Asp Pro Ala Val Ala Ala Pro Ala Ala Pro Gly
    50                  55                  60
Gln Thr Pro Ala Ser Ala Pro Ala Pro Gln Thr Pro Ala Pro Ala Ser
65                  70                  75                  80
Gln Pro Gly Pro Ala Leu Pro Gly Pro Phe Pro Gly Gly Arg Val Val
                85                  90                  95
Arg Leu His Pro Val Ile Leu Ala Ser Ile Val Asp Ser Tyr Glu Arg
            100                 105                 110
Arg Asn Glu Gly Ala Ala Arg Val Ile Gly Thr Leu Leu Gly Thr Val
        115                 120                 125
Asp Lys His Ser Val Glu Val Thr Asn Cys Phe Ser Val Pro His Asn
    130                 135                 140
Glu Ser Glu Asp Glu Val Ala Val Asp Met Glu Phe Ala Lys Asn Met
145                 150                 155                 160
Tyr Glu Leu His Lys Lys Val Ser Pro Asn Glu Leu Ile Leu Gly Trp
```

```
            165                 170                 175
Tyr Ala Thr Gly His Asp Ile Thr Glu His Ser Val Leu Ile His Glu
        180                 185                 190

Tyr Tyr Ser Arg Glu Ala Pro Asn Pro Ile His Leu Thr Val Asp Thr
        195                 200                 205

Gly Leu Gln His Gly Arg Met Ser Ile Lys Ala Tyr Val Ser Thr Leu
        210                 215                 220

Met Gly Val Pro Gly Arg Thr Met Gly Val Met Phe Thr Pro Leu Thr
225                 230                 235                 240

Val Lys Tyr Ala Tyr Tyr Asp Thr Glu Arg Ile Gly Val Asp Leu Ile
                245                 250                 255

Met Lys Thr Cys Phe Ser Pro Asn Arg Val Ile Gly Leu Ser Ser Asp
                260                 265                 270

Leu Gln Gln Val Gly Gly Ala Ser Ala Arg Ile Gln Asp Ala Leu Ser
            275                 280                 285

Thr Val Leu Gln Tyr Ala Glu Asp Val Leu Ser Gly Lys Val Ser Ala
        290                 295                 300

Asp Asn Thr Val Gly Arg Phe Leu Met Ser Leu Val Asn Gln Val Pro
305                 310                 315                 320

Lys Ile Val Pro Asp Asp Phe Glu Thr Met Leu Asn Ser Asn Ile Asn
                325                 330                 335

Asp Leu Leu Met Val Thr Tyr Leu Ala Asn Leu Thr Gln Ser Gln Ile
                340                 345                 350

Ala Leu Asn Glu Lys Leu Val Asn Leu
            355                 360

<210> SEQ ID NO 20
<211> LENGTH: 298
<212> TYPE: PRT
<213> ORGANISM: Homo sapiens

<400> SEQUENCE: 20

Gly Gln Thr Pro Ala Ser Ala Gln Ala Pro Ala Gln Thr Pro Ala Pro
1               5                   10                  15

Ala Leu Pro Gly Pro Ala Leu Pro Gly Pro Phe Pro Gly Gly Arg Val
                20                  25                  30

Val Arg Leu His Pro Val Ile Leu Ala Ser Ile Val Asp Ser Tyr Glu
            35                  40                  45

Arg Arg Asn Glu Gly Ala Ala Arg Val Ile Gly Thr Leu Leu Gly Thr
        50                  55                  60

Val Asp Lys His Ser Val Glu Val Thr Asn Cys Phe Ser Val Pro His
65                  70                  75                  80

Asn Glu Ser Glu Asp Glu Val Ala Val Asp Met Glu Phe Ala Lys Asn
                85                  90                  95

Met Tyr Glu Leu His Lys Lys Val Ser Pro Asn Glu Leu Ile Leu Gly
                100                 105                 110

Trp Tyr Ala Thr Gly His Asp Ile Thr Glu His Ser Val Leu Ile His
            115                 120                 125

Glu Tyr Tyr Ser Arg Glu Ala Pro Asn Pro Ile His Leu Thr Val Asp
        130                 135                 140

Thr Ser Leu Gln Asn Gly Arg Met Ser Ile Lys Ala Tyr Val Ser Thr
145                 150                 155                 160

Leu Met Gly Val Pro Gly Arg Thr Met Gly Val Met Phe Thr Pro Leu
                165                 170                 175
```

Thr Val Lys Tyr Ala Tyr Asp Thr Glu Arg Ile Gly Val Asp Leu
            180                 185                 190

Ile Met Lys Thr Cys Phe Ser Pro Asn Arg Val Ile Gly Leu Ser Ser
        195                 200                 205

Asp Leu Gln Gln Val Gly Gly Ala Ser Ala Arg Ile Gln Asp Ala Leu
    210                 215                 220

Ser Thr Val Leu Gln Tyr Ala Glu Asp Val Leu Ser Gly Lys Val Ser
225                 230                 235                 240

Ala Asp Asn Thr Val Gly Arg Phe Leu Met Ser Leu Val Asn Gln Val
            245                 250                 255

Pro Lys Ile Val Pro Asp Asp Phe Glu Thr Met Leu Asn Ser Asn Ile
        260                 265                 270

Asn Asp Leu Leu Met Val Thr Tyr Leu Ala Asn Leu Thr Gln Ser Gln
    275                 280                 285

Ile Ala Leu Asn Glu Lys Leu Val Asn Leu
    290                 295

<210> SEQ ID NO 21
<211> LENGTH: 206
<212> TYPE: PRT
<213> ORGANISM: Homo sapiens

<400> SEQUENCE: 21

Met Asn Phe Gln Gln Arg Leu Gln Ser Leu Trp Thr Leu Ala Arg Pro
1               5                   10                  15

Phe Cys Pro Pro Leu Leu Ala Thr Ala Ser Gln Met Gln Met Val Val
            20                  25                  30

Leu Pro Cys Leu Gly Phe Thr Leu Leu Leu Trp Ser Gln Val Ser Gly
        35                  40                  45

Ala Gln Gly Gln Glu Phe His Phe Gly Pro Cys Gln Val Lys Gly Val
    50                  55                  60

Val Pro Gln Lys Leu Trp Glu Ala Phe Trp Ala Val Lys Asp Thr Met
65                  70                  75                  80

Gln Ala Gln Asp Asn Ile Thr Ser Ala Arg Leu Leu Gln Gln Glu Val
            85                  90                  95

Leu Gln Asn Val Ser Asp Ala Glu Ser Cys Tyr Leu Val His Thr Leu
        100                 105                 110

Leu Glu Phe Tyr Leu Lys Thr Val Phe Lys Asn Tyr His Asn Arg Thr
    115                 120                 125

Val Glu Val Arg Thr Leu Lys Ser Phe Ser Thr Leu Ala Asn Asn Phe
130                 135                 140

Val Leu Ile Val Ser Gln Leu Gln Pro Ser Gln Glu Asn Glu Met Phe
145                 150                 155                 160

Ser Ile Arg Asp Ser Ala His Arg Arg Phe Leu Leu Phe Arg Arg Ala
            165                 170                 175

Phe Lys Gln Leu Asp Val Glu Ala Ala Leu Thr Lys Ala Leu Gly Glu
        180                 185                 190

Val Asp Ile Leu Leu Thr Trp Met Gln Lys Phe Tyr Lys Leu
    195                 200                 205

<210> SEQ ID NO 22
<211> LENGTH: 164
<212> TYPE: PRT
<213> ORGANISM: Mus musculus

<400> SEQUENCE: 22

Trp Asn Gln Val Pro Gly Leu Glu Gly Gln Phe Arg Phe Gly Ser
1               5                   10                  15

Cys Gln Val Thr Gly Val Val Leu Pro Glu Leu Trp Glu Ala Phe Trp
                20                  25                  30

Thr Val Lys Asn Thr Val Gln Thr Gln Asp Asp Ile Thr Ser Ile Arg
                35                  40                  45

Leu Leu Lys Pro Gln Val Leu Arg Asn Val Ser Gly Ala Glu Ser Cys
    50                  55                  60

Tyr Leu Ala His Ser Leu Leu Lys Phe Tyr Leu Asn Thr Val Phe Lys
65                  70                  75                  80

Asn Tyr His Ser Lys Ile Ala Lys Phe Lys Val Leu Arg Ser Phe Ser
                85                  90                  95

Thr Leu Ala Asn Asn Phe Ile Val Ile Met Ser Gln Leu Gln Pro Ser
                100                 105                 110

Lys Asp Asn Ser Met Leu Pro Ile Ser Glu Ser Ala His Gln Arg Phe
                115                 120                 125

Leu Leu Phe Arg Arg Ala Phe Lys Gln Leu Asp Thr Glu Val Ala Leu
    130                 135                 140

Val Lys Ala Phe Gly Glu Val Asp Ile Leu Leu Thr Trp Met Gln Lys
145                 150                 155                 160

Phe Tyr His Leu

<210> SEQ ID NO 23
<211> LENGTH: 154
<212> TYPE: PRT
<213> ORGANISM: Homo sapiens

<400> SEQUENCE: 23

Met Asn Phe Gln Gln Arg Leu Gln Ser Leu Trp Thr Leu Ala Ser Arg
1               5                   10                  15

Pro Phe Cys Pro Pro Leu Leu Ala Thr Ala Ser Gln Met Gln Met Val
                20                  25                  30

Val Leu Pro Cys Leu Gly Phe Thr Leu Leu Leu Trp Ser Gln Val Ser
                35                  40                  45

Gly Ala Gln Gly Gln Glu Phe His Phe Gly Pro Cys Gln Val Lys Gly
    50                  55                  60

Val Val Pro Gln Lys Leu Trp Glu Ala Phe Trp Ala Val Lys Asp Thr
65                  70                  75                  80

Met Gln Ala Gln Asp Asn Ile Thr Ser Ala Arg Leu Leu Gln Gln Glu
                85                  90                  95

Val Leu Gln Asn Val Ser Gln Glu Asn Glu Met Phe Ser Ile Arg Asp
                100                 105                 110

Ser Ala His Arg Arg Phe Leu Leu Phe Arg Arg Ala Phe Lys Gln Leu
                115                 120                 125

Asp Val Glu Ala Ala Leu Thr Lys Ala Leu Gly Glu Val Asp Ile Leu
    130                 135                 140

Leu Thr Trp Met Gln Lys Phe Tyr Lys Leu
145                 150

<210> SEQ ID NO 24
<211> LENGTH: 784
<212> TYPE: PRT
<213> ORGANISM: Homo sapiens

<400> SEQUENCE: 24

Met Gln Arg Leu Met Met Leu Leu Ala Thr Ser Gly Ala Cys Leu Gly

-continued

```
1               5                   10                  15
Leu Leu Ala Val Ala Ala Val Ala Ala Gly Ala Asn Pro Ala Gln
                20                  25                  30

Arg Asp Thr His Ser Leu Leu Pro Thr His Arg Arg Gln Lys Arg Asp
                35                  40                  45

Trp Ile Trp Asn Gln Met His Ile Asp Glu Glu Lys Asn Thr Ser Leu
    50                      55                      60

Pro His His Val Gly Lys Ile Lys Ser Ser Val Ser Arg Lys Asn Ala
65                      70                      75                  80

Lys Tyr Leu Leu Lys Gly Glu Tyr Val Gly Lys Val Phe Arg Val Asp
                    85                  90                  95

Ala Glu Thr Gly Asp Val Phe Ala Ile Glu Arg Leu Asp Arg Glu Asn
                100                     105                 110

Ile Ser Glu Tyr His Leu Thr Ala Val Ile Val Asp Lys Asp Thr Gly
                115                     120                 125

Glu Asn Leu Glu Thr Pro Ser Ser Phe Thr Ile Lys Val His Asp Val
            130                     135                 140

Asn Asp Asn Trp Pro Val Phe Thr His Arg Leu Phe Asn Ala Ser Val
145                     150                     155                 160

Pro Glu Ser Ser Ala Val Gly Thr Ser Val Ile Ser Val Thr Ala Val
                    165                     170                 175

Asp Ala Asp Asp Pro Thr Val Gly Asp His Ala Ser Val Met Tyr Gln
                180                     185                 190

Ile Leu Lys Gly Lys Glu Tyr Phe Ala Ile Asp Asn Ser Gly Arg Ile
                195                     200                 205

Ile Thr Ile Thr Lys Ser Leu Asp Arg Glu Lys Gln Ala Arg Tyr Glu
            210                     215                 220

Ile Val Val Glu Ala Arg Asp Ala Gln Gly Leu Arg Gly Asp Ser Gly
225                     230                     235                 240

Thr Ala Thr Val Leu Val Thr Leu Gln Asp Ile Asn Asp Asn Phe Pro
                    245                     250                 255

Phe Phe Thr Gln Thr Lys Tyr Thr Phe Val Val Pro Glu Asp Thr Arg
                260                     265                 270

Val Gly Thr Ser Val Gly Ser Leu Phe Val Glu Asp Pro Asp Glu Pro
                275                     280                 285

Gln Asn Arg Met Thr Lys Tyr Ser Ile Leu Arg Gly Asp Tyr Gln Asp
            290                     295                 300

Ala Phe Thr Ile Glu Thr Asn Pro Ala His Asn Glu Gly Ile Ile Lys
305                     310                     315                 320

Pro Met Lys Pro Leu Asp Tyr Glu Tyr Ile Gln Gln Tyr Ser Phe Ile
                    325                     330                 335

Val Glu Ala Thr Asp Pro Thr Ile Asp Leu Arg Tyr Met Ser Pro Pro
                340                     345                 350

Ala Gly Asn Arg Ala Gln Val Ile Ile Asn Ile Thr Asp Val Asp Glu
                355                     360                 365

Pro Pro Ile Phe Gln Gln Pro Phe Tyr His Phe Gln Leu Lys Glu Asn
            370                     375                 380

Gln Lys Lys Pro Leu Ile Gly Thr Val Leu Ala Met Asp Pro Asp Ala
385                     390                     395                 400

Ala Arg His Ser Ile Gly Tyr Ser Ile Arg Arg Thr Ser Asp Lys Gly
                    405                     410                 415

Gln Phe Phe Arg Val Thr Lys Lys Gly Asp Ile Tyr Asn Glu Lys Glu
                420                     425                 430
```

```
Leu Asp Arg Glu Val Tyr Pro Trp Tyr Asn Leu Thr Val Glu Ala Lys
        435                 440                 445

Glu Leu Asp Ser Thr Gly Thr Pro Thr Gly Lys Glu Ser Ile Val Gln
450                 455                 460

Val His Ile Glu Val Leu Asp Glu Asn Asp Asn Ala Pro Glu Phe Ala
465                 470                 475                 480

Lys Pro Tyr Gln Pro Lys Val Cys Glu Asn Ala Val His Gly Gln Leu
                485                 490                 495

Val Leu Gln Ile Ser Ala Ile Asp Lys Asp Ile Thr Pro Arg Asn Val
            500                 505                 510

Lys Phe Lys Phe Thr Leu Asn Thr Glu Asn Asn Phe Thr Leu Thr Asp
        515                 520                 525

Asn His Asp Asn Thr Ala Asn Ile Thr Val Lys Tyr Gly Gln Phe Asp
    530                 535                 540

Arg Glu His Thr Lys Val His Phe Leu Pro Val Val Ile Ser Asp Asn
545                 550                 555                 560

Gly Met Pro Ser Arg Thr Gly Thr Ser Thr Leu Thr Val Ala Val Cys
                565                 570                 575

Lys Cys Asn Glu Gln Gly Glu Phe Thr Phe Cys Glu Asp Met Ala Ala
            580                 585                 590

Gln Val Gly Val Ser Ile Gln Ala Val Val Ala Ile Leu Leu Cys Ile
        595                 600                 605

Leu Thr Ile Thr Val Ile Thr Leu Leu Ile Phe Leu Arg Arg Arg Leu
    610                 615                 620

Arg Lys Gln Ala Arg Ala His Gly Lys Ser Val Pro Glu Ile His Glu
625                 630                 635                 640

Gln Leu Val Thr Tyr Asp Glu Glu Gly Gly Gly Glu Met Asp Thr Thr
                645                 650                 655

Ser Tyr Asp Val Ser Val Leu Asn Ser Val Arg Arg Gly Gly Ala Lys
            660                 665                 670

Pro Pro Arg Pro Ala Leu Asp Ala Arg Pro Ser Leu Tyr Ala Gln Val
        675                 680                 685

Gln Lys Pro Pro Arg His Ala Pro Gly Ala His Gly Gly Pro Gly Glu
    690                 695                 700

Met Ala Ala Met Ile Glu Val Lys Lys Asp Glu Ala Asp His Asp Gly
705                 710                 715                 720

Asp Gly Pro Pro Tyr Asp Thr Leu His Ile Tyr Gly Tyr Glu Gly Ser
                725                 730                 735

Glu Ser Ile Ala Glu Ser Leu Ser Ser Leu Gly Thr Asp Ser Ser Asp
            740                 745                 750

Ser Asp Val Asp Tyr Asp Phe Leu Asn Asp Trp Gly Pro Arg Phe Lys
        755                 760                 765

Met Leu Ala Glu Leu Tyr Gly Ser Asp Pro Arg Glu Glu Leu Leu Tyr
    770                 775                 780

<210> SEQ ID NO 25
<211> LENGTH: 9
<212> TYPE: PRT
<213> ORGANISM: Homo sapiens
<220> FEATURE:
<221> NAME/KEY: SITE
<222> LOCATION: (5)..(5)
<223> OTHER INFORMATION: tyrosine Y685 is phosphorylated by src kinase

<400> SEQUENCE: 25
```

Arg Pro Ser Leu Tyr Ala Gln Val Gln
1               5

<210> SEQ ID NO 26
<211> LENGTH: 393
<212> TYPE: PRT
<213> ORGANISM: Homo sapiens

<400> SEQUENCE: 26

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
            130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
            275                 280                 285

Leu Arg Lys Lys Gly Glu Pro His His Glu Leu Pro Pro Gly Ser Thr
            290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 27
<211> LENGTH: 320
<212> TYPE: PRT
<213> ORGANISM: Homo sapiens

<400> SEQUENCE: 27

Met Pro Lys Pro Ile Asn Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Tyr Phe Gly Leu His
        35                  40                  45

Tyr Val Asp Asn Lys Gly Phe Pro Thr Trp Leu Lys Leu Asp Lys Lys
50                  55                  60

Val Ser Ala Gln Glu Val Arg Lys Glu Asn Pro Leu Gln Phe Lys Phe
65                  70                  75                  80

Arg Ala Lys Phe Tyr Pro Glu Asp Val Ala Glu Leu Ile Gln Asp
                85                  90                  95

Ile Thr Gln Lys Leu Phe Phe Leu Gln Val Lys Glu Gly Ile Leu Ser
            100                 105                 110

Asp Glu Ile Tyr Cys Pro Pro Glu Thr Ala Val Leu Leu Gly Ser Tyr
        115                 120                 125

Ala Val Gln Ala Lys Phe Gly Asp Tyr Asn Lys Glu Val His Lys Ser
130                 135                 140

Gly Tyr Leu Ser Ser Glu Arg Leu Ile Pro Gln Arg Val Met Asp Gln
145                 150                 155                 160

His Lys Leu Thr Arg Asp Gln Trp Glu Asp Arg Ile Gln Val Trp His
                165                 170                 175

Ala Glu His Arg Gly Met Leu Lys Asp Asn Ala Met Leu Glu Tyr Leu
            180                 185                 190

Lys Ile Ala Gln Asp Leu Glu Met Tyr Gly Ile Asn Tyr Phe Glu Ile
        195                 200                 205

Lys Asn Lys Lys Gly Thr Asp Leu Trp Leu Gly Val Asp Ala Leu Gly
210                 215                 220

Leu Asn Ile Tyr Glu Lys Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Gln Leu Cys Met Gly Asn His
        275                 280                 285

Glu Leu Tyr Met Arg Arg Arg Lys Pro Asp Thr Ile Glu Val Gln Gln
290                 295                 300

Met Lys Ala Gln Ala Arg Glu Glu Lys His Gln Lys Gln Leu Glu Arg
305                 310                 315                 320

<210> SEQ ID NO 28
<211> LENGTH: 200
<212> TYPE: PRT

<213> ORGANISM: Artificial sequence
<220> FEATURE:
<223> OTHER INFORMATION: Human protein derivative

<400> SEQUENCE: 28

```
Met His His His His His His His Lys Arg Tyr Lys Asn Arg Val
1               5                   10                  15

Ala Ser Arg Lys Cys Arg Ala Lys Phe Lys Gln Leu Leu Gln His Tyr
            20                  25                  30

Arg Glu Val Ala Ala Lys Ser Ser Glu Asn Asp Arg Leu Arg Leu
        35                  40                  45

Leu Leu Lys Gln Met Cys Lys Leu Ala Lys Phe Val Ala Ala Trp Thr
50                  55                  60

Leu Lys Ala Ala Ala Gly Ser Asp Glu Val Ser Gly Leu Glu Gln Leu
65                  70                  75                  80

Glu Ser Ile Ile Asn Phe Glu Lys Leu Thr Glu Trp Thr Ser Ser Asn
                85                  90                  95

Val Met Glu Glu Arg Lys Ile Lys Val Tyr Leu Pro Arg Met Lys Met
            100                 105                 110

Glu Glu Lys Tyr Asn Leu Thr Ser Val Leu Met Ala Met Gly Ile Thr
        115                 120                 125

Asp Val Phe Ser Ser Ser Ala Asn Leu Ser Gly Ile Ser Ser Ala Glu
    130                 135                 140

Ser Leu Lys Ile Ser Gln Ala Val His Ala Ala His Ala Glu Ile Asn
145                 150                 155                 160

Glu Ala Gly Arg Glu Val Val Gly Ser Ala Glu Ala Gly Val Asp Ala
                165                 170                 175

Ala Ser Val Ser Glu Glu Phe Arg Ala Asp His Pro Phe Leu Phe Cys
            180                 185                 190

Ile Lys His Ile Ala Thr Asn Ala
        195                 200
```

<210> SEQ ID NO 29
<211> LENGTH: 349
<212> TYPE: PRT
<213> ORGANISM: Artificial sequence
<220> FEATURE:
<223> OTHER INFORMATION: Human protein derivative

<400> SEQUENCE: 29

```
Glu Cys Asp Ser Glu Leu Glu Ile Lys Arg Tyr Lys Asn Arg Val Ala
1               5                   10                  15

Ser Arg Lys Cys Arg Ala Lys Phe Lys Gln Leu Leu Gln His Tyr Arg
            20                  25                  30

Glu Val Ala Ala Ala Lys Ser Ser Glu Asn Asp Arg Leu Arg Leu Leu
        35                  40                  45

Leu Lys Gln Met Arg His Met Gln Ser Ala Thr Arg Ala Thr Leu Val
50                  55                  60

Cys Gly Ser Gly Val Lys Gln Ile Ile Ala Lys Gly His Pro Asn Thr
65                  70                  75                  80

Arg Val Phe Gly Ala Arg Lys Ala Arg Ile Pro Glu Arg Glu Val Leu
                85                  90                  95

Ala Ala Lys Pro Lys Ile Thr Arg Ile Thr His Leu Asn Leu Gln Pro
            100                 105                 110

Gln Glu Arg Gln Ala Phe Tyr Arg Leu Leu Glu Asn Glu Leu Ile Gln
        115                 120                 125
```

```
Glu Phe Leu Ser Met Asp Ser Cys Leu Lys Ile Ser Asp Lys Tyr Leu
            130                 135                 140

Ile Ala Met Val Leu Ala Tyr Phe Lys Arg Ala Gly Leu Tyr Thr Gly
145                 150                 155                 160

Glu Tyr Thr Thr Met Asn Phe Phe Val Ala Leu Tyr Leu Ala Asn Asp
                165                 170                 175

Met Glu Glu Asp Glu Glu Asp Tyr Lys Tyr Glu Ile Phe Pro Trp Ala
            180                 185                 190

Leu Gly Asp Ser Trp Arg Glu Phe Pro Gln Phe Leu Arg Leu Arg
            195                 200                 205

Asp Asn Phe Trp Ala Lys Met Asn Tyr Arg Ala Val Val Ser Arg Arg
210                 215                 220

Cys Cys Asp Glu Val Met Ala Lys Asp Pro Thr His Trp Ala Trp Leu
225                 230                 235                 240

Arg Asp Arg Pro Ile His His Ser Gly Ala Leu Arg Gly Tyr Leu Arg
                245                 250                 255

Asn Glu Asp Asp Phe Phe Pro Arg Gly Pro Gly Leu Thr Pro Ala Ser
            260                 265                 270

Cys Ala Leu Cys His Lys Ala Ser Val Cys Asp Ser Gly Gly Val Ala
            275                 280                 285

His Asp Asn Ser Ser Pro Glu Gln Glu Ile Phe His Tyr Thr Asn Arg
290                 295                 300

Glu Trp Ser Gln Glu Leu Leu Ile Leu Pro Pro Glu Leu Leu Leu Asp
305                 310                 315                 320

Pro Glu Ser Thr Tyr Asp Ile His Ile Phe Gln Glu Pro Leu Val Gly
                325                 330                 335

Leu Glu Pro Asp Gly Ala Ala Leu Glu Trp His His Leu
            340                 345

<210> SEQ ID NO 30
<211> LENGTH: 182
<212> TYPE: PRT
<213> ORGANISM: Artificial sequence
<220> FEATURE:
<223> OTHER INFORMATION: Human protein derivative

<400> SEQUENCE: 30

Glu Cys Asp Ser Glu Leu Glu Ile Lys Arg Tyr Lys Asn Arg Val Ala
1               5                   10                  15

Ser Arg Lys Cys Arg Ala Lys Phe Lys Gln Leu Leu Gln His Tyr Arg
                20                  25                  30

Glu Val Ala Ala Lys Ser Ser Glu Asn Asp Arg Leu Arg Leu Leu
            35                  40                  45

Leu Lys Gln Gln Glu Val Gln Ala Phe Leu Ser Leu Leu Glu Asp Ser
50                  55                  60

Phe Val Gln Glu Phe Leu Ser Lys Asp Pro Cys Phe Gln Ile Ser Asp
65                  70                  75                  80

Lys Tyr Leu Leu Ala Met Val Leu Val Tyr Phe Gln Arg Ala His Leu
                85                  90                  95

Lys Leu Ser Glu Tyr Thr His Ser Ser Leu Phe Leu Ala Leu Tyr Leu
            100                 105                 110

Ala Asn Asp Met Glu Glu Asp Leu Glu Gly Pro Lys Cys Glu Ile Phe
            115                 120                 125

Pro Trp Ala Leu Gly Lys Asp Trp Cys Leu Arg Val Gly Lys Phe Leu
            130                 135                 140
```

```
His Gln Arg Asp Lys Leu Trp Ala Arg Met Gly Phe Arg Ala Val Val
145                 150                 155                 160

Ser Arg Gln Cys Cys Glu Glu Val Met Ala Lys Glu Pro Phe His Trp
                165                 170                 175

Ala Trp Thr Arg Asp Arg
            180

<210> SEQ ID NO 31
<211> LENGTH: 462
<212> TYPE: PRT
<213> ORGANISM: Artificial sequence
<220> FEATURE:
<223> OTHER INFORMATION: Human protein derivative

<400> SEQUENCE: 31

Glu Cys Asp Ser Glu Leu Glu Ile Lys Arg Tyr Lys Asn Arg Val Ala
1               5                   10                  15

Ser Arg Lys Cys Arg Ala Lys Phe Lys Gln Leu Leu Gln His Tyr Arg
                20                  25                  30

Glu Val Ala Ala Ala Lys Ser Ser Glu Asn Asp Arg Leu Arg Leu Leu
            35                  40                  45

Leu Lys Gln Met Pro Arg Glu Arg Lys Glu Arg Asp Ser Lys Asp His
50                  55                  60

Ser Asn Met Lys Glu Glu Gly Gly Ser Asp Leu Ser Val Arg Ser Arg
65                  70                  75                  80

Lys Arg Lys Ala Asn Val Ala Val Phe Leu Gln Asp Pro Asp Glu Glu
                85                  90                  95

Ile Ala Lys Ile Asp Lys Thr Val Lys Ser Gln Asp Ser Ser Gln Pro
            100                 105                 110

Trp Asp Asp Ser Ala Cys Val Asp Pro Cys Ser Phe Ile Pro Thr
        115                 120                 125

Pro Asn Lys Glu Glu Asp Asn Glu Leu Glu Tyr Pro Lys Thr Ala Phe
130                 135                 140

Gln Pro Arg Lys Ile Arg Pro Pro Arg Ala Ser Pro Leu Pro Val Leu
145                 150                 155                 160

Asn Trp Gly Asn Arg Glu Glu Val Trp Arg Ile Met Leu Asn Lys Glu
                165                 170                 175

Lys Thr Tyr Leu Arg Asp Glu His Phe Leu Gln Arg His Pro Leu Leu
            180                 185                 190

Gln Ala Arg Met Arg Ala Val Leu Leu Asp Trp Leu Met Glu Val Cys
        195                 200                 205

Glu Val Tyr Lys Leu His Arg Glu Thr Phe Tyr Leu Ala Gln Asp Phe
    210                 215                 220

Phe Asp Arg Tyr Met Ala Ser Gln Gln Asn Ile Ile Lys Thr Leu Leu
225                 230                 235                 240

Gln Leu Ile Gly Ile Ser Ala Leu Phe Ile Ala Ser Lys Leu Glu Glu
                245                 250                 255

Ile Tyr Pro Pro Lys Leu His Gln Phe Ala Tyr Val Thr Asp Gly Ala
            260                 265                 270

Cys Ser Gly Asp Glu Ile Leu Thr Met Glu Leu Met Met Met Lys Ala
        275                 280                 285

Leu Lys Trp Arg Leu Ser Pro Leu Thr Ile Val Ser Trp Leu Asn Val
    290                 295                 300

Tyr Val Gln Val Ala Tyr Val Asn Asp Thr Gly Glu Val Leu Met Pro
305                 310                 315                 320
```

```
Gln Tyr Pro Gln Gln Val Phe Val Gln Ile Ala Glu Leu Leu Asp Leu
                325                 330                 335

Cys Val Leu Asp Val Gly Cys Leu Glu Phe Pro Tyr Gly Val Leu Ala
            340                 345                 350

Ala Ser Ala Leu Tyr His Phe Ser Leu Glu Leu Met Gln Lys Val
        355                 360                 365

Ser Gly Tyr Gln Trp Cys Asp Ile Glu Lys Cys Val Lys Trp Met Val
    370                 375                 380

Pro Phe Ala Met Val Ile Arg Glu Met Gly Ser Ser Lys Leu Lys His
385                 390                 395                 400

Phe Arg Gly Val Pro Met Glu Asp Ser His Asn Ile Gln Thr His Thr
                405                 410                 415

Asn Ser Leu Asp Leu Leu Asp Lys Ala Gln Ala Lys Lys Ala Ile Leu
            420                 425                 430

Ser Glu Gln Asn Arg Ile Ser Pro Pro Ser Gly Val Leu Thr Pro
        435                 440                 445

Pro His Ser Ser Lys Lys Gln Ser Ser Glu Gln Glu Thr Glu
    450                 455                 460

<210> SEQ ID NO 32
<211> LENGTH: 71
<212> TYPE: PRT
<213> ORGANISM: Artificial sequence
<220> FEATURE:
<223> OTHER INFORMATION: Human protein derivative

<400> SEQUENCE: 32

Glu Cys Asp Ser Glu Leu Glu Ile Lys Arg Tyr Lys Asn Arg Val Ala
1               5                   10                  15

Ser Arg Lys Cys Arg Ala Lys Phe Lys Gln Leu Leu Gln His Tyr Arg
            20                  25                  30

Glu Val Ala Ala Ala Lys Ser Ser Glu Asn Asp Arg Leu Arg Leu Leu
        35                  40                  45

Leu Lys Gln Glu Leu Met Ile Met Lys Ala Leu Lys Trp Arg Leu Ser
    50                  55                  60

Pro Leu Thr Ile Val Ser Trp
65                  70

<210> SEQ ID NO 33
<211> LENGTH: 377
<212> TYPE: PRT
<213> ORGANISM: Artificial sequence
<220> FEATURE:
<223> OTHER INFORMATION: Human protein derivative

<400> SEQUENCE: 33

Glu Cys Asp Ser Glu Leu Glu Ile Lys Arg Tyr Lys Asn Arg Val Ala
1               5                   10                  15

Ser Arg Lys Cys Arg Ala Lys Phe Lys Gln Leu Leu Gln His Tyr Arg
            20                  25                  30

Glu Val Ala Ala Ala Lys Ser Ser Glu Asn Asp Arg Leu Arg Leu Leu
        35                  40                  45

Leu Lys Gln Met Asp Leu Thr Ala Ile Tyr Glu Ser Leu Leu Ser Leu
    50                  55                  60

Ser Pro Asp Val Pro Val Pro Ser Asp His Gly Gly Thr Glu Ser Ser
65                  70                  75                  80

Pro Gly Trp Gly Ser Ser Gly Pro Trp Ser Leu Ser Pro Ser Asp Ser
            85                  90                  95
```

```
Ser Pro Ser Gly Val Thr Ser Arg Leu Pro Gly Arg Ser Thr Ser Leu
            100                 105                 110

Val Glu Gly Arg Ser Cys Gly Trp Val Pro Pro Pro Gly Phe Ala
            115                 120                 125

Pro Leu Ala Pro Arg Leu Gly Pro Glu Leu Ser Pro Ser Pro Thr Ser
130                 135                 140

Pro Thr Ala Thr Ser Thr Thr Pro Ser Arg Tyr Lys Thr Glu Leu Cys
145                 150                 155                 160

Arg Thr Phe Ser Glu Ser Gly Arg Cys Arg Tyr Gly Ala Lys Cys Gln
                165                 170                 175

Phe Ala His Gly Leu Gly Glu Leu Arg Gln Ala Asn Arg His Pro Lys
            180                 185                 190

Tyr Lys Thr Glu Leu Cys His Lys Phe Tyr Leu Gln Gly Arg Cys Pro
            195                 200                 205

Tyr Gly Ser Arg Cys His Phe Ile His Asn Pro Ser Glu Asp Leu Ala
210                 215                 220

Ala Pro Gly His Pro Pro Val Leu Arg Gln Ser Ile Ser Phe Ser Gly
225                 230                 235                 240

Leu Pro Ser Gly Arg Arg Thr Ser Pro Pro Pro Gly Leu Ala Gly
            245                 250                 255

Pro Ser Leu Ser Ser Ser Ser Phe Ser Pro Ser Ser Pro Pro Pro
            260                 265                 270

Pro Gly Asp Leu Pro Leu Ser Pro Ala Phe Ser Ala Ala Pro Gly
            275                 280                 285

Thr Pro Leu Ala Arg Arg Asp Pro Thr Pro Val Cys Cys Pro Ser Cys
290                 295                 300

Arg Arg Ala Thr Pro Ile Ser Val Trp Gly Pro Leu Gly Gly Leu Val
305                 310                 315                 320

Arg Thr Pro Ser Val Gln Ser Leu Gly Ser Asp Pro Asp Glu Tyr Ala
                325                 330                 335

Ser Ser Gly Ser Ser Leu Gly Gly Ser Asp Ser Pro Val Phe Glu Ala
            340                 345                 350

Gly Val Phe Ala Pro Pro Gln Pro Val Ala Ala Pro Arg Arg Leu Pro
            355                 360                 365

Ile Phe Asn Arg Ile Ser Val Ser Glu
    370                 375

<210> SEQ ID NO 34
<211> LENGTH: 406
<212> TYPE: PRT
<213> ORGANISM: Artificial sequence
<220> FEATURE:
<223> OTHER INFORMATION: Human protein derivative

<400> SEQUENCE: 34

Glu Cys Asp Ser Glu Leu Glu Ile Lys Arg Tyr Lys Asn Arg Val Ala
1               5                   10                  15

Ser Arg Lys Cys Arg Ala Lys Phe Lys Gln Leu Leu Gln His Tyr Arg
            20                  25                  30

Glu Val Ala Ala Ala Lys Ser Ser Glu Asn Asp Arg Leu Arg Leu Leu
        35                  40                  45

Leu Lys Gln Met Pro Phe Leu Gly Gln Asp Trp Arg Ser Pro Gly Gln
    50                  55                  60

Asn Trp Val Lys Thr Ala Asp Gly Trp Lys Arg Phe Leu Asp Glu Lys
65                  70                  75                  80
```

Ser Gly Ser Phe Val Ser Asp Leu Ser Ser Tyr Cys Asn Lys Glu Val
            85                  90                  95

Tyr Asn Lys Glu Asn Leu Phe Asn Ser Leu Asn Tyr Asp Val Ala Ala
            100                 105                 110

Lys Lys Arg Lys Lys Asp Met Leu Asn Ser Lys Thr Lys Thr Gln Tyr
            115                 120                 125

Phe His Gln Glu Lys Trp Ile Tyr Val His Lys Gly Ser Thr Lys Glu
        130                 135                 140

Arg His Gly Tyr Cys Thr Leu Gly Glu Ala Phe Asn Arg Leu Asp Phe
145                 150                 155                 160

Ser Thr Ala Ile Leu Asp Ser Arg Arg Phe Asn Tyr Val Val Arg Leu
                165                 170                 175

Leu Glu Leu Ile Ala Lys Ser Gln Leu Thr Ser Leu Ser Gly Ile Ala
            180                 185                 190

Gln Lys Asn Phe Met Asn Ile Leu Glu Lys Val Val Leu Lys Val Leu
            195                 200                 205

Glu Asp Gln Gln Asn Ile Arg Leu Ile Arg Glu Leu Leu Gln Thr Leu
210                 215                 220

Tyr Thr Ser Leu Cys Thr Leu Val Gln Arg Val Gly Lys Ser Val Leu
225                 230                 235                 240

Val Gly Asn Ile Asn Met Trp Val Tyr Arg Met Glu Thr Ile Leu His
                245                 250                 255

Trp Gln Gln Gln Leu Asn Asn Ile Gln Ile Thr Arg Pro Ala Phe Lys
            260                 265                 270

Gly Leu Thr Phe Thr Asp Leu Pro Leu Cys Leu Gln Leu Asn Ile Met
            275                 280                 285

Gln Arg Leu Ser Asp Gly Arg Asp Leu Val Ser Leu Gly Gln Ala Ala
        290                 295                 300

Pro Asp Leu His Val Leu Ser Glu Asp Arg Leu Leu Trp Lys Lys Leu
305                 310                 315                 320

Cys Gln Tyr His Phe Ser Glu Arg Gln Ile Arg Lys Arg Leu Ile Leu
                325                 330                 335

Ser Asp Lys Gly Gln Leu Asp Trp Lys Lys Met Tyr Phe Lys Leu Val
            340                 345                 350

Arg Cys Tyr Pro Arg Lys Glu Gln Tyr Gly Asp Thr Leu Gln Leu Cys
            355                 360                 365

Lys His Cys His Ile Leu Ser Trp Lys Gly Thr Asp His Pro Cys Thr
        370                 375                 380

Ala Asn Asn Pro Glu Ser Cys Ser Val Ser Leu Ser Pro Gln Asp Phe
385                 390                 395                 400

Ile Asn Leu Phe Lys Phe
                405

<210> SEQ ID NO 35
<211> LENGTH: 349
<212> TYPE: PRT
<213> ORGANISM: Artificial sequence
<220> FEATURE:
<223> OTHER INFORMATION: Human protein derivative

<400> SEQUENCE: 35

Glu Cys Asp Ser Glu Leu Glu Ile Lys Arg Tyr Lys Asn Arg Val Ala
1               5                   10                  15

Ser Arg Lys Cys Arg Ala Lys Phe Lys Gln Leu Leu Gln His Tyr Arg
            20                  25                  30

Glu Val Ala Ala Ala Lys Ser Ser Glu Asn Asp Arg Leu Arg Leu Leu
                35                  40                  45

Leu Lys Gln Gly Gln Thr Pro Ala Ser Ala Gln Ala Pro Ala Gln Thr
 50                  55                  60

Pro Ala Pro Ala Leu Pro Gly Pro Ala Leu Pro Gly Pro Phe Pro Gly
 65                  70                  75                  80

Gly Arg Val Val Arg Leu His Pro Val Ile Leu Ala Ser Ile Val Asp
                 85                  90                  95

Ser Tyr Glu Arg Arg Asn Glu Gly Ala Ala Arg Val Ile Gly Thr Leu
                100                 105                 110

Leu Gly Thr Val Asp Lys His Ser Val Glu Val Thr Asn Cys Phe Ser
            115                 120                 125

Val Pro His Asn Glu Ser Glu Asp Val Ala Val Asp Met Glu Phe
        130                 135                 140

Ala Lys Asn Met Tyr Glu Leu His Lys Lys Val Ser Pro Asn Glu Leu
145                 150                 155                 160

Ile Leu Gly Trp Tyr Ala Thr Gly His Asp Ile Thr Glu His Ser Val
                165                 170                 175

Leu Ile His Glu Tyr Tyr Ser Arg Glu Ala Pro Asn Pro Ile His Leu
            180                 185                 190

Thr Val Asp Thr Ser Leu Gln Asn Gly Arg Met Ser Ile Lys Ala Tyr
        195                 200                 205

Val Ser Thr Leu Met Gly Val Pro Gly Arg Thr Met Gly Val Met Phe
    210                 215                 220

Thr Pro Leu Thr Val Lys Tyr Ala Tyr Asp Thr Gly Arg Ile Gly
225                 230                 235                 240

Val Asp Leu Ile Met Lys Thr Cys Phe Ser Pro Asn Arg Val Ile Gly
                245                 250                 255

Leu Ser Ser Asp Leu Gln Gln Val Gly Gly Ala Ser Ala Arg Ile Gln
            260                 265                 270

Asp Ala Leu Ser Thr Val Leu Gln Tyr Ala Glu Asp Val Leu Ser Gly
        275                 280                 285

Lys Val Ser Ala Asp Asn Thr Val Gly Arg Phe Leu Met Ser Leu Val
    290                 295                 300

Asn Gln Val Pro Lys Ile Val Pro Asp Asp Phe Glu Thr Met Leu Asn
305                 310                 315                 320

Ser Asn Ile Asn Asp Leu Leu Met Val Thr Tyr Leu Ala Asn Leu Thr
                325                 330                 335

Gln Ser Gln Ile Ala Leu Asn Glu Lys Leu Val Asn Leu
            340                 345

<210> SEQ ID NO 36
<211> LENGTH: 257
<212> TYPE: PRT
<213> ORGANISM: Artificial sequence
<220> FEATURE:
<223> OTHER INFORMATION: Human protein derivative

<400> SEQUENCE: 36

Glu Cys Asp Ser Glu Leu Glu Ile Lys Arg Tyr Lys Asn Arg Val Ala
1               5                   10                  15

Ser Arg Lys Cys Arg Ala Lys Phe Lys Gln Leu Leu Gln His Tyr Arg
            20                  25                  30

Glu Val Ala Ala Ala Lys Ser Ser Glu Asn Asp Arg Leu Arg Leu Leu
        35                  40                  45

```
Leu Lys Gln Met Asn Phe Gln Gln Arg Leu Gln Ser Leu Trp Thr Leu
 50                  55                  60

Ala Arg Pro Phe Cys Pro Pro Leu Leu Ala Thr Ala Ser Gln Met Gln
 65                  70                  75                  80

Met Val Val Leu Pro Cys Leu Gly Phe Thr Leu Leu Leu Trp Ser Gln
                 85                  90                  95

Val Ser Gly Ala Gln Gly Gln Glu Phe His Phe Gly Pro Cys Gln Val
                100                 105                 110

Lys Gly Val Val Pro Gln Lys Leu Trp Glu Ala Phe Trp Ala Val Lys
                115                 120                 125

Asp Thr Met Gln Ala Gln Asp Asn Ile Thr Ser Ala Arg Leu Leu Gln
130                 135                 140

Gln Glu Val Leu Gln Asn Val Ser Asp Ala Glu Ser Cys Tyr Leu Val
145                 150                 155                 160

His Thr Leu Leu Glu Phe Tyr Leu Lys Thr Val Phe Lys Asn Tyr His
                165                 170                 175

Asn Arg Thr Val Glu Val Arg Thr Leu Lys Ser Phe Ser Thr Leu Ala
                180                 185                 190

Asn Asn Phe Val Leu Ile Val Ser Gln Leu Gln Pro Ser Gln Glu Asn
                195                 200                 205

Glu Met Phe Ser Ile Arg Asp Ser Ala His Arg Arg Phe Leu Leu Phe
210                 215                 220

Arg Arg Ala Phe Lys Gln Leu Asp Val Glu Ala Ala Leu Thr Lys Ala
225                 230                 235                 240

Leu Gly Glu Val Asp Ile Leu Leu Thr Trp Met Gln Lys Phe Tyr Lys
                245                 250                 255

Leu

<210> SEQ ID NO 37
<211> LENGTH: 835
<212> TYPE: PRT
<213> ORGANISM: Artificial sequence
<220> FEATURE:
<223> OTHER INFORMATION: Human protein derivative

<400> SEQUENCE: 37

Glu Cys Asp Ser Glu Leu Glu Ile Lys Arg Tyr Lys Asn Arg Val Ala
 1               5                   10                  15

Ser Arg Lys Cys Arg Ala Lys Phe Lys Gln Leu Leu Gln His Tyr Arg
                 20                  25                  30

Glu Val Ala Ala Ala Lys Ser Ser Glu Asn Asp Arg Leu Arg Leu Leu
                 35                  40                  45

Leu Lys Gln Met Gln Arg Leu Met Met Leu Leu Ala Thr Ser Gly Ala
 50                  55                  60

Cys Leu Gly Leu Leu Ala Val Ala Ala Val Ala Ala Gly Ala Asn
 65                  70                  75                  80

Pro Ala Gln Arg Asp Thr His Ser Leu Leu Pro Thr His Arg Arg Gln
                 85                  90                  95

Lys Arg Asp Trp Ile Trp Asn Gln Met His Ile Asp Glu Glu Lys Asn
                100                 105                 110

Thr Ser Leu Pro His His Val Gly Lys Ile Lys Ser Ser Val Ser Arg
                115                 120                 125

Lys Asn Ala Lys Tyr Leu Leu Lys Gly Glu Tyr Val Gly Lys Val Phe
130                 135                 140
```

-continued

Arg Val Asp Ala Glu Thr Gly Asp Val Phe Ala Ile Glu Arg Leu Asp
145                 150                 155                 160

Arg Glu Asn Ile Ser Glu Tyr His Leu Thr Ala Val Ile Val Asp Lys
            165                 170                 175

Asp Thr Gly Glu Asn Leu Glu Thr Pro Ser Ser Phe Thr Ile Lys Val
        180                 185                 190

His Asp Val Asn Asp Asn Trp Pro Val Phe Thr His Arg Leu Phe Asn
    195                 200                 205

Ala Ser Val Pro Glu Ser Ser Ala Val Gly Thr Ser Val Ile Ser Val
210                 215                 220

Thr Ala Val Asp Ala Asp Asp Pro Thr Val Gly Asp His Ala Ser Val
225                 230                 235                 240

Met Tyr Gln Ile Leu Lys Gly Lys Glu Tyr Phe Ala Ile Asp Asn Ser
            245                 250                 255

Gly Arg Ile Ile Thr Ile Thr Lys Ser Leu Asp Arg Glu Lys Gln Ala
        260                 265                 270

Arg Tyr Glu Ile Val Val Glu Ala Arg Asp Ala Gln Gly Leu Arg Gly
    275                 280                 285

Asp Ser Gly Thr Ala Thr Val Leu Val Thr Leu Gln Asp Ile Asn Asp
290                 295                 300

Asn Phe Pro Phe Phe Thr Gln Thr Lys Tyr Thr Phe Val Val Pro Glu
305                 310                 315                 320

Asp Thr Arg Val Gly Thr Ser Val Gly Ser Leu Phe Val Glu Asp Pro
            325                 330                 335

Asp Glu Pro Gln Asn Arg Met Thr Lys Tyr Ser Ile Leu Arg Gly Asp
        340                 345                 350

Tyr Gln Asp Ala Phe Thr Ile Glu Thr Asn Pro Ala His Asn Glu Gly
    355                 360                 365

Ile Ile Lys Pro Met Lys Pro Leu Asp Tyr Glu Tyr Ile Gln Gln Tyr
        370                 375                 380

Ser Phe Ile Val Glu Ala Thr Asp Pro Thr Ile Asp Leu Arg Tyr Met
385                 390                 395                 400

Ser Pro Pro Ala Gly Asn Arg Ala Gln Val Ile Ile Asn Ile Thr Asp
            405                 410                 415

Val Asp Glu Pro Pro Ile Phe Gln Gln Pro Phe Tyr His Phe Gln Leu
        420                 425                 430

Lys Glu Asn Gln Lys Lys Pro Leu Ile Gly Thr Val Leu Ala Met Asp
    435                 440                 445

Pro Asp Ala Ala Arg His Ser Ile Gly Tyr Ser Ile Arg Arg Thr Ser
450                 455                 460

Asp Lys Gly Gln Phe Phe Arg Val Thr Lys Lys Gly Asp Ile Tyr Asn
465                 470                 475                 480

Glu Lys Glu Leu Asp Arg Glu Val Tyr Pro Trp Tyr Asn Leu Thr Val
            485                 490                 495

Glu Ala Lys Glu Leu Asp Ser Thr Gly Thr Pro Thr Gly Lys Glu Ser
        500                 505                 510

Ile Val Gln Val His Ile Glu Val Leu Asp Glu Asn Asp Asn Ala Pro
    515                 520                 525

Glu Phe Ala Lys Pro Tyr Gln Pro Lys Val Cys Glu Asn Ala Val His
        530                 535                 540

Gly Gln Leu Val Leu Gln Ile Ser Ala Ile Asp Lys Asp Ile Thr Pro
545                 550                 555                 560

Arg Asn Val Lys Phe Lys Phe Thr Leu Asn Thr Glu Asn Asn Phe Thr

```
                          565                 570                 575

Leu Thr Asp Asn His Asp Asn Thr Ala Asn Ile Thr Val Lys Tyr Gly
            580                 585                 590

Gln Phe Asp Arg Glu His Thr Lys Val His Phe Leu Pro Val Val Ile
            595                 600                 605

Ser Asp Asn Gly Met Pro Ser Arg Thr Gly Thr Ser Thr Leu Thr Val
    610                 615                 620

Ala Val Cys Lys Cys Asn Glu Gln Gly Glu Phe Thr Phe Cys Glu Asp
625                 630                 635                 640

Met Ala Ala Gln Val Gly Val Ser Ile Gln Ala Val Val Ala Ile Leu
                645                 650                 655

Leu Cys Ile Leu Thr Ile Thr Val Ile Thr Leu Leu Ile Phe Leu Arg
                660                 665                 670

Arg Arg Leu Arg Lys Gln Ala Arg Ala His Gly Lys Ser Val Pro Glu
            675                 680                 685

Ile His Glu Gln Leu Val Thr Tyr Asp Glu Gly Gly Gly Glu Met
            690                 695                 700

Asp Thr Thr Ser Tyr Asp Val Ser Val Leu Asn Ser Val Arg Arg Gly
705                 710                 715                 720

Gly Ala Lys Pro Pro Arg Pro Ala Leu Asp Ala Arg Pro Ser Leu Tyr
                725                 730                 735

Ala Gln Val Gln Lys Pro Pro Arg His Ala Pro Gly Ala His Gly Gly
                740                 745                 750

Pro Gly Glu Met Ala Ala Met Ile Glu Val Lys Lys Asp Glu Ala Asp
            755                 760                 765

His Asp Gly Asp Gly Pro Pro Tyr Asp Thr Leu His Ile Tyr Gly Tyr
            770                 775                 780

Glu Gly Ser Glu Ser Ile Ala Glu Ser Leu Ser Ser Leu Gly Thr Asp
785                 790                 795                 800

Ser Ser Asp Ser Asp Val Asp Tyr Asp Phe Leu Asn Asp Trp Gly Pro
                805                 810                 815

Arg Phe Lys Met Leu Ala Glu Leu Tyr Gly Ser Asp Pro Arg Glu Glu
            820                 825                 830

Leu Leu Tyr
        835

<210> SEQ ID NO 38
<211> LENGTH: 60
<212> TYPE: PRT
<213> ORGANISM: Artificial sequence
<220> FEATURE:
<223> OTHER INFORMATION: Human protein derivative
<220> FEATURE:
<221> NAME/KEY: SITE
<222> LOCATION: (56)..(56)
<223> OTHER INFORMATION: tyrosine Y56 is phosphorylated by src kinase

<400> SEQUENCE: 38

Glu Cys Asp Ser Glu Leu Glu Ile Lys Arg Tyr Lys Asn Arg Val Ala
1               5                   10                  15

Ser Arg Lys Cys Arg Ala Lys Phe Lys Gln Leu Leu Gln His Tyr Arg
            20                  25                  30

Glu Val Ala Ala Ala Lys Ser Ser Glu Asn Asp Arg Leu Arg Leu Leu
        35                  40                  45

Leu Lys Gln Arg Pro Ser Leu Tyr Ala Gln Val Gln
    50                  55                  60
```

```
<210> SEQ ID NO 39
<211> LENGTH: 444
<212> TYPE: PRT
<213> ORGANISM: Artificial sequence
<220> FEATURE:
<223> OTHER INFORMATION: Human protein derivative

<400> SEQUENCE: 39

Glu Cys Asp Ser Glu Leu Glu Ile Lys Arg Tyr Lys Asn Arg Val Ala
1               5                   10                  15

Ser Arg Lys Cys Arg Ala Lys Phe Lys Gln Leu Leu Gln His Tyr Arg
            20                  25                  30

Glu Val Ala Ala Lys Ser Ser Glu Asn Asp Arg Leu Arg Leu Leu
        35                  40                  45

Leu Lys Gln Met Glu Glu Pro Gln Ser Asp Pro Ser Val Glu Pro Pro
50                  55                  60

Leu Ser Gln Glu Thr Phe Ser Asp Leu Trp Lys Leu Leu Pro Glu Asn
65                  70                  75                  80

Asn Val Leu Ser Pro Leu Pro Ser Gln Ala Met Asp Asp Leu Met Leu
                85                  90                  95

Ser Pro Asp Asp Ile Glu Gln Trp Phe Thr Glu Asp Pro Gly Pro Asp
            100                 105                 110

Glu Ala Pro Arg Met Pro Glu Ala Ala Pro Val Ala Pro Ala Pro
        115                 120                 125

Ala Ala Pro Thr Pro Ala Ala Pro Ala Pro Ala Pro Ser Trp Pro Leu
130                 135                 140

Ser Ser Ser Val Pro Ser Gln Lys Thr Tyr Gln Gly Ser Tyr Gly Phe
145                 150                 155                 160

Arg Leu Gly Phe Leu His Ser Gly Thr Ala Lys Ser Val Thr Cys Thr
                165                 170                 175

Tyr Ser Pro Ala Leu Asn Lys Met Phe Cys Gln Leu Ala Lys Thr Cys
            180                 185                 190

Pro Val Gln Leu Trp Val Asp Ser Thr Pro Pro Pro Gly Thr Arg Val
        195                 200                 205

Arg Ala Met Ala Ile Tyr Lys Gln Ser Gln His Met Thr Glu Val Val
210                 215                 220

Arg Arg Cys Pro His His Glu Arg Cys Ser Asp Ser Asp Gly Leu Ala
225                 230                 235                 240

Pro Pro Gln His Leu Ile Arg Val Glu Gly Asn Leu Arg Val Glu Tyr
                245                 250                 255

Leu Asp Asp Arg Asn Thr Phe Arg His Ser Val Val Val Pro Tyr Glu
            260                 265                 270

Pro Pro Glu Val Gly Ser Asp Cys Thr Thr Ile His Tyr Asn Tyr Met
        275                 280                 285

Cys Asn Ser Ser Cys Met Gly Gly Met Asn Arg Arg Pro Ile Leu Thr
290                 295                 300

Ile Ile Thr Leu Glu Asp Ser Ser Gly Asn Leu Leu Gly Arg Asn Ser
305                 310                 315                 320

Phe Glu Val Arg Val Cys Ala Cys Pro Gly Arg Asp Arg Arg Thr Glu
                325                 330                 335

Glu Glu Asn Leu Arg Lys Lys Gly Glu Pro His His Glu Leu Pro Pro
            340                 345                 350

Gly Ser Thr Lys Arg Ala Leu Pro Asn Asn Thr Ser Ser Pro Gln
        355                 360                 365
```

```
Pro Lys Lys Pro Leu Asp Gly Glu Tyr Phe Thr Leu Gln Ile Arg
    370             375                 380

Gly Arg Glu Arg Phe Glu Met Phe Arg Glu Leu Asn Glu Ala Leu Glu
385                 390                 395                 400

Leu Lys Asp Ala Gln Ala Gly Lys Glu Pro Gly Gly Ser Arg Ala His
                405                 410                 415

Ser Ser His Leu Lys Ser Lys Gly Gln Ser Thr Ser Arg His Lys
            420                 425                 430

Lys Leu Met Phe Lys Thr Glu Gly Pro Asp Ser Asp
        435                 440
```

<210> SEQ ID NO 40
<211> LENGTH: 371
<212> TYPE: PRT
<213> ORGANISM: Artificial Sequence
<220> FEATURE:
<223> OTHER INFORMATION: Human protein derivative

<400> SEQUENCE: 40

```
Met Pro Lys Pro Ile Asn Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Tyr Phe Gly Leu His
        35                  40                  45

Tyr Val Asp Asn Lys Gly Phe Pro Thr Trp Leu Lys Leu Asp Lys Lys
    50                  55                  60

Val Ser Ala Gln Glu Val Arg Lys Glu Asn Pro Leu Gln Phe Lys Phe
65                  70                  75                  80

Arg Ala Lys Phe Tyr Pro Glu Asp Val Ala Glu Glu Leu Ile Gln Asp
                85                  90                  95

Ile Thr Gln Lys Leu Phe Phe Leu Gln Val Lys Glu Gly Ile Leu Ser
            100                 105                 110

Asp Glu Ile Tyr Cys Pro Pro Glu Thr Ala Val Leu Leu Gly Ser Tyr
        115                 120                 125

Ala Val Gln Ala Lys Phe Gly Asp Tyr Asn Lys Glu Val His Lys Ser
    130                 135                 140

Gly Tyr Leu Ser Ser Glu Arg Leu Ile Pro Gln Arg Val Met Asp Gln
145                 150                 155                 160

His Lys Leu Thr Arg Asp Gln Trp Glu Asp Arg Ile Gln Val Trp His
                165                 170                 175

Ala Glu His Arg Gly Met Leu Lys Asp Asn Ala Met Leu Glu Tyr Leu
            180                 185                 190

Lys Ile Ala Gln Asp Leu Glu Met Tyr Gly Ile Asn Tyr Phe Glu Ile
        195                 200                 205

Lys Asn Lys Lys Gly Thr Asp Leu Trp Leu Gly Val Asp Ala Leu Gly
    210                 215                 220

Leu Asn Ile Tyr Glu Lys Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Gln Leu Cys Met Gly Asn His
        275                 280                 285
```

```
Glu Leu Tyr Met Arg Arg Lys Pro Asp Thr Ile Glu Val Gln Gln
    290                 295                 300
Met Lys Ala Gln Ala Arg Glu Glu Lys His Gln Lys Gln Leu Glu Arg
305                 310                 315                 320
Glu Cys Asp Ser Glu Leu Glu Ile Lys Arg Tyr Lys Asn Arg Val Ala
                325                 330                 335
Ser Arg Lys Cys Arg Ala Lys Phe Lys Gln Leu Leu Gln His Tyr Arg
            340                 345                 350
Glu Val Ala Ala Ala Lys Ser Ser Glu Asn Asp Arg Leu Arg Leu Leu
        355                 360                 365
Leu Lys Gln
    370

<210> SEQ ID NO 41
<211> LENGTH: 251
<212> TYPE: PRT
<213> ORGANISM: Artificial sequence
<220> FEATURE:
<223> OTHER INFORMATION: Human protein derivative

<400> SEQUENCE: 41

Glu Cys Asp Ser Glu Leu Glu Ile Lys Arg Tyr Lys Asn Arg Val Ala
1               5                   10                  15
Ser Arg Lys Cys Arg Ala Lys Phe Lys Gln Leu Leu Gln His Tyr Arg
            20                  25                  30
Glu Val Ala Ala Ala Lys Ser Ser Glu Asn Asp Arg Leu Arg Leu Leu
        35                  40                  45
Leu Lys Gln Met His His His His His His Lys Arg Tyr Lys
    50                  55                  60
Asn Arg Val Ala Ser Arg Lys Cys Arg Ala Lys Phe Lys Gln Leu Leu
65                  70                  75                  80
Gln His Tyr Arg Glu Val Ala Ala Ala Lys Ser Ser Glu Asn Asp Arg
                85                  90                  95
Leu Arg Leu Leu Leu Lys Gln Met Cys Lys Leu Ala Lys Phe Val Ala
            100                 105                 110
Ala Trp Thr Leu Lys Ala Ala Ala Gly Ser Asp Glu Val Ser Gly Leu
        115                 120                 125
Glu Gln Leu Glu Ser Ile Ile Asn Phe Glu Lys Leu Thr Glu Trp Thr
    130                 135                 140
Ser Ser Asn Val Met Glu Glu Arg Lys Ile Lys Val Tyr Leu Pro Arg
145                 150                 155                 160
Met Lys Met Glu Glu Lys Tyr Asn Leu Thr Ser Val Leu Met Ala Met
                165                 170                 175
Gly Ile Thr Asp Val Phe Ser Ser Ala Asn Leu Ser Gly Ile Ser
            180                 185                 190
Ser Ala Glu Ser Leu Lys Ile Ser Gln Ala Val His Ala Ala His Ala
        195                 200                 205
Glu Ile Asn Glu Ala Gly Arg Glu Val Val Gly Ser Ala Glu Ala Gly
    210                 215                 220
Val Asp Ala Ala Ser Val Ser Glu Glu Phe Arg Ala Asp His Pro Phe
225                 230                 235                 240
Leu Phe Cys Ile Lys His Ile Ala Thr Asn Ala
                245                 250

<210> SEQ ID NO 42
<211> LENGTH: 349
```

<212> TYPE: PRT
<213> ORGANISM: Artificial sequence
<220> FEATURE:
<223> OTHER INFORMATION: Human protein derivative

<400> SEQUENCE: 42

Met Arg His Met Gln Ser Ala Thr Arg Ala Thr Leu Val Cys Gly Ser
1               5                   10                  15

Gly Val Lys Gln Ile Ile Ala Lys Gly His Pro Asn Thr Arg Val Phe
            20                  25                  30

Gly Ala Arg Lys Ala Arg Ile Pro Glu Arg Glu Val Leu Ala Ala Lys
        35                  40                  45

Pro Lys Ile Thr Arg Ile Thr His Leu Asn Leu Gln Pro Gln Glu Arg
50                  55                  60

Gln Ala Phe Tyr Arg Leu Leu Glu Asn Glu Leu Ile Gln Glu Phe Leu
65                  70                  75                  80

Ser Met Asp Ser Cys Leu Lys Ile Ser Asp Lys Tyr Leu Ile Ala Met
                85                  90                  95

Val Leu Ala Tyr Phe Lys Arg Ala Gly Leu Tyr Thr Gly Glu Tyr Thr
            100                 105                 110

Thr Met Asn Phe Phe Val Ala Leu Tyr Leu Ala Asn Asp Met Glu Glu
        115                 120                 125

Asp Glu Glu Asp Tyr Lys Tyr Glu Ile Phe Pro Trp Ala Leu Gly Asp
130                 135                 140

Ser Trp Arg Glu Phe Phe Pro Gln Phe Leu Arg Leu Arg Asp Asn Phe
145                 150                 155                 160

Trp Ala Lys Met Asn Tyr Arg Ala Val Val Ser Arg Arg Cys Cys Asp
                165                 170                 175

Glu Val Met Ala Lys Asp Pro Thr His Trp Ala Trp Leu Arg Asp Arg
            180                 185                 190

Pro Ile His His Ser Gly Ala Leu Arg Gly Tyr Leu Arg Asn Glu Asp
        195                 200                 205

Asp Phe Phe Pro Arg Gly Pro Gly Leu Thr Pro Ala Ser Cys Ala Leu
210                 215                 220

Cys His Lys Ala Ser Val Cys Asp Ser Gly Gly Val Ala His Asp Asn
225                 230                 235                 240

Ser Ser Pro Glu Gln Glu Ile Phe His Tyr Thr Asn Arg Glu Trp Ser
                245                 250                 255

Gln Glu Leu Leu Ile Leu Pro Pro Glu Leu Leu Asp Pro Glu Ser
            260                 265                 270

Thr Tyr Asp Ile His Ile Phe Gln Glu Pro Leu Val Gly Leu Glu Pro
        275                 280                 285

Asp Gly Ala Ala Leu Glu Trp His His Leu Glu Cys Asp Ser Glu Leu
290                 295                 300

Glu Ile Lys Arg Tyr Lys Asn Arg Val Ala Ser Arg Lys Cys Arg Ala
305                 310                 315                 320

Lys Phe Lys Gln Leu Leu Gln His Tyr Arg Glu Val Ala Ala Ala Lys
                325                 330                 335

Ser Ser Glu Asn Asp Arg Leu Arg Leu Leu Lys Gln
            340                 345

<210> SEQ ID NO 43
<211> LENGTH: 182
<212> TYPE: PRT
<213> ORGANISM: Artificial sequence
<220> FEATURE:

<223> OTHER INFORMATION: Human protein derivative

<400> SEQUENCE: 43

```
Gln Glu Val Gln Ala Phe Leu Ser Leu Leu Glu Asp Ser Phe Val Gln
1               5                   10                  15

Glu Phe Leu Ser Lys Asp Pro Cys Phe Gln Ile Ser Lys Tyr Leu
            20                  25                  30

Leu Ala Met Val Leu Val Tyr Phe Gln Arg Ala His Leu Lys Leu Ser
        35                  40                  45

Glu Tyr Thr His Ser Ser Leu Phe Leu Ala Leu Tyr Leu Ala Asn Asp
    50                  55                  60

Met Glu Glu Asp Leu Glu Gly Pro Lys Cys Glu Ile Phe Pro Trp Ala
65                  70                  75                  80

Leu Gly Lys Asp Trp Cys Leu Arg Val Gly Lys Phe Leu His Gln Arg
                85                  90                  95

Asp Lys Leu Trp Ala Arg Met Gly Phe Arg Ala Val Val Ser Arg Gln
            100                 105                 110

Cys Cys Glu Glu Val Met Ala Lys Glu Pro Phe His Trp Ala Trp Thr
        115                 120                 125

Arg Asp Arg Glu Cys Asp Ser Glu Leu Glu Ile Lys Arg Tyr Lys Asn
    130                 135                 140

Arg Val Ala Ser Arg Lys Cys Arg Ala Lys Phe Lys Gln Leu Leu Gln
145                 150                 155                 160

His Tyr Arg Glu Val Ala Ala Lys Ser Ser Glu Asn Asp Arg Leu
                165                 170                 175

Arg Leu Leu Leu Lys Gln
            180
```

<210> SEQ ID NO 44
<211> LENGTH: 462
<212> TYPE: PRT
<213> ORGANISM: Artificial sequence
<220> FEATURE:
<223> OTHER INFORMATION: Human protein derivative

<400> SEQUENCE: 44

```
Met Pro Arg Glu Arg Lys Glu Arg Asp Ser Lys Asp His Ser Asn Met
1               5                   10                  15

Lys Glu Glu Gly Gly Ser Asp Leu Ser Val Arg Ser Lys Arg Lys
            20                  25                  30

Ala Asn Val Ala Val Phe Leu Gln Asp Pro Asp Glu Glu Ile Ala Lys
        35                  40                  45

Ile Asp Lys Thr Val Lys Ser Gln Asp Ser Ser Gln Pro Trp Asp Asp
    50                  55                  60

Asp Ser Ala Cys Val Asp Pro Cys Ser Phe Ile Pro Thr Pro Asn Lys
65                  70                  75                  80

Glu Glu Asp Asn Glu Leu Glu Tyr Pro Lys Thr Ala Phe Gln Pro Arg
                85                  90                  95

Lys Ile Arg Pro Pro Arg Ala Ser Pro Leu Pro Val Leu Asn Trp Gly
            100                 105                 110

Asn Arg Glu Glu Val Trp Arg Ile Met Leu Asn Lys Glu Lys Thr Tyr
        115                 120                 125

Leu Arg Asp Glu His Phe Leu Gln Arg His Pro Leu Leu Gln Ala Arg
    130                 135                 140

Met Arg Ala Val Leu Leu Asp Trp Leu Met Glu Val Cys Glu Val Tyr
145                 150                 155                 160
```

```
Lys Leu His Arg Glu Thr Phe Tyr Leu Ala Gln Asp Phe Phe Asp Arg
            165                 170                 175

Tyr Met Ala Ser Gln Gln Asn Ile Ile Lys Thr Leu Leu Gln Leu Ile
            180                 185                 190

Gly Ile Ser Ala Leu Phe Ile Ala Ser Lys Leu Glu Glu Ile Tyr Pro
            195                 200                 205

Pro Lys Leu His Gln Phe Ala Tyr Val Thr Asp Gly Ala Cys Ser Gly
            210                 215                 220

Asp Glu Ile Leu Thr Met Glu Leu Met Met Met Lys Ala Leu Lys Trp
225                 230                 235                 240

Arg Leu Ser Pro Leu Thr Ile Val Ser Trp Leu Asn Val Tyr Val Gln
            245                 250                 255

Val Ala Tyr Val Asn Asp Thr Gly Glu Val Leu Met Pro Gln Tyr Pro
            260                 265                 270

Gln Gln Val Phe Val Gln Ile Ala Glu Leu Leu Asp Leu Cys Val Leu
            275                 280                 285

Asp Val Gly Cys Leu Glu Phe Pro Tyr Gly Val Leu Ala Ala Ser Ala
290                 295                 300

Leu Tyr His Phe Ser Ser Leu Glu Leu Met Gln Lys Val Ser Gly Tyr
305                 310                 315                 320

Gln Trp Cys Asp Ile Glu Lys Cys Val Lys Trp Met Val Pro Phe Ala
            325                 330                 335

Met Val Ile Arg Glu Met Gly Ser Ser Lys Leu Lys His Phe Arg Gly
            340                 345                 350

Val Pro Met Glu Asp Ser His Asn Ile Gln Thr His Thr Asn Ser Leu
            355                 360                 365

Asp Leu Leu Asp Lys Ala Gln Ala Lys Lys Ala Ile Leu Ser Glu Gln
370                 375                 380

Asn Arg Ile Ser Pro Pro Ser Gly Val Leu Thr Pro Pro His Ser
385                 390                 395                 400

Ser Lys Lys Gln Ser Ser Glu Gln Glu Thr Glu Glu Cys Asp Ser Glu
            405                 410                 415

Leu Glu Ile Lys Arg Tyr Lys Asn Arg Val Ala Ser Arg Lys Cys Arg
            420                 425                 430

Ala Lys Phe Lys Gln Leu Leu Gln His Tyr Arg Glu Val Ala Ala Ala
            435                 440                 445

Lys Ser Ser Glu Asn Asp Arg Leu Arg Leu Leu Leu Lys Gln
            450                 455                 460

<210> SEQ ID NO 45
<211> LENGTH: 71
<212> TYPE: PRT
<213> ORGANISM: Artificial sequence
<220> FEATURE:
<223> OTHER INFORMATION: Human protein derivative

<400> SEQUENCE: 45

Glu Leu Met Ile Met Lys Ala Leu Lys Trp Arg Leu Ser Pro Leu Thr
1               5                   10                  15

Ile Val Ser Trp Glu Cys Asp Ser Glu Leu Glu Ile Lys Arg Tyr Lys
            20                  25                  30

Asn Arg Val Ala Ser Arg Lys Cys Arg Ala Lys Phe Lys Gln Leu Leu
            35                  40                  45

Gln His Tyr Arg Glu Val Ala Ala Ala Lys Ser Ser Glu Asn Asp Arg
        50                  55                  60
```

Leu Arg Leu Leu Leu Lys Gln
65                  70

<210> SEQ ID NO 46
<211> LENGTH: 377
<212> TYPE: PRT
<213> ORGANISM: Artificial sequence
<220> FEATURE:
<223> OTHER INFORMATION: Human protein derivative

<400> SEQUENCE: 46

Met Asp Leu Thr Ala Ile Tyr Glu Ser Leu Leu Ser Leu Ser Pro Asp
1               5                   10                  15

Val Pro Val Pro Ser Asp His Gly Gly Thr Glu Ser Ser Pro Gly Trp
                20                  25                  30

Gly Ser Ser Gly Pro Trp Ser Leu Ser Pro Ser Asp Ser Ser Pro Ser
            35                  40                  45

Gly Val Thr Ser Arg Leu Pro Gly Arg Ser Thr Ser Leu Val Glu Gly
        50                  55                  60

Arg Ser Cys Gly Trp Val Pro Pro Pro Gly Phe Ala Pro Leu Ala
65                  70                  75                  80

Pro Arg Leu Gly Pro Glu Leu Ser Pro Ser Pro Thr Ser Pro Thr Ala
                85                  90                  95

Thr Ser Thr Thr Pro Ser Arg Tyr Lys Thr Glu Leu Cys Arg Thr Phe
            100                 105                 110

Ser Glu Ser Gly Arg Cys Arg Tyr Gly Ala Lys Cys Gln Phe Ala His
        115                 120                 125

Gly Leu Gly Glu Leu Arg Gln Ala Asn Arg His Pro Lys Tyr Lys Thr
130                 135                 140

Glu Leu Cys His Lys Phe Tyr Leu Gln Gly Arg Cys Pro Tyr Gly Ser
145                 150                 155                 160

Arg Cys His Phe Ile His Asn Pro Ser Glu Asp Leu Ala Ala Pro Gly
                165                 170                 175

His Pro Pro Val Leu Arg Gln Ser Ile Ser Phe Ser Gly Leu Pro Ser
            180                 185                 190

Gly Arg Arg Thr Ser Pro Pro Pro Gly Leu Ala Gly Pro Ser Leu
        195                 200                 205

Ser Ser Ser Ser Phe Ser Pro Ser Ser Pro Pro Pro Gly Asp
    210                 215                 220

Leu Pro Leu Ser Pro Ser Ala Phe Ser Ala Ala Pro Gly Thr Pro Leu
225                 230                 235                 240

Ala Arg Arg Asp Pro Thr Pro Val Cys Cys Pro Ser Cys Arg Arg Ala
                245                 250                 255

Thr Pro Ile Ser Val Trp Gly Pro Leu Gly Gly Leu Val Arg Thr Pro
            260                 265                 270

Ser Val Gln Ser Leu Gly Ser Asp Pro Asp Glu Tyr Ala Ser Ser Gly
        275                 280                 285

Ser Ser Leu Gly Gly Ser Asp Ser Pro Val Phe Glu Ala Gly Val Phe
    290                 295                 300

Ala Pro Pro Gln Pro Val Ala Pro Arg Arg Leu Pro Ile Phe Asn
305                 310                 315                 320

Arg Ile Ser Val Ser Glu Glu Cys Asp Ser Glu Leu Glu Ile Lys Arg
                325                 330                 335

Tyr Lys Asn Arg Val Ala Ser Arg Lys Cys Arg Ala Lys Phe Lys Gln
            340                 345                 350

Leu Leu Gln His Tyr Arg Glu Val Ala Ala Lys Ser Ser Glu Asn
            355                 360                 365

Asp Arg Leu Arg Leu Leu Lys Gln
    370                 375

<210> SEQ ID NO 47
<211> LENGTH: 406
<212> TYPE: PRT
<213> ORGANISM: Artificial sequence
<220> FEATURE:
<223> OTHER INFORMATION: Human protein derivative

<400> SEQUENCE: 47

Met Pro Phe Leu Gly Gln Asp Trp Arg Ser Pro Gly Gln Asn Trp Val
1               5                   10                  15

Lys Thr Ala Asp Gly Trp Lys Arg Phe Leu Asp Glu Lys Ser Gly Ser
            20                  25                  30

Phe Val Ser Asp Leu Ser Ser Tyr Cys Asn Lys Glu Val Tyr Asn Lys
        35                  40                  45

Glu Asn Leu Phe Asn Ser Leu Asn Tyr Asp Val Ala Ala Lys Lys Arg
    50                  55                  60

Lys Lys Asp Met Leu Asn Ser Lys Thr Lys Thr Gln Tyr Phe His Gln
65                  70                  75                  80

Glu Lys Trp Ile Tyr Val His Lys Gly Ser Thr Lys Glu Arg His Gly
                85                  90                  95

Tyr Cys Thr Leu Gly Glu Ala Phe Asn Arg Leu Asp Phe Ser Thr Ala
            100                 105                 110

Ile Leu Asp Ser Arg Arg Phe Asn Tyr Val Val Arg Leu Leu Glu Leu
        115                 120                 125

Ile Ala Lys Ser Gln Leu Thr Ser Leu Ser Gly Ile Ala Gln Lys Asn
    130                 135                 140

Phe Met Asn Ile Leu Glu Lys Val Val Leu Lys Val Leu Glu Asp Gln
145                 150                 155                 160

Gln Asn Ile Arg Leu Ile Arg Glu Leu Leu Gln Thr Leu Tyr Thr Ser
                165                 170                 175

Leu Cys Thr Leu Val Gln Arg Val Gly Lys Ser Val Leu Val Gly Asn
            180                 185                 190

Ile Asn Met Trp Val Tyr Arg Met Glu Thr Ile Leu His Trp Gln Gln
        195                 200                 205

Gln Leu Asn Asn Ile Gln Ile Thr Arg Pro Ala Phe Lys Gly Leu Thr
    210                 215                 220

Phe Thr Asp Leu Pro Leu Cys Leu Gln Leu Asn Ile Met Gln Arg Leu
225                 230                 235                 240

Ser Asp Gly Arg Asp Leu Val Ser Leu Gly Gln Ala Ala Pro Asp Leu
                245                 250                 255

His Val Leu Ser Glu Asp Arg Leu Leu Trp Lys Lys Leu Cys Gln Tyr
            260                 265                 270

His Phe Ser Glu Arg Gln Ile Arg Lys Arg Leu Ile Leu Ser Asp Lys
        275                 280                 285

Gly Gln Leu Asp Trp Lys Lys Met Tyr Phe Lys Leu Val Arg Cys Tyr
    290                 295                 300

Pro Arg Lys Glu Gln Tyr Gly Asp Thr Leu Gln Leu Cys Lys His Cys
305                 310                 315                 320

His Ile Leu Ser Trp Lys Gly Thr Asp His Pro Cys Thr Ala Asn Asn
                325                 330                 335

```
Pro Glu Ser Cys Ser Val Ser Leu Ser Pro Gln Asp Phe Ile Asn Leu
            340                 345                 350

Phe Lys Phe Glu Cys Asp Ser Glu Leu Glu Ile Lys Arg Tyr Lys Asn
            355                 360                 365

Arg Val Ala Ser Arg Lys Cys Arg Ala Lys Phe Lys Gln Leu Leu Gln
            370                 375                 380

His Tyr Arg Glu Val Ala Ala Ala Lys Ser Ser Glu Asn Asp Arg Leu
385                 390                 395                 400

Arg Leu Leu Leu Lys Gln
                405

<210> SEQ ID NO 48
<211> LENGTH: 349
<212> TYPE: PRT
<213> ORGANISM: Artificial sequence
<220> FEATURE:
<223> OTHER INFORMATION: Human protein derivative

<400> SEQUENCE: 48

Gly Gln Thr Pro Ala Ser Ala Gln Ala Pro Ala Gln Thr Pro Ala Pro
1               5                   10                  15

Ala Leu Pro Gly Pro Ala Leu Pro Gly Pro Phe Pro Gly Gly Arg Val
            20                  25                  30

Val Arg Leu His Pro Val Ile Leu Ala Ser Ile Val Asp Ser Tyr Glu
            35                  40                  45

Arg Arg Asn Glu Gly Ala Ala Arg Val Ile Gly Thr Leu Leu Gly Thr
        50                  55                  60

Val Asp Lys His Ser Val Glu Val Thr Asn Cys Phe Ser Val Pro His
65                  70                  75                  80

Asn Glu Ser Glu Asp Glu Val Ala Val Asp Met Glu Phe Ala Lys Asn
                85                  90                  95

Met Tyr Glu Leu His Lys Lys Val Ser Pro Asn Glu Leu Ile Leu Gly
            100                 105                 110

Trp Tyr Ala Thr Gly His Asp Ile Thr Glu His Ser Val Leu Ile His
            115                 120                 125

Glu Tyr Tyr Ser Arg Glu Ala Pro Asn Pro Ile His Leu Thr Val Asp
        130                 135                 140

Thr Ser Leu Gln Asn Gly Arg Met Ser Ile Lys Ala Tyr Val Ser Thr
145                 150                 155                 160

Leu Met Gly Val Pro Gly Arg Thr Met Gly Val Met Phe Thr Pro Leu
                165                 170                 175

Thr Val Lys Tyr Ala Tyr Tyr Asp Thr Glu Arg Ile Gly Val Asp Leu
            180                 185                 190

Ile Met Lys Thr Cys Phe Ser Pro Asn Arg Val Ile Gly Leu Ser Ser
            195                 200                 205

Asp Leu Gln Gln Val Gly Gly Ala Ser Ala Arg Ile Gln Asp Ala Leu
        210                 215                 220

Ser Thr Val Leu Gln Tyr Ala Glu Asp Val Leu Ser Gly Lys Val Ser
225                 230                 235                 240

Ala Asp Asn Thr Val Gly Arg Phe Leu Met Ser Leu Val Asn Gln Val
                245                 250                 255

Pro Lys Ile Val Pro Asp Asp Phe Glu Thr Met Leu Asn Ser Asn Ile
            260                 265                 270

Asn Asp Leu Leu Met Val Thr Tyr Leu Ala Asn Leu Thr Gln Ser Gln
            275                 280                 285
```

```
Ile Ala Leu Asn Glu Lys Leu Val Asn Leu Glu Cys Asp Ser Glu Leu
            290                 295                 300

Glu Ile Lys Arg Tyr Lys Asn Arg Val Ala Ser Arg Lys Cys Arg Ala
305                 310                 315                 320

Lys Phe Lys Gln Leu Leu Gln His Tyr Arg Glu Val Ala Ala Ala Lys
                325                 330                 335

Ser Ser Glu Asn Asp Arg Leu Arg Leu Leu Lys Gln
            340                 345

<210> SEQ ID NO 49
<211> LENGTH: 257
<212> TYPE: PRT
<213> ORGANISM: Artificial sequence
<220> FEATURE:
<223> OTHER INFORMATION: Human protein derivative

<400> SEQUENCE: 49

Met Asn Phe Gln Gln Arg Leu Gln Ser Leu Trp Thr Leu Ala Arg Pro
1               5                   10                  15

Phe Cys Pro Pro Leu Leu Ala Thr Ala Ser Gln Met Gln Met Val Val
                20                  25                  30

Leu Pro Cys Leu Gly Phe Thr Leu Leu Leu Trp Ser Gln Val Ser Gly
            35                  40                  45

Ala Gln Gly Gln Glu Phe His Phe Gly Pro Cys Gln Val Lys Gly Val
        50                  55                  60

Val Pro Gln Lys Leu Trp Glu Ala Phe Trp Ala Val Lys Asp Thr Met
65                  70                  75                  80

Gln Ala Gln Asp Asn Ile Thr Ser Ala Arg Leu Leu Gln Gln Glu Val
                85                  90                  95

Leu Gln Asn Val Ser Asp Ala Glu Ser Cys Tyr Leu Val His Thr Leu
            100                 105                 110

Leu Glu Phe Tyr Leu Lys Thr Val Phe Lys Asn Tyr His Asn Arg Thr
        115                 120                 125

Val Glu Val Arg Thr Leu Lys Ser Phe Ser Thr Leu Ala Asn Asn Phe
    130                 135                 140

Val Leu Ile Val Ser Gln Leu Gln Pro Ser Gln Glu Asn Glu Met Phe
145                 150                 155                 160

Ser Ile Arg Asp Ser Ala His Arg Arg Phe Leu Leu Phe Arg Arg Ala
                165                 170                 175

Phe Lys Gln Leu Asp Val Glu Ala Ala Leu Thr Lys Ala Leu Gly Glu
            180                 185                 190

Val Asp Ile Leu Leu Thr Trp Met Gln Lys Phe Tyr Lys Leu Glu Cys
        195                 200                 205

Asp Ser Glu Leu Glu Ile Lys Arg Tyr Lys Asn Arg Val Ala Ser Arg
    210                 215                 220

Lys Cys Arg Ala Lys Phe Lys Gln Leu Leu Gln His Tyr Arg Glu Val
225                 230                 235                 240

Ala Ala Ala Lys Ser Ser Glu Asn Asp Arg Leu Arg Leu Leu Leu Lys
                245                 250                 255

Gln

<210> SEQ ID NO 50
<211> LENGTH: 835
<212> TYPE: PRT
<213> ORGANISM: Artificial sequence
<220> FEATURE:
```

-continued

<223> OTHER INFORMATION: Human protein derivative

<400> SEQUENCE: 50

```
Met Gln Arg Leu Met Met Leu Leu Ala Thr Ser Gly Ala Cys Leu Gly
1               5                   10                  15

Leu Leu Ala Val Ala Ala Val Ala Ala Gly Ala Asn Pro Ala Gln
            20                  25                  30

Arg Asp Thr His Ser Leu Leu Pro Thr His Arg Arg Gln Lys Arg Asp
            35                  40                  45

Trp Ile Trp Asn Gln Met His Ile Asp Glu Glu Lys Asn Thr Ser Leu
        50                  55                  60

Pro His His Val Gly Lys Ile Lys Ser Ser Val Ser Arg Lys Asn Ala
65                  70                  75                  80

Lys Tyr Leu Leu Lys Gly Glu Tyr Val Gly Lys Val Phe Arg Val Asp
                85                  90                  95

Ala Glu Thr Gly Asp Val Phe Ala Ile Glu Arg Leu Asp Arg Glu Asn
            100                 105                 110

Ile Ser Glu Tyr His Leu Thr Ala Val Ile Val Asp Lys Asp Thr Gly
        115                 120                 125

Glu Asn Leu Glu Thr Pro Ser Ser Phe Thr Ile Lys Val His Asp Val
130                 135                 140

Asn Asp Asn Trp Pro Val Phe Thr His Arg Leu Phe Asn Ala Ser Val
145                 150                 155                 160

Pro Glu Ser Ser Ala Val Gly Thr Ser Val Ile Ser Val Thr Ala Val
                165                 170                 175

Asp Ala Asp Asp Pro Thr Val Gly Asp His Ala Ser Val Met Tyr Gln
            180                 185                 190

Ile Leu Lys Gly Lys Glu Tyr Phe Ala Ile Asp Asn Ser Gly Arg Ile
        195                 200                 205

Ile Thr Ile Thr Lys Ser Leu Asp Arg Glu Lys Gln Ala Arg Tyr Glu
210                 215                 220

Ile Val Val Glu Ala Arg Asp Ala Gln Gly Leu Arg Gly Asp Ser Gly
225                 230                 235                 240

Thr Ala Thr Val Leu Val Thr Leu Gln Asp Ile Asn Asp Asn Phe Pro
                245                 250                 255

Phe Phe Thr Gln Thr Lys Tyr Thr Phe Val Val Pro Glu Asp Thr Arg
            260                 265                 270

Val Gly Thr Ser Val Gly Ser Leu Phe Val Glu Asp Pro Asp Glu Pro
        275                 280                 285

Gln Asn Arg Met Thr Lys Tyr Ser Ile Leu Arg Gly Asp Tyr Gln Asp
290                 295                 300

Ala Phe Thr Ile Glu Thr Asn Pro Ala His Asn Glu Gly Ile Ile Lys
305                 310                 315                 320

Pro Met Lys Pro Leu Asp Tyr Glu Tyr Ile Gln Gln Tyr Ser Phe Ile
                325                 330                 335

Val Glu Ala Thr Asp Pro Thr Ile Asp Leu Arg Tyr Met Ser Pro Pro
            340                 345                 350

Ala Gly Asn Arg Ala Gln Val Ile Ile Asn Ile Thr Asp Val Asp Glu
        355                 360                 365

Pro Pro Ile Phe Gln Gln Pro Phe Tyr His Phe Gln Leu Lys Glu Asn
370                 375                 380

Gln Lys Lys Pro Leu Ile Gly Thr Val Leu Ala Met Asp Pro Asp Ala
385                 390                 395                 400
```

-continued

```
Ala Arg His Ser Ile Gly Tyr Ser Ile Arg Arg Thr Ser Asp Lys Gly
            405                 410                 415

Gln Phe Phe Arg Val Thr Lys Lys Gly Asp Ile Tyr Asn Glu Lys Glu
        420                 425                 430

Leu Asp Arg Glu Val Tyr Pro Trp Tyr Asn Leu Thr Val Glu Ala Lys
        435                 440                 445

Glu Leu Asp Ser Thr Gly Thr Pro Thr Gly Lys Glu Ser Ile Val Gln
    450                 455                 460

Val His Ile Glu Val Leu Asp Glu Asn Asp Asn Ala Pro Glu Phe Ala
465                 470                 475                 480

Lys Pro Tyr Gln Pro Lys Val Cys Glu Asn Ala Val His Gly Gln Leu
            485                 490                 495

Val Leu Gln Ile Ser Ala Ile Asp Lys Asp Ile Thr Pro Arg Asn Val
        500                 505                 510

Lys Phe Lys Phe Thr Leu Asn Thr Glu Asn Asn Phe Thr Leu Thr Asp
        515                 520                 525

Asn His Asp Asn Thr Ala Asn Ile Thr Val Lys Tyr Gly Gln Phe Asp
    530                 535                 540

Arg Glu His Thr Lys Val His Phe Leu Pro Val Val Ile Ser Asp Asn
545                 550                 555                 560

Gly Met Pro Ser Arg Thr Gly Thr Ser Thr Leu Thr Val Ala Val Cys
            565                 570                 575

Lys Cys Asn Glu Gln Gly Glu Phe Thr Phe Cys Glu Asp Met Ala Ala
        580                 585                 590

Gln Val Gly Val Ser Ile Gln Ala Val Val Ala Ile Leu Leu Cys Ile
    595                 600                 605

Leu Thr Ile Thr Val Ile Thr Leu Leu Ile Phe Leu Arg Arg Arg Leu
    610                 615                 620

Arg Lys Gln Ala Arg Ala His Gly Lys Ser Val Pro Glu Ile His Glu
625                 630                 635                 640

Gln Leu Val Thr Tyr Asp Glu Glu Gly Gly Glu Met Asp Thr Thr
            645                 650                 655

Ser Tyr Asp Val Ser Val Leu Asn Ser Val Arg Arg Gly Gly Ala Lys
        660                 665                 670

Pro Pro Arg Pro Ala Leu Asp Ala Arg Pro Ser Leu Tyr Ala Gln Val
    675                 680                 685

Gln Lys Pro Pro Arg His Ala Pro Gly Ala His Gly Gly Pro Gly Glu
    690                 695                 700

Met Ala Ala Met Ile Glu Val Lys Lys Asp Glu Ala Asp His Asp Gly
705                 710                 715                 720

Asp Gly Pro Pro Tyr Asp Thr Leu His Ile Tyr Gly Tyr Glu Gly Ser
            725                 730                 735

Glu Ser Ile Ala Glu Ser Leu Ser Ser Leu Gly Thr Asp Ser Ser Asp
        740                 745                 750

Ser Asp Val Asp Tyr Asp Phe Leu Asn Asp Trp Gly Pro Arg Phe Lys
    755                 760                 765

Met Leu Ala Glu Leu Tyr Gly Ser Asp Pro Arg Glu Glu Leu Leu Tyr
770                 775                 780

Glu Cys Asp Ser Glu Leu Glu Ile Lys Arg Tyr Lys Asn Arg Val Ala
785                 790                 795                 800

Ser Arg Lys Cys Arg Ala Lys Phe Lys Gln Leu Leu Gln His Tyr Arg
            805                 810                 815

Glu Val Ala Ala Lys Ser Ser Glu Asn Asp Arg Leu Arg Leu Leu
```

Leu Lys Gln
        835

<210> SEQ ID NO 51
<211> LENGTH: 60
<212> TYPE: PRT
<213> ORGANISM: Artificial sequence
<220> FEATURE:
<223> OTHER INFORMATION: Human protein derivative
<220> FEATURE:
<221> NAME/KEY: SITE
<222> LOCATION: (5)..(5)
<223> OTHER INFORMATION: la tyrosine Y5 est phosphoryle par la src
      kinase

<400> SEQUENCE: 51

Arg Pro Ser Leu Tyr Ala Gln Val Gln Glu Cys Asp Ser Glu Leu Glu
1               5                   10                  15

Ile Lys Arg Tyr Lys Asn Arg Val Ala Ser Arg Lys Cys Arg Ala Lys
            20                  25                  30

Phe Lys Gln Leu Leu Gln His Tyr Arg Glu Val Ala Ala Ala Lys Ser
        35                  40                  45

Ser Glu Asn Asp Arg Leu Arg Leu Leu Leu Lys Gln
    50                  55                  60

<210> SEQ ID NO 52
<211> LENGTH: 444
<212> TYPE: PRT
<213> ORGANISM: Artificial sequence
<220> FEATURE:
<223> OTHER INFORMATION: Human protein derivative

<400> SEQUENCE: 52

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met Ala
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp

```
                195                 200                 205
Arg Asn Thr Phe Arg His Ser Val Val Pro Tyr Glu Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Thr Glu Glu Glu Asn
275                 280                 285

Leu Arg Lys Gly Glu Pro His His Glu Leu Pro Pro Gly Ser Thr
290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
370                 375                 380

Phe Lys Thr Glu Gly Pro Asp Ser Asp Glu Cys Asp Ser Leu Glu
385                 390                 395                 400

Ile Lys Arg Tyr Lys Asn Arg Val Ala Ser Arg Lys Cys Arg Ala Lys
                405                 410                 415

Phe Lys Gln Leu Leu Gln His Tyr Arg Glu Val Ala Ala Ala Lys Ser
                420                 425                 430

Ser Glu Asn Asp Arg Leu Arg Leu Leu Leu Lys Gln
            435                 440

<210> SEQ ID NO 53
<211> LENGTH: 371
<212> TYPE: PRT
<213> ORGANISM: Artificial Sequence
<220> FEATURE:
<223> OTHER INFORMATION: Human protein derivative

<400> SEQUENCE: 53

Glu Cys Asp Ser Glu Leu Glu Ile Lys Arg Tyr Lys Asn Arg Val Ala
1               5                   10                  15

Ser Arg Lys Cys Arg Ala Lys Phe Lys Gln Leu Leu Gln His Tyr Arg
                20                  25                  30

Glu Val Ala Ala Ala Lys Ser Ser Glu Asn Asp Arg Leu Arg Leu Leu
            35                  40                  45

Leu Lys Gln Met Pro Lys Pro Ile Asn Val Arg Val Thr Thr Met Asp
        50                  55                  60

Ala Glu Leu Glu Phe Ala Ile Gln Pro Asn Thr Thr Gly Lys Gln Leu
65                  70                  75                  80

Phe Asp Gln Val Val Lys Thr Ile Gly Leu Arg Glu Val Trp Tyr Phe
                85                  90                  95

Gly Leu His Tyr Val Asp Asn Lys Gly Phe Pro Thr Trp Leu Lys Leu
                100                 105                 110

Asp Lys Lys Val Ser Ala Gln Glu Val Arg Lys Glu Asn Pro Leu Gln
```

```
            115                 120                 125
Phe Lys Phe Arg Ala Lys Phe Tyr Pro Glu Asp Val Ala Glu Glu Leu
    130                 135                 140

Ile Gln Asp Ile Thr Gln Lys Leu Phe Phe Leu Gln Val Lys Glu Gly
145                 150                 155                 160

Ile Leu Ser Asp Glu Ile Tyr Cys Pro Pro Glu Thr Ala Val Leu Leu
                165                 170                 175

Gly Ser Tyr Ala Val Gln Ala Lys Phe Gly Asp Tyr Asn Lys Glu Val
            180                 185                 190

His Lys Ser Gly Tyr Leu Ser Ser Glu Arg Leu Ile Pro Gln Arg Val
        195                 200                 205

Met Asp Gln His Lys Leu Thr Arg Asp Gln Trp Glu Asp Arg Ile Gln
    210                 215                 220

Val Trp His Ala Glu His Arg Gly Met Leu Lys Asp Asn Ala Met Leu
225                 230                 235                 240

Glu Tyr Leu Lys Ile Ala Gln Asp Leu Glu Met Tyr Gly Ile Asn Tyr
                245                 250                 255

Phe Glu Ile Lys Asn Lys Lys Gly Thr Asp Leu Trp Leu Gly Val Asp
            260                 265                 270

Ala Leu Gly Leu Asn Ile Tyr Glu Lys Asp Asp Lys Leu Thr Pro Lys
        275                 280                 285

Ile Gly Phe Pro Trp Ser Glu Ile Arg Asn Ile Ser Phe Asn Asp Lys
    290                 295                 300

Lys Phe Val Ile Lys Pro Ile Asp Lys Lys Ala Pro Asp Phe Val Phe
305                 310                 315                 320

Tyr Ala Pro Arg Leu Arg Ile Asn Lys Arg Ile Leu Gln Leu Cys Met
                325                 330                 335

Gly Asn His Glu Leu Tyr Met Arg Arg Arg Lys Pro Asp Thr Ile Glu
            340                 345                 350

Val Gln Gln Met Lys Ala Gln Ala Arg Glu Glu Lys His Gln Lys Gln
        355                 360                 365

Leu Glu Arg
    370

<210> SEQ ID NO 54
<211> LENGTH: 251
<212> TYPE: PRT
<213> ORGANISM: Artificial sequence
<220> FEATURE:
<223> OTHER INFORMATION: Human protein derivative

<400> SEQUENCE: 54

Met His His His His His His His Lys Arg Tyr Lys Asn Arg Val
1               5                   10                  15

Ala Ser Arg Lys Cys Arg Ala Lys Phe Lys Gln Leu Leu Gln His Tyr
                20                  25                  30

Arg Glu Val Ala Ala Ala Lys Ser Ser Glu Asn Asp Arg Leu Arg Leu
            35                  40                  45

Leu Leu Lys Gln Met Cys Lys Leu Ala Lys Phe Val Ala Ala Trp Thr
50                  55                  60

Leu Lys Ala Ala Ala Gly Ser Asp Glu Val Ser Gly Leu Glu Gln Leu
65                  70                  75                  80

Glu Ser Ile Ile Asn Phe Glu Lys Leu Thr Glu Trp Thr Ser Ser Asn
                85                  90                  95

Val Met Glu Glu Arg Lys Ile Lys Val Tyr Leu Pro Arg Met Lys Met
```

```
              100                 105                 110
Glu Glu Lys Tyr Asn Leu Thr Ser Val Leu Met Ala Met Gly Ile Thr
            115                 120                 125

Asp Val Phe Ser Ser Ser Ala Asn Leu Ser Gly Ile Ser Ser Ala Glu
        130                 135                 140

Ser Leu Lys Ile Ser Gln Ala Val His Ala Ala His Ala Glu Ile Asn
145                 150                 155                 160

Glu Ala Gly Arg Glu Val Val Gly Ser Ala Glu Ala Gly Val Asp Ala
                165                 170                 175

Ala Ser Val Ser Glu Glu Phe Arg Ala Asp His Pro Phe Leu Phe Cys
            180                 185                 190

Ile Lys His Ile Ala Thr Asn Ala Glu Cys Asp Ser Glu Leu Glu Ile
        195                 200                 205

Lys Arg Tyr Lys Asn Arg Val Ala Ser Arg Lys Cys Arg Ala Lys Phe
    210                 215                 220

Lys Gln Leu Leu Gln His Tyr Arg Glu Val Ala Ala Ala Lys Ser Ser
225                 230                 235                 240

Glu Asn Asp Arg Leu Arg Leu Leu Lys Gln
                245                 250

<210> SEQ ID NO 55
<211> LENGTH: 105
<212> TYPE: PRT
<213> ORGANISM: Artificial Sequence
<220> FEATURE:
<223> OTHER INFORMATION: Human protein derivative

<400> SEQUENCE: 55

Leu Ala Asp Ile Gly Val Pro Gln Pro Ala Pro Val Ala Ala Pro Ala
1               5                   10                  15

Arg Arg Thr Arg Lys Pro Gln Gln Pro Glu Ser Leu Glu Glu Cys Asp
            20                  25                  30

Ser Glu Leu Glu Ile Lys Arg Tyr Lys Asn Arg Val Ala Ser Arg Lys
        35                  40                  45

Cys Arg Ala Lys Phe Lys Gln Leu Leu Gln His Tyr Arg Glu Val Ala
    50                  55                  60

Ala Ala Lys Ser Ser Glu Asn Asp Arg Leu Arg Leu Leu Leu Lys Gln
65                  70                  75                  80

Met Cys Pro Ser Leu Asp Val Asp Ser Ile Ile Pro Arg Thr Pro Asp
                85                  90                  95

Val Leu His Glu Asp Leu Leu Asn Phe
            100                 105

<210> SEQ ID NO 56
<211> LENGTH: 75
<212> TYPE: PRT
<213> ORGANISM: Artificial Sequence
<220> FEATURE:
<223> OTHER INFORMATION: Human protein derivative

<400> SEQUENCE: 56

Cys Asp Ser Glu Leu Glu Ile Lys Arg Tyr Lys Asn Arg Val Ala Ser
1               5                   10                  15

Arg Lys Cys Arg Ala Lys Phe Lys Gln Leu Leu Gln His Tyr Arg Glu
            20                  25                  30

Val Ala Ala Ala Lys Ser Ser Glu Asn Asp Arg Leu Arg Leu Leu Leu
        35                  40                  45
```

```
Lys Gln Met Cys Pro Ser Leu Asp Val Asp Ser Ile Ile Pro Arg Thr
         50                  55                  60

Pro Asp Val Leu His Glu Asp Leu Leu Asn Phe
 65                  70                  75

<210> SEQ ID NO 57
<211> LENGTH: 52
<212> TYPE: PRT
<213> ORGANISM: Epstein-Barr virus

<400> SEQUENCE: 57

Glu Cys Asp Ser Glu Leu Glu Ile Lys Arg Tyr Lys Asn Arg Val Ala
 1               5                  10                  15

Ser Arg Lys Cys Arg Ala Lys Phe Lys Gln Leu Leu Gln His Tyr Arg
                20                  25                  30

Glu Val Ala Ala Ala Lys Ser Ser Glu Asn Asp Arg Leu Arg Leu Leu
             35                  40                  45

Leu Lys Gln Met
         50

<210> SEQ ID NO 58
<211> LENGTH: 18
<212> TYPE: DNA
<213> ORGANISM: Artificial Sequence
<220> FEATURE:
<223> OTHER INFORMATION: primer

<400> SEQUENCE: 58
agcactgact catgaagt                                                  18

<210> SEQ ID NO 59
<211> LENGTH: 19
<212> TYPE: DNA
<213> ORGANISM: Artificial Sequence
<220> FEATURE:
<223> OTHER INFORMATION: primer

<400> SEQUENCE: 59
tacttcatga gtcagtgct                                                 19

<210> SEQ ID NO 60
<211> LENGTH: 29
<212> TYPE: DNA
<213> ORGANISM: Artificial Sequence
<220> FEATURE:
<223> OTHER INFORMATION: primer

<400> SEQUENCE: 60
ccgctcgaga tgatggaccc aaactcgac                                      29

<210> SEQ ID NO 61
<211> LENGTH: 30
<212> TYPE: DNA
<213> ORGANISM: Artificial Sequence
<220> FEATURE:
<223> OTHER INFORMATION: primer

<400> SEQUENCE: 61
cgcggatccg aaatttaaga gatcctcgtg                                     30

<210> SEQ ID NO 62
<211> LENGTH: 33
<212> TYPE: DNA
<213> ORGANISM: Artificial Sequence
```

```
<220> FEATURE:
<223> OTHER INFORMATION: primer

<400> SEQUENCE: 62
cgcggatcct tagaaattta agagatcctc gtg                                    33

<210> SEQ ID NO 63
<211> LENGTH: 26
<212> TYPE: DNA
<213> ORGANISM: Artificial Sequence
<220> FEATURE:
<223> OTHER INFORMATION: primer

<400> SEQUENCE: 63
ggaattccat atggaccaaa ctcgac                                            26

<210> SEQ ID NO 64
<211> LENGTH: 32
<212> TYPE: DNA
<213> ORGANISM: Artificial Sequence
<220> FEATURE:
<223> OTHER INFORMATION: primer

<400> SEQUENCE: 64
cgcggatcct tattgcttaa acttggcccg gc                                     32

<210> SEQ ID NO 65
<211> LENGTH: 31
<212> TYPE: DNA
<213> ORGANISM: Artificial Sequence
<220> FEATURE:
<223> OTHER INFORMATION: primer

<400> SEQUENCE: 65
cgcggatcct tattcctcca gcgattctgg c                                      31

<210> SEQ ID NO 66
<211> LENGTH: 32
<212> TYPE: DNA
<213> ORGANISM: Artificial Sequence
<220> FEATURE:
<223> OTHER INFORMATION: primer

<400> SEQUENCE: 66
cgcggatcct tactgttgtc cttggttagc cc                                     32

<210> SEQ ID NO 67
<211> LENGTH: 36
<212> TYPE: DNA
<213> ORGANISM: Artificial Sequence
<220> FEATURE:
<223> OTHER INFORMATION: primer

<400> SEQUENCE: 67
ggaattccat atgcagctag cagacattgg tgttcc                                 36

<210> SEQ ID NO 68
<211> LENGTH: 32
<212> TYPE: DNA
<213> ORGANISM: Artificial Sequence
<220> FEATURE:
<223> OTHER INFORMATION: primer

<400> SEQUENCE: 68
ggaattccat atgcaactgc tgcagcacta cc                                     32
```

<210> SEQ ID NO 69
<211> LENGTH: 33
<212> TYPE: DNA
<213> ORGANISM: Artificial Sequence
<220> FEATURE:
<223> OTHER INFORMATION: primer

<400> SEQUENCE: 69
cgcggatcct tagaaattta agagatcctc gtg            33

<210> SEQ ID NO 70
<211> LENGTH: 30
<212> TYPE: DNA
<213> ORGANISM: Artificial Sequence
<220> FEATURE:
<223> OTHER INFORMATION: primer

<400> SEQUENCE: 70
ggaattccat atgccggtgc tgccagagcc                30

<210> SEQ ID NO 71
<211> LENGTH: 34
<212> TYPE: DNA
<213> ORGANISM: Artificial Sequence
<220> FEATURE:
<223> OTHER INFORMATION: primer

<400> SEQUENCE: 71
ggaattccat atggacataa cccagaatca acag           34

<210> SEQ ID NO 72
<211> LENGTH: 27
<212> TYPE: DNA
<213> ORGANISM: Artificial Sequence
<220> FEATURE:
<223> OTHER INFORMATION: primer

<400> SEQUENCE: 72
ccgctcgagc ggccacagca cacaagg                   27

<210> SEQ ID NO 73
<211> LENGTH: 30
<212> TYPE: DNA
<213> ORGANISM: Artificial Sequence
<220> FEATURE:
<223> OTHER INFORMATION: primer

<400> SEQUENCE: 73
ccgctcgagt atgtcggaga ctgggaacag                30

<210> SEQ ID NO 74
<211> LENGTH: 29
<212> TYPE: DNA
<213> ORGANISM: Artificial Sequence
<220> FEATURE:
<223> OTHER INFORMATION: primer

<400> SEQUENCE: 74
ccgctcgagc tgttgtcctt ggttagccc                 29

<210> SEQ ID NO 75
<211> LENGTH: 30
<212> TYPE: DNA
<213> ORGANISM: Artificial Sequence
<220> FEATURE:
<223> OTHER INFORMATION: primer

```
<400> SEQUENCE: 75
ccgctcgagg aaatttaaga gatcctcgtg                                      30

<210> SEQ ID NO 76
<211> LENGTH: 29
<212> TYPE: DNA
<213> ORGANISM: Artificial Sequence
<220> FEATURE:
<223> OTHER INFORMATION: primer

<400> SEQUENCE: 76
ccgctcgagt tgcttaaact tggcccggc                                       29

<210> SEQ ID NO 77
<211> LENGTH: 29
<212> TYPE: DNA
<213> ORGANISM: Artificial Sequence
<220> FEATURE:
<223> OTHER INFORMATION: primer

<400> SEQUENCE: 77
ccgctcgagc tgttgtcctt ggttagccc                                       29

<210> SEQ ID NO 78
<211> LENGTH: 36
<212> TYPE: DNA
<213> ORGANISM: Artificial Sequence
<220> FEATURE:
<223> OTHER INFORMATION: primer

<400> SEQUENCE: 78
ggaattccat atgcagctag cagacattgg tgttcc                               36

<210> SEQ ID NO 79
<211> LENGTH: 32
<212> TYPE: DNA
<213> ORGANISM: Artificial Sequence
<220> FEATURE:
<223> OTHER INFORMATION: primer

<400> SEQUENCE: 79
ggaattccat atgcaactgc tgcagcacta cc                                   32

<210> SEQ ID NO 80
<211> LENGTH: 35
<212> TYPE: DNA
<213> ORGANISM: Artificial Sequence
<220> FEATURE:
<223> OTHER INFORMATION: primer

<400> SEQUENCE: 80
ggaattccat atggaggaat gcgattctga actag                                35

<210> SEQ ID NO 81
<211> LENGTH: 28
<212> TYPE: DNA
<213> ORGANISM: Artificial Sequence
<220> FEATURE:
<223> OTHER INFORMATION: primer

<400> SEQUENCE: 81
ccgctcgagg cacatctgct tcaacagg                                        28

<210> SEQ ID NO 82
```

```
<211> LENGTH: 30
<212> TYPE: DNA
<213> ORGANISM: Artificial Sequence
<220> FEATURE:
<223> OTHER INFORMATION: primer

<400> SEQUENCE: 82
ccgctcgagt atgtcggaga ctgggaacag                                          30

<210> SEQ ID NO 83
<211> LENGTH: 36
<212> TYPE: DNA
<213> ORGANISM: Artificial Sequence
<220> FEATURE:
<223> OTHER INFORMATION: primer

<400> SEQUENCE: 83
ggaattccat atgaagcgat acaagaatcg ggtggc                                   36

<210> SEQ ID NO 84
<211> LENGTH: 30
<212> TYPE: DNA
<213> ORGANISM: Artificial Sequence
<220> FEATURE:
<223> OTHER INFORMATION: primer

<400> SEQUENCE: 84
ggaattccat atggtgagca agggcgagga                                          30

<210> SEQ ID NO 85
<211> LENGTH: 22
<212> TYPE: DNA
<213> ORGANISM: Artificial Sequence
<220> FEATURE:
<223> OTHER INFORMATION: primer

<400> SEQUENCE: 85
ccgctcgagc ttgtacagct cg                                                  22

<210> SEQ ID NO 86
<211> LENGTH: 27
<212> TYPE: DNA
<213> ORGANISM: Artificial Sequence
<220> FEATURE:
<223> OTHER INFORMATION: primer

<400> SEQUENCE: 86
ccgctcgaga tggtgagcaa gggcgag                                             27

<210> SEQ ID NO 87
<211> LENGTH: 29
<212> TYPE: DNA
<213> ORGANISM: Artificial Sequence
<220> FEATURE:
<223> OTHER INFORMATION: primer

<400> SEQUENCE: 87
cgcggatccc ttgtacagct cgtccatgc                                           29

<210> SEQ ID NO 88
<211> LENGTH: 47
<212> TYPE: DNA
<213> ORGANISM: Artificial Sequence
<220> FEATURE:
<223> OTHER INFORMATION: primer

<400> SEQUENCE: 88
```

```
ccgctcgaga tgattacgga ttcactggcc gtcgttttac aacgtcg                    47
```

<210> SEQ ID NO 89
<211> LENGTH: 31
<212> TYPE: DNA
<213> ORGANISM: Artificial Sequence
<220> FEATURE:
<223> OTHER INFORMATION: primer

<400> SEQUENCE: 89

```
cgcggatcct ttttgacacc agaccaactg g                                     31
```

<210> SEQ ID NO 90
<211> LENGTH: 35
<212> TYPE: DNA
<213> ORGANISM: Artificial Sequence
<220> FEATURE:
<223> OTHER INFORMATION: primer

<400> SEQUENCE: 90

```
taacgcctcg agaattttca acagaggctg caaag                                 35
```

<210> SEQ ID NO 91
<211> LENGTH: 40
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (33)..(33)
<223> OTHER INFORMATION: A OR T OR C OR G

<400> SEQUENCE: 91

```
attcttatgg atctttagag cttgtagatt ttntgcatcc                            40
```

<210> SEQ ID NO 92
<211> LENGTH: 29
<212> TYPE: DNA
<213> ORGANISM: Artificial Sequence
<220> FEATURE:
<223> OTHER INFORMATION: primer

<400> SEQUENCE: 92

```
ccgctcgagg gccaagaatt ccactttgg                                        29
```

<210> SEQ ID NO 93
<211> LENGTH: 45
<212> TYPE: DNA
<213> ORGANISM: Artificial Sequence
<220> FEATURE:
<223> OTHER INFORMATION: primer

<400> SEQUENCE: 93

```
taacgcctcg aggccacacc ggcggtacca gtaagtgctc ctccg                      45
```

<210> SEQ ID NO 94
<211> LENGTH: 39
<212> TYPE: DNA
<213> ORGANISM: Artificial Sequence
<220> FEATURE:
<223> OTHER INFORMATION: primer

<400> SEQUENCE: 94

```
attcttatgg atccttacag gtttacaagt ttttcattg                             39
```